(12) United States Patent
Ko et al.

(10) Patent No.: US 10,727,420 B2
(45) Date of Patent: Jul. 28, 2020

(54) COMPOUND AND ORGANIC LIGHT-EMITTING DEVICE INCLUDING THE SAME

(71) Applicant: Samsung Display Co., Ltd., Yongin-si, Gyeonggi-do (KR)

(72) Inventors: Soobyung Ko, Yongin-si (KR); Haejin Kim, Yongin-si (KR); Mieun Jun, Yongin-si (KR); Youngkook Kim, Yongin-si (KR); Seokhwan Hwang, Yongin-si (KR)

(73) Assignee: SAMSUNG DISPLAY CO., LTD., Yongin-si, Gyeonggi-Do (KR)

( * ) Notice: Subject to any disclaimer, the term of this patent is extended or adjusted under 35 U.S.C. 154(b) by 268 days.

(21) Appl. No.: 15/841,021

(22) Filed: Dec. 13, 2017

(65) Prior Publication Data
US 2018/0166637 A1    Jun. 14, 2018

(30) Foreign Application Priority Data

Dec. 13, 2016 (KR) .......... 10-2016-0169749

(51) Int. Cl.
*H01L 51/50* (2006.01)
*H01L 51/00* (2006.01)
(Continued)

(52) U.S. Cl.
CPC ........ *H01L 51/0072* (2013.01); *C07C 225/22* (2013.01); *C07D 209/86* (2013.01); *C07D 307/91* (2013.01); *C07D 401/14* (2013.01); *C07D 403/14* (2013.01); *C07F 5/02* (2013.01); *C07F 5/025* (2013.01); *C07F 5/04* (2013.01);

*C09K 11/06* (2013.01); *H01L 51/008* (2013.01); *H01L 51/0052* (2013.01);
(Continued)

(58) Field of Classification Search
None
See application file for complete search history.

(56) References Cited

U.S. PATENT DOCUMENTS 7,053,255 B2    5/2006 Ikeda et al.
7,233,019 B2    6/2007 Ionkin et al.
(Continued)

FOREIGN PATENT DOCUMENTS

| KR | 10-2006-0006760 A | 1/2006 |
|---|---|---|
| KR | 10-2010-0097182 A | 9/2010 |
| KR | 10-1031463 B1 | 4/2011 |

OTHER PUBLICATIONS

Livant et al. A New Route to Hindered Tertiary Amines, 2001, J. Org. Chem., 66, 6729-6733 (Year: 2001).*

*Primary Examiner* — Gregory D Clark
(74) *Attorney, Agent, or Firm* — Kile Park Reed & Houtteman PLLC

(57) ABSTRACT

Provided is a compound represented by Formula 1 below:

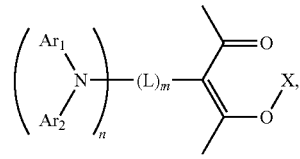

<Formula 1> wherein Formula 1 is described in the detailed description.

20 Claims, 1 Drawing Sheet

(51) Int. Cl.
  *C07D 209/86* (2006.01)
  *C07F 5/04* (2006.01)
  *C09K 11/06* (2006.01)
  *C07C 225/22* (2006.01)
  *C07D 403/14* (2006.01)
  *C07F 5/02* (2006.01)
  *C07D 307/91* (2006.01)
  *C07D 401/14* (2006.01)
  *H01L 27/32* (2006.01)

(52) U.S. Cl.
  CPC ...... *H01L 51/0077* (2013.01); *C07C 2603/18* (2017.05); *C07C 2603/24* (2017.05); *C07C 2603/42* (2017.05); *C07C 2603/50* (2017.05); *C09K 2211/1007* (2013.01); *C09K 2211/1011* (2013.01); *C09K 2211/1014* (2013.01); *C09K 2211/1018* (2013.01); *C09K 2211/1029* (2013.01); *C09K 2211/188* (2013.01); *H01L 27/3244* (2013.01); *H01L 51/006* (2013.01); *H01L 51/5012* (2013.01); *H01L 51/5024* (2013.01); *H01L 51/5036* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/5384* (2013.01)

(56) References Cited

U.S. PATENT DOCUMENTS

| | | |
|---|---|---|
| 2004/0137264 A1 | 7/2004 | Kathirgamanathan et al. |
| 2004/0241493 A1 | 12/2004 | Inoue et al. |
| 2010/0270915 A1 | 10/2010 | Cheng et al. |
| 2011/0006289 A1 | 1/2011 | Mizuki et al. |
| 2012/0027915 A1 | 2/2012 | Van Eert et al. |
| 2013/0069523 A1 | 3/2013 | Matsuura et al. |
| 2014/0138670 A1 | 5/2014 | Nakagawa et al. |

* cited by examiner

10

| 190 |
|---|
| 150 |
| 110 |

COMPOUND AND ORGANIC LIGHT-EMITTING DEVICE INCLUDING THE SAME

CROSS-REFERENCE TO RELATED APPLICATION

This application claims the benefit of Korean Patent Application No. 10-2016-0169749 filed on Dec. 13, 2016 in the Korean Intellectual Property Office, the disclosure of which is incorporated herein in its entirety by reference.

BACKGROUND

1. Field

One or more embodiments relate to a compound and an organic light-emitting device including the same.

2. Description of the Related Art

Organic light-emitting devices are self-emission devices that produce full-color images, and also have wide viewing angles, high contrast ratios, short response times, as well as excellent characteristics in terms of brightness, driving voltage, and response speed.

An example of such organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit from an excited state to a ground state, thereby generating light.

SUMMARY

Aspects of the present invention provide a compound suitable for use as a light-emitting material and an organic light-emitting device that includes the compound and thus has high efficiency, a low driving voltage, high luminance, and a long lifespan.

Additional aspects will be set forth in part in the description which follows and, in part, will be apparent from the description, or may be learned by practice of the presented embodiments.

An aspect provides a compound represented by Formula 1 below:

<Formula 1>

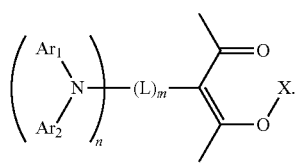

In Formula 1, $Ar_1$ and $Ar_2$ may each independently be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

L may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, m may be an integer from 1 to 5, when m is two or more, two or more L(s) may be identical to or different from each other, n may be an integer from 1 to 3, when n is two or more, two or more $Ar_1$(s) may be identical to or different from each other, and two or more $Ar_2$(s) may be identical to or different from each other, X may be hydrogen or a boron compound, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Another aspect provides an organic light-emitting device including: a first electrode; a second electrode facing the first electrode; and an organic layer that is disposed between the first electrode and the second electrode and includes an emission layer, wherein the organic layer includes the compound described above.

Another aspect provides a display apparatus including the organic light-emitting device, wherein the first electrode of the organic light-emitting device is electrically connected to a source electrode or a drain electrode of a thin film transistor.

BRIEF DESCRIPTION OF THE DRAWING

These and/or other aspects will become apparent and more readily appreciated from the following description of the embodiments, taken in conjunction with FIG. 1 which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

A compound according to an embodiment is represented by Formula 1 below:

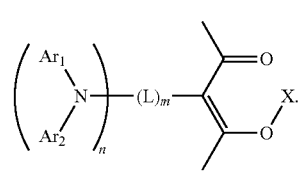

<Formula 1>

In Formula 1, $Ar_1$ and $Ar_2$ may each independently be selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, L may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, m may be an integer from 1 to 5, when m is two or more, two or more L(s) may be identical to or different from each other, n may be an integer from 1 to 3, when n is two or more, two or more $Ar_1$(s) may be identical to or different from each other, and two or more $Ar_2$(s) may be identical to or different from each other, X may be hydrogen or a boron compound, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_6$-$C_{60}$ arylene group, the substituted $C_1$-$C_{60}$ heteroarylene group, the substituted divalent non-aromatic condensed polycyclic group, and the substituted divalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Disclosed are a blue fluorescent light-emitting material, which has a diphenylanthracene structure as its center and an aryl group as its end, and an organic light-emitting device using the same, but light emission efficiency and luminance thereof are insufficient.

Meanwhile, disclosed is an organic light-emitting device using a substituted pyrene-based arylamine compound, various diamine compounds, a chrysene-based arylamine compound, or the like, but it is difficult to realize a deep blue color due to low blue color purity. Consequently, it is difficult to realize a full-color display capable of producing natural colors.

A novel beta-diketone condensed compound according to an embodiment has a new structure that provides distinctive optical characteristics due to the structure itself thereof. The beta-diketone condensed compound combines with an arylamine substituent including various condensed polycyclic groups to provide a deep blue compound having high efficiency and a long lifespan.

The compounds of Formula 1 according to one or more embodiments have a function as a light-emitting material. Also, compounds including molecules of Formula 1 are advantageous in terms of light emission efficiency and energy transfer due to the introduction of novel arylamine beta-diketone. An organic light-emitting device manufactured by using such arylamine beta-diketone has high durability in driving. Also, the compounds may combine with existing fluorescent and phosphorescent dopants to improve the efficiency and lifespan characteristics of an organic light-emitting device.

X in Formula 1 may be linked to O of ketone, as indicated by an arrow.

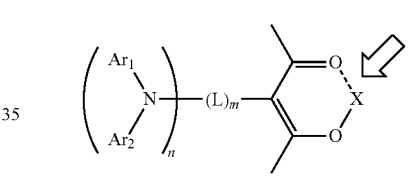

In one embodiment, in Formula 1, X may be hydrogen, $BF_2$, $BCl_2$, $BBr_2$, $BI_2$, or $BR_{11}R_{12}$, and $R_{11}$ and $R_{12}$ may be a substituted or unsubstituted $C_6$-$C_{60}$ aryl group. In one embodiment, X in Formula 1 may be hydrogen, $BF_2$, $BMes_2$, or $B(C_6F_5)_2$. Mes indicates mesitylene.

In one embodiment, two neighboring substituents selected from $Ar_1$, $Ar_2$, and L in Formula 1 may be linked to form a ring.

In one embodiment, $Ar_1$ and $Ar_2$ in Formula 1 may each independently be represented by one of Formulae 2a to 2c:

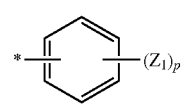

2a

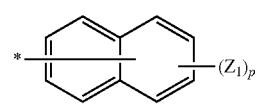

2b

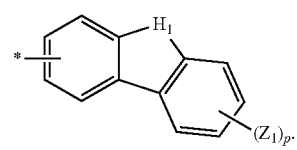

2c

In Formulae 2a to 2c, $H_1$ may be O, S, $NR_{21}$, or $CR_{22}R_{23}$, $R_{21}$ to $R_{23}$ and $Z_1$ may each independently be selected from hydrogen, deuterium, halogen, a substituted or unsubstituted $C_1$-$C_{20}$ alkyl group, a substituted or unsubstituted $C_1$-$C_{20}$ alkenyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, p may be an integer from 1 to 7, when p is two or more, two or more $Z_1$(s) may be identical to or different from each other, and

* indicates a binding site.

In one embodiment, L in Formula 1 may be represented by one of Formulae 3a to 3g:

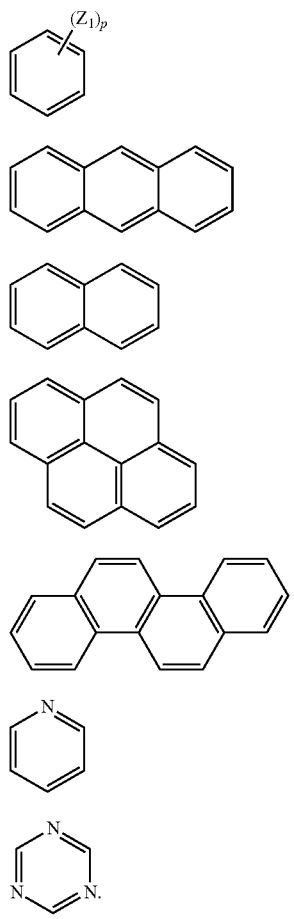

3a

3b

3c

3d

3e

3f

3g

In Formulae 3a to 3g, $Z_1$ may be selected from hydrogen, deuterium, halogen, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, and when p is two or more, two or more $Z_1$ (s) may be identical to or different from each other.

In Formulae 3a to 3g, a bond is formed at a hydrogen site.

In one embodiment, the compound represented by Formula 1 may be represented by Formula 2 or 3:

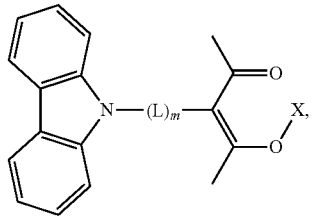

<Formula 2>

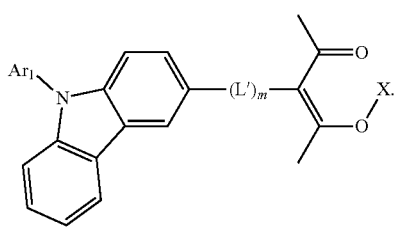

<Formula 3>

Symbols and substituents in Formulae 2 and 3 are the same as described herein, and L' in Formula 3 is the same as described in connection with L in Formula 1.

In one or more embodiments, the compound represented by Formula 1 may be one selected from the following compounds illustrated below, but embodiments of the present disclosure are not limited thereto:

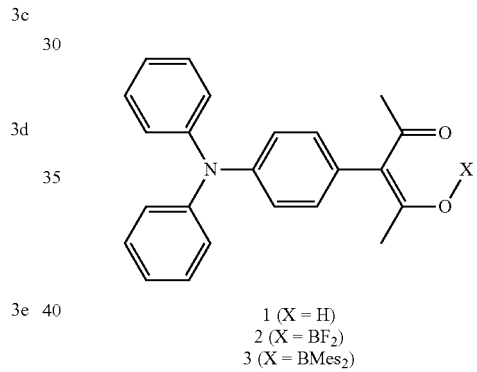

1 (X = H)
2 (X = BF$_2$)
3 (X = BMes$_2$)

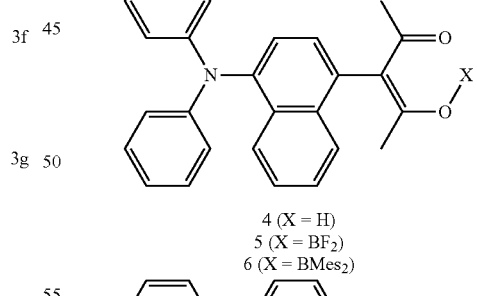

4 (X = H)
5 (X = BF$_2$)
6 (X = BMes$_2$)

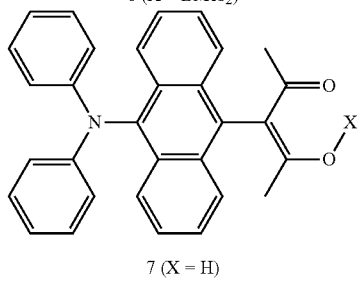

7 (X = H)
8 (X = BF$_2$)
9 (X = BMes$_2$)

-continued
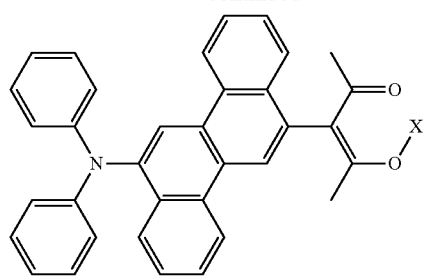
10 (X = H)
11 (X = BF₂)
12 (X = BMes₂)
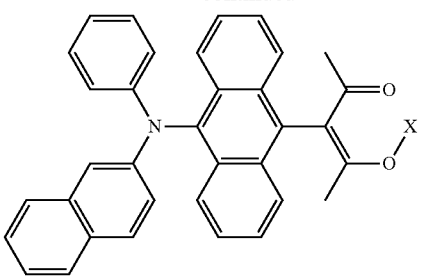
22 (X = H)
23 (X = BF₂)
24 (X = BMes₂)
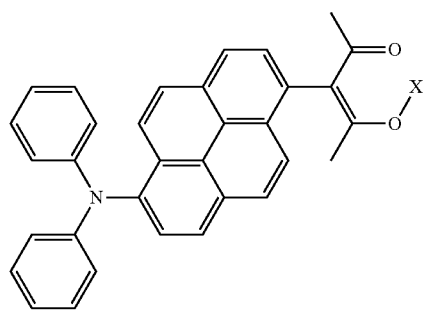
13 (X = H)
14 (X = BF₂)
15 (X = BMes₂)
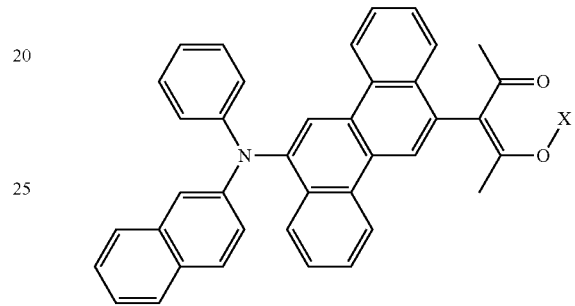
25 (X = H)
26 (X = BF₂)
27 (X = BMes₂)
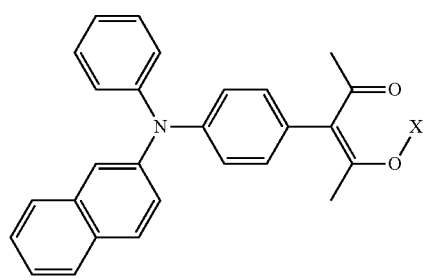
16 (X = H)
17 (X = BF₂)
18 (X = BMes₂)
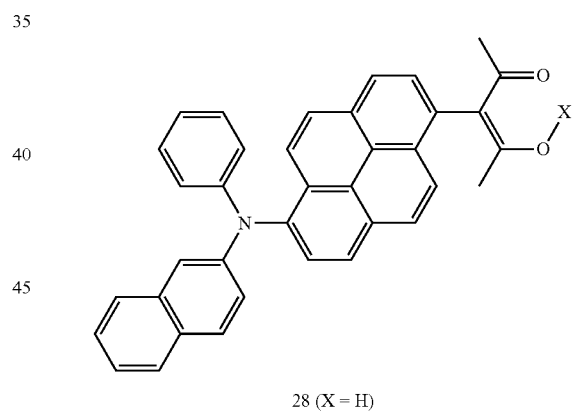
28 (X = H)
29 (X = BF₂)
30 (X = BMes₂)
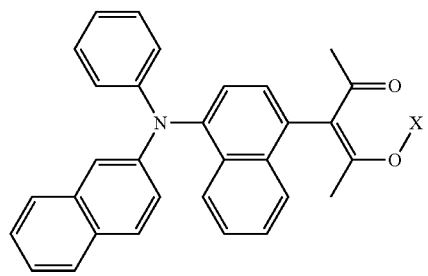
19 (X = H)
20 (X = BF₂)
21 (X = BMes₂)
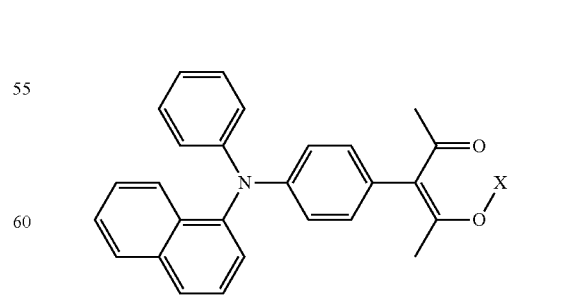
31 (X = H)
32 (X = BF₂)
33 (X = BMes₂)

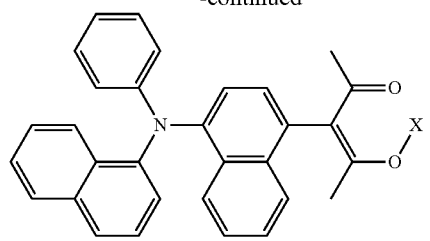
34 (X = H)
35 (X = BF$_2$)
36 (X = BMes$_2$)
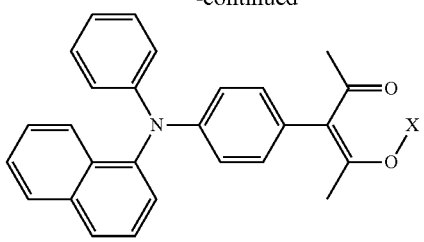
46 (X = H)
47 (X = BF$_2$)
48 (X = BMes$_2$)
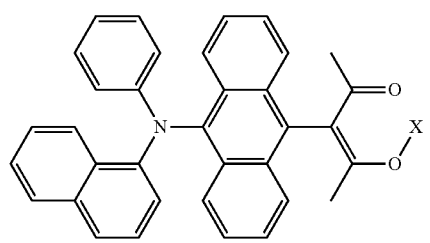
37 (X = H)
38 (X = BF$_2$)
39 (X = BMes$_2$)
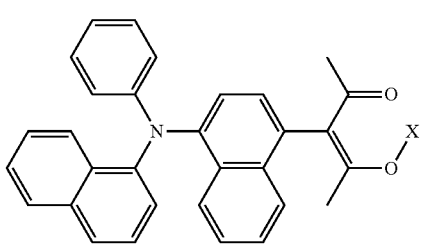
49 (X = H)
50 (X = BF$_2$)
51 (X = BMes$_2$)
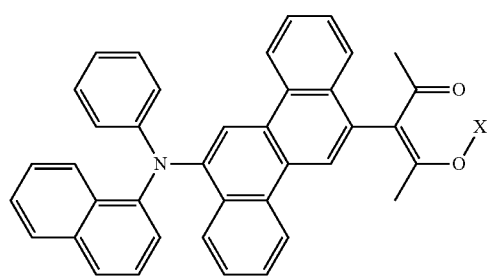
40 (X = H)
41 (X = BF$_2$)
42 (X = BMes$_2$)
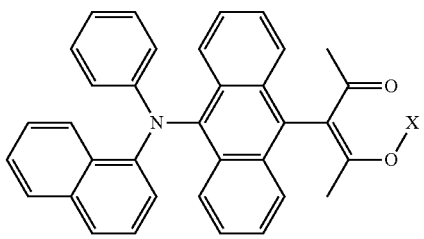
52 (X = H)
53 (X = BF$_2$)
54 (X = BMes$_2$)
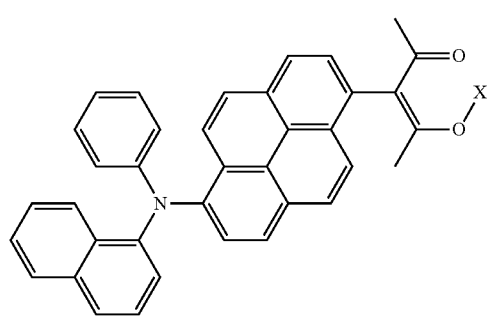
43 (X = H)
44 (X = BF$_2$)
45 (X = BMes$_2$)
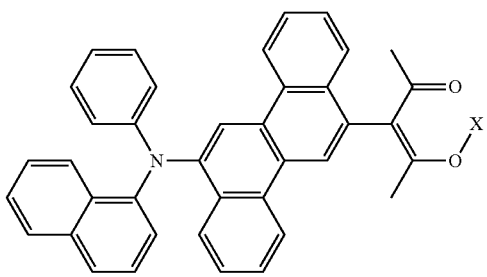
55 (X = H)
56 (X = BF$_2$)
57 (X = BMes$_2$)

-continued
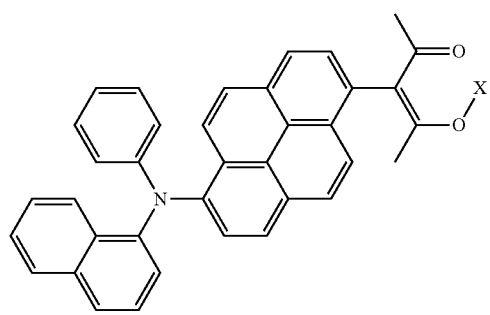
58 (X = H)
59 (X = BF$_2$)
60 (X = BMes$_2$)
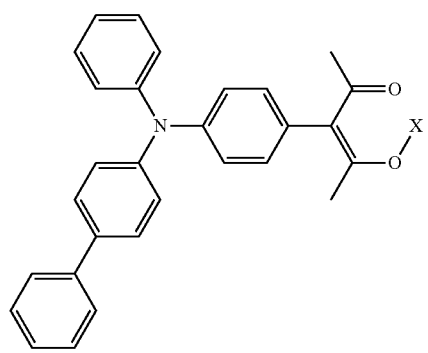
61 (X = H)
62 (X = BF$_2$)
63 (X = BMes$_2$)
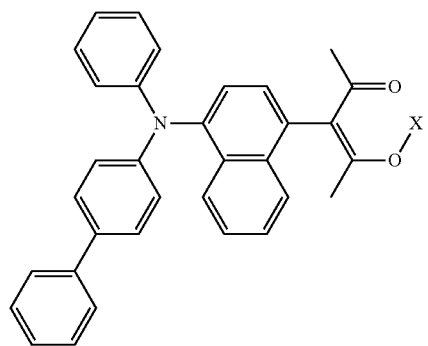
64 (X = H)
65 (X = BF$_2$)
66 (X = BMes$_2$)
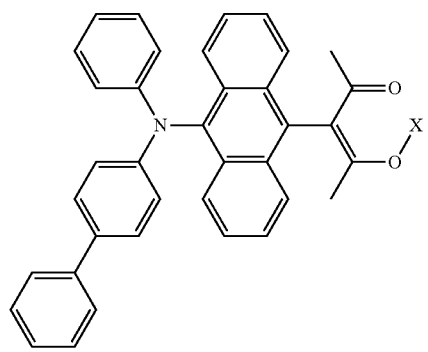
67 (X = H)
68 (X = BF$_2$)
69 (X = BMes$_2$)
-continued
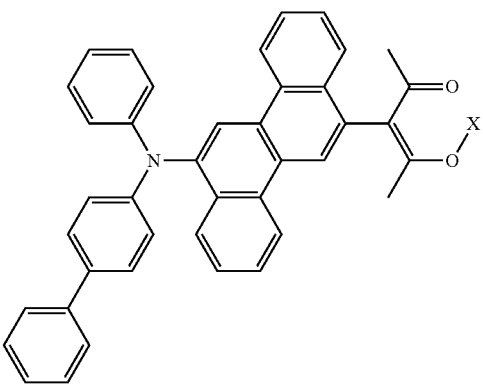
70 (X = H)
71 (X = BF$_2$)
72 (X = BMes$_2$)
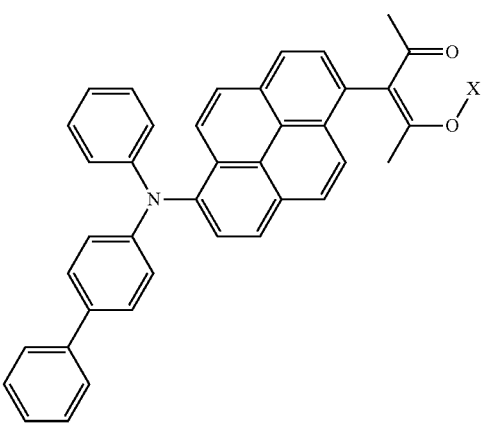
73 (X = H)
74 (X = BF$_2$)
75 (X = BMes$_2$)
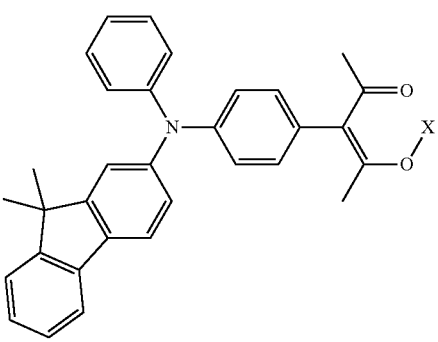
76 (X = H)
77 (X = BF$_2$)
78 (X = BMes$_2$)

-continued
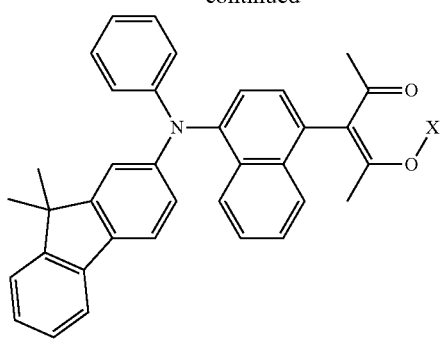
79 (X = H)
80 (X = BF$_2$)
81 (X = BMes$_2$)
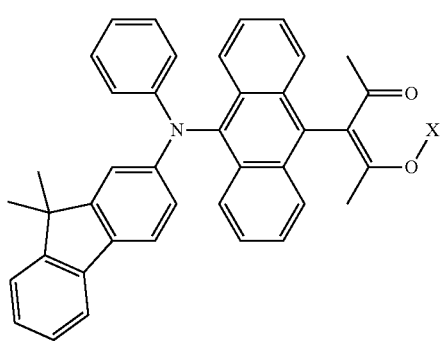
82 (X = H)
83 (X = BF$_2$)
84 (X = BMes$_2$)
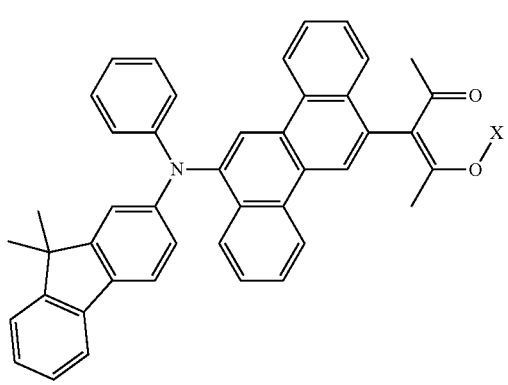
85 (X = H)
86 (X = BF$_2$)
87 (X = BMes$_2$)
-continued
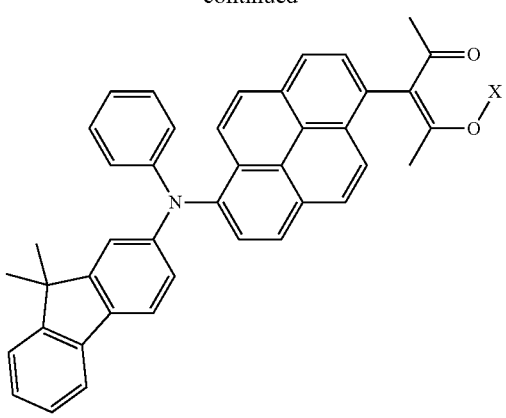
88 (X = H)
89 (X = BF$_2$)
90 (X = BMes$_2$)
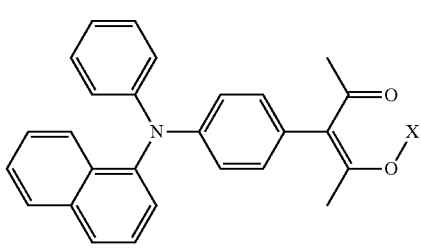
91 (X = H)
92 (X = BF$_2$)
93 (X = BMes$_2$)
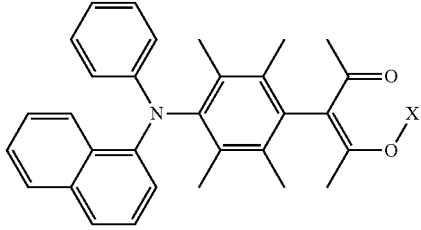
94 (X = H)
95 (X = BF$_2$)
96 (X = BMes$_2$)
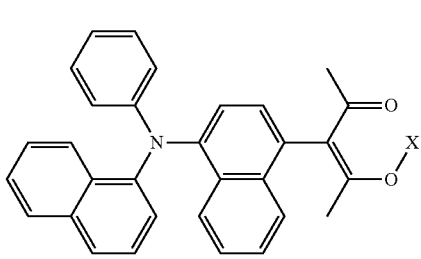
97 (X = H)
98 (X = BF$_2$)
99 (X = BMes$_2$)

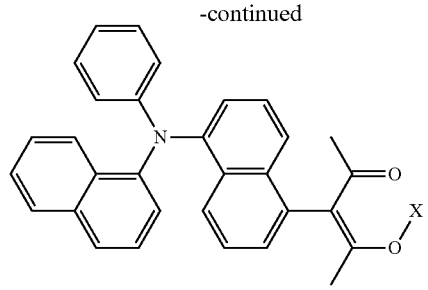
100 (X = H)
101 (X = BF₂)
102 (X = BMes₂)
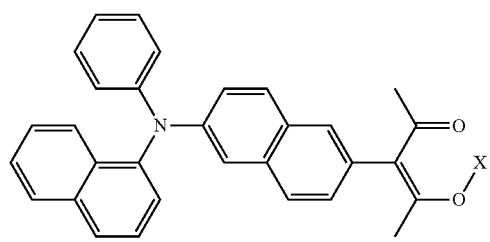
103 (X = H)
104 (X = BF₂)
105 (X = BMes₂)
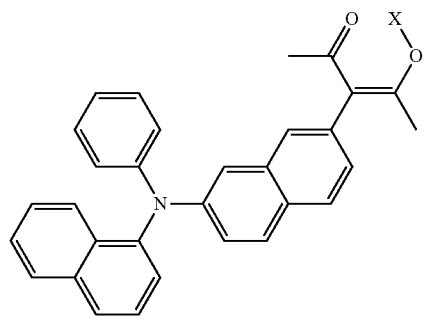
106 (X = H)
107 (X = BF₂)
108 (X = BMes₂)
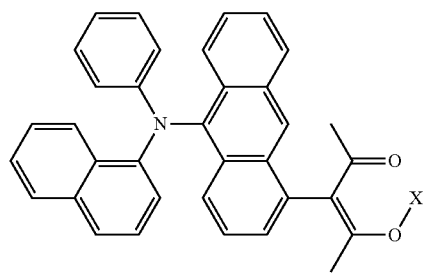
109 (X = H)
110 (X = BF₂)
111 (X = BMes₂)
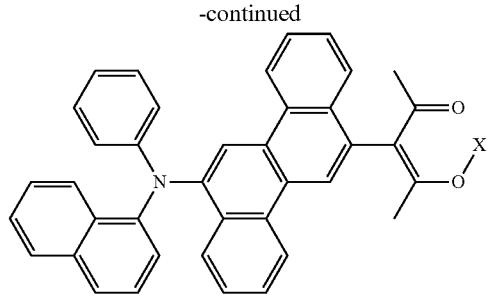
112 (X = H)
113 (X = BF₂)
114 (X = BMes₂)
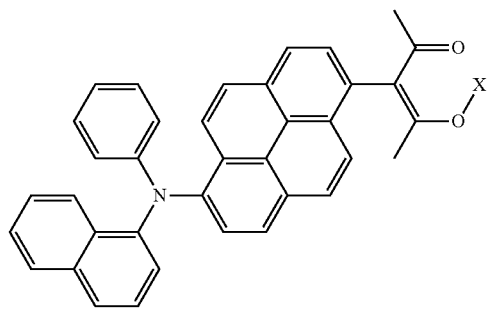
115 (X = H)
116 (X = BF₂)
117 (X = BMes₂)
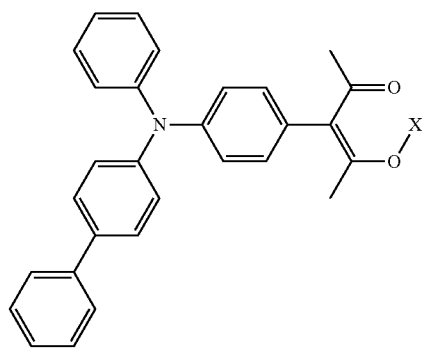
118 (X = H)
119 (X = BF₂)
120 (X = BMes₂)
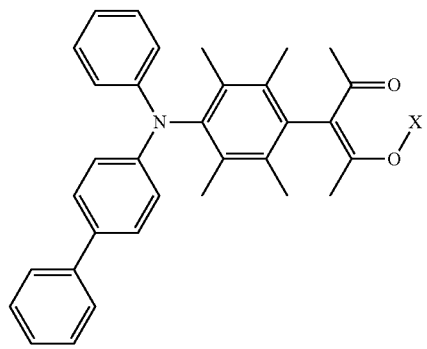
121 (X = H)
122 (X = BF₂)
123 (X = BMes₂)

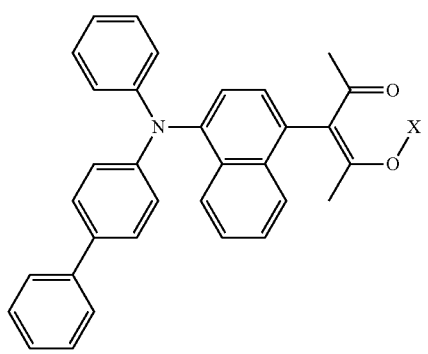
124 (X = H)
125 (X = BF₂)
126 (X = BMes₂)
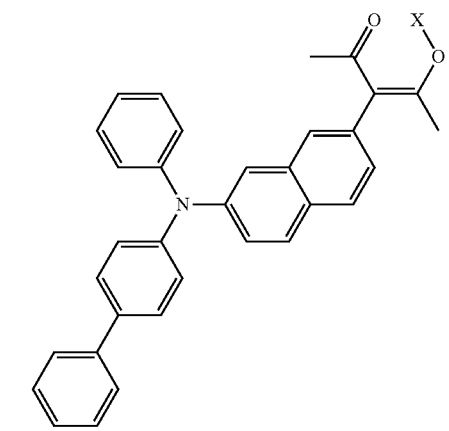
133 (X = H)
134 (X = BF₂)
135 (X = BMes₂)
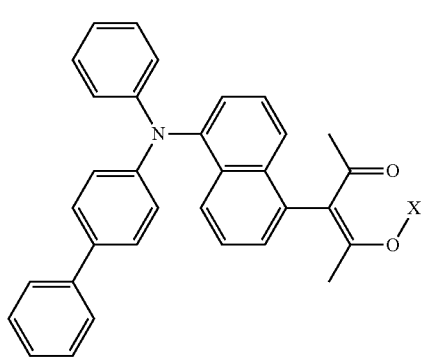
127 (X = H)
128 (X = BF₂)
139 (X = BMes₂)
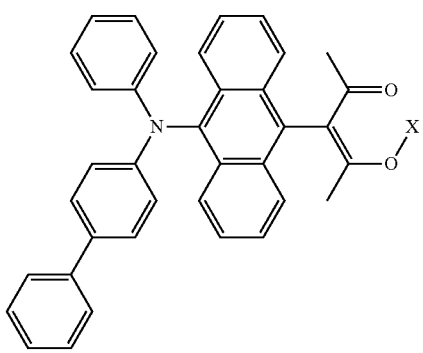
136 (X = H)
137 (X = BF₂)
138 (X = BMes₂)
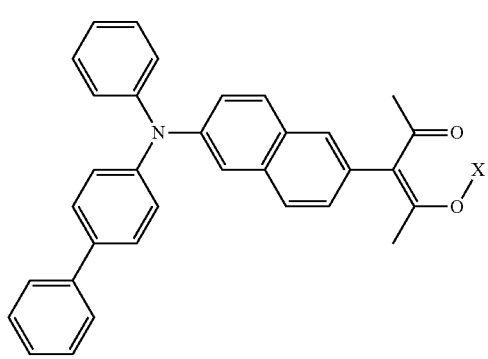
130 (X = H)
131 (X = BF₂)
132 (X = BMes₂)
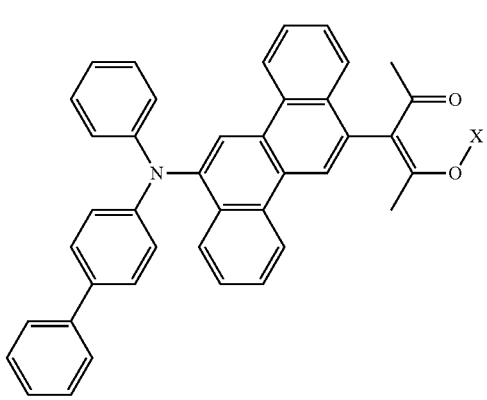
139 (X = H)
140 (X = BF₂)
141 (X = BMes₂)

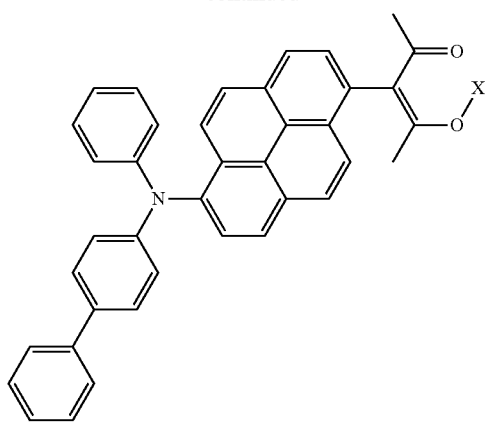
142 (X = H)
143 (X = BF₂)
144 (X = BMes₂)
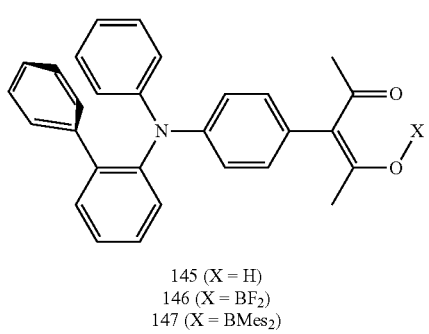
145 (X = H)
146 (X = BF₂)
147 (X = BMes₂)
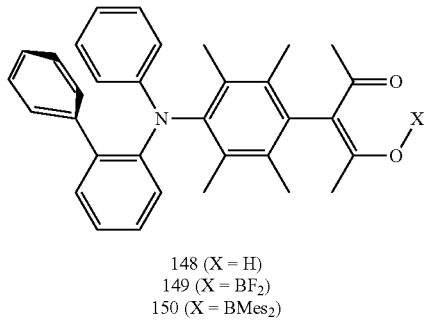
148 (X = H)
149 (X = BF₂)
150 (X = BMes₂)
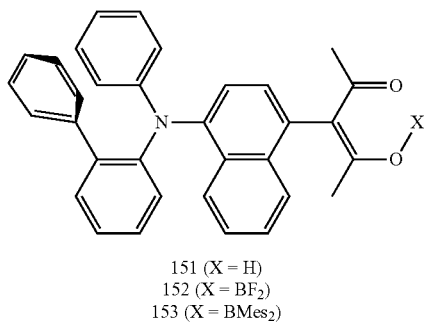
151 (X = H)
152 (X = BF₂)
153 (X = BMes₂)
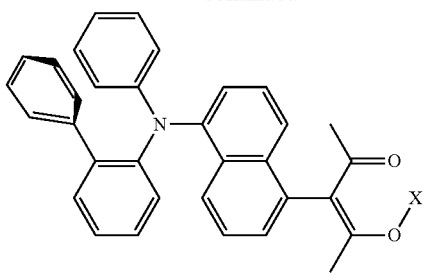
154 (X = H)
155 (X = BF₂)
156 (X = BMes₂)
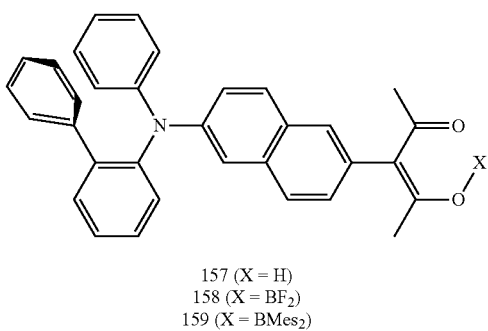
157 (X = H)
158 (X = BF₂)
159 (X = BMes₂)
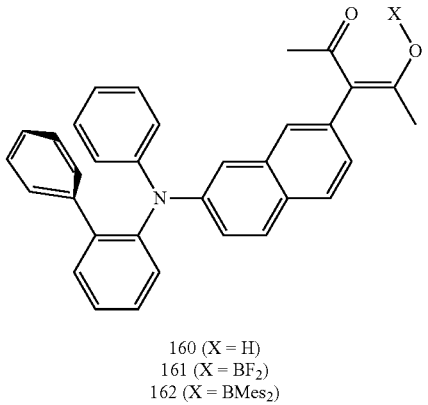
160 (X = H)
161 (X = BF₂)
162 (X = BMes₂)
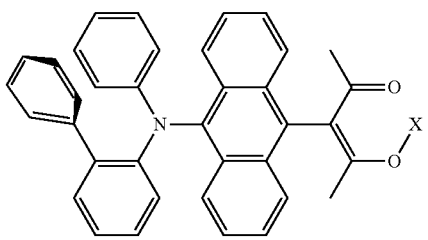
163 (X = H)
164 (X = BF₂)
165 (X = BMes₂)

-continued
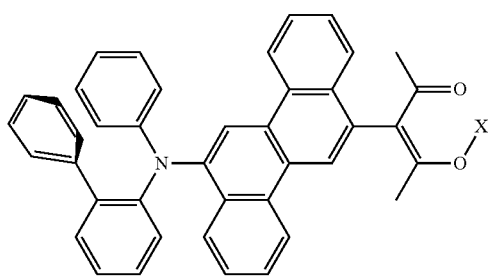
166 (X = H)
167 (X = BF$_2$)
168 (X = BMes$_2$)
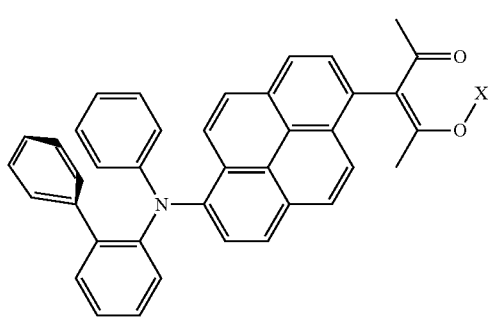
169 (X = H)
170 (X = BF$_2$)
171 (X = BMes$_2$)
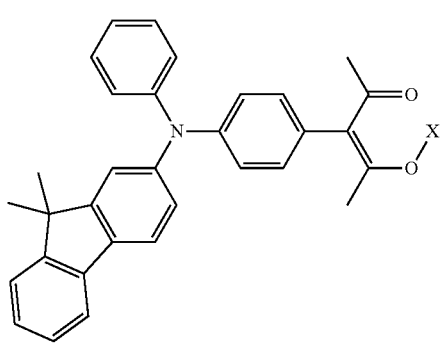
172 (X = H)
173 (X = BF$_2$)
174 (X = BMes$_2$)
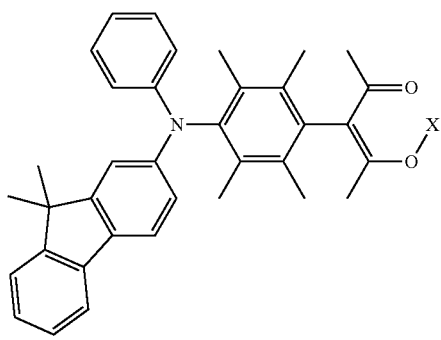
175 (X = H)
176 (X = BF$_2$)
177 (X = BMes$_2$)
-continued
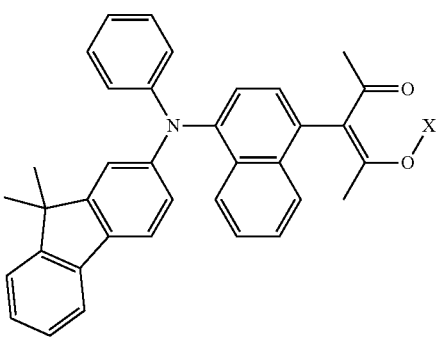
178 (X = H)
179 (X = BF$_2$)
180 (X = BMes$_2$)
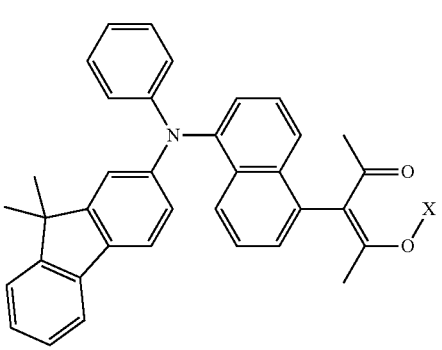
181 (X = H)
182 (X = BF$_2$)
183 (X = BMes$_2$)
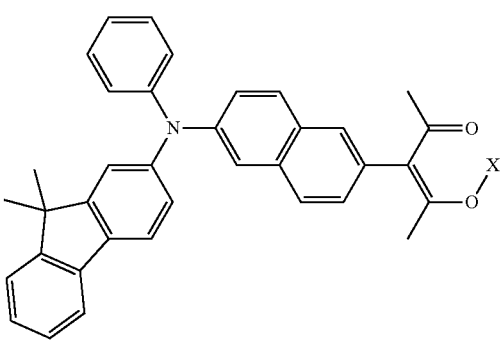
184 (X = H)
185 (X = BF$_2$)
186 (X = BMes$_2$)

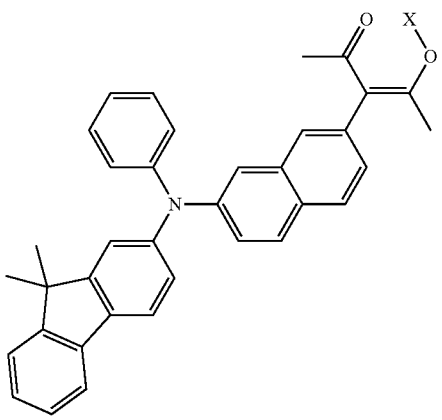
187 (X = H)
188 (X = BF₂)
189 (X = BMes₂)
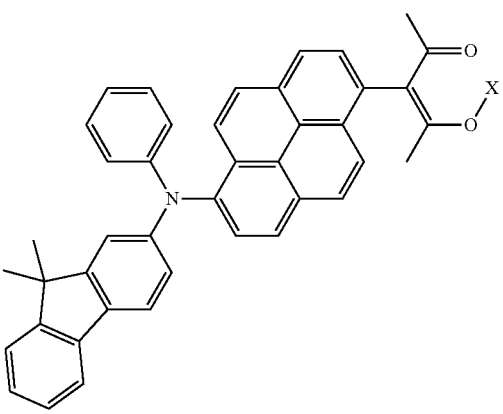
196 (X = H)
197 (X = BF₂)
198 (X = BMes₂)
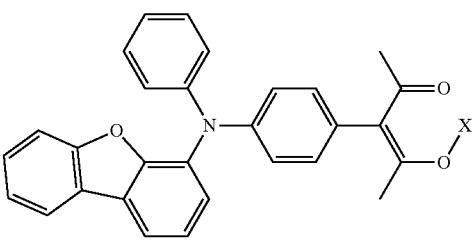
199 (X = H)
200 (X = BF₂)
201 (X = BMes₂)
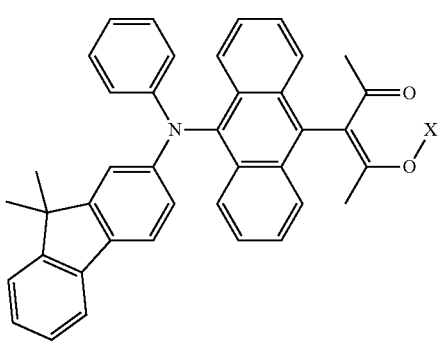
190 (X = H)
191 (X = BF₂)
192 (X = BMes₂)
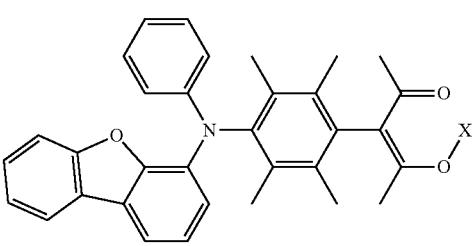
202 (X = H)
203 (X = BF₂)
204 (X = BMes₂)
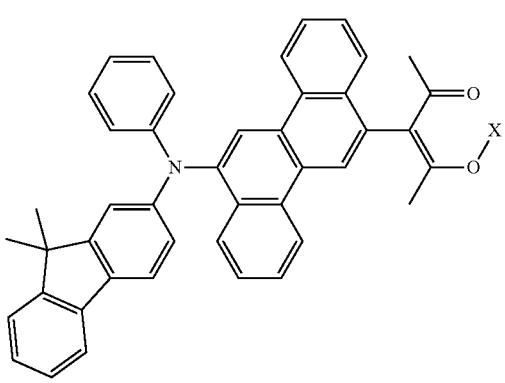
193 (X = H)
194 (X = BF₂)
195 (X = BMes₂)
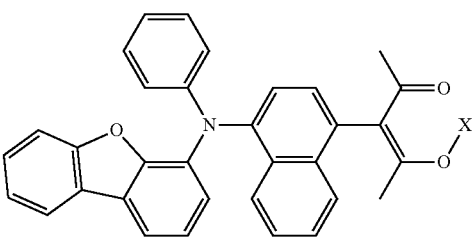
205 (X = H)
206 (X = BF₂)
207 (X = BMes₂)

-continued
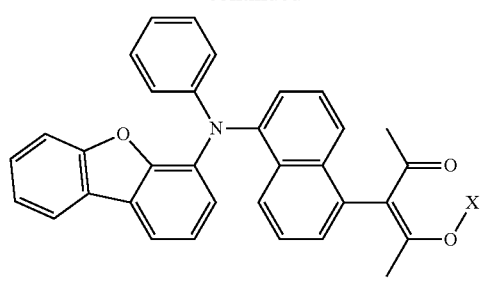
208 (X = H)
209 (X = BF$_2$)
210 (X = BMes$_2$)
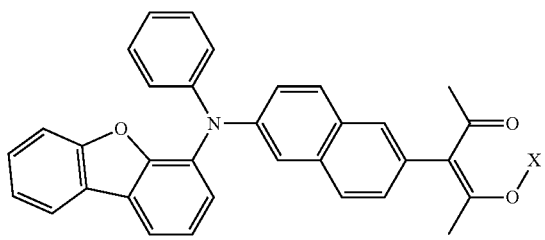
211 (X = H)
212 (X = BF$_2$)
213 (X = BMes$_2$)
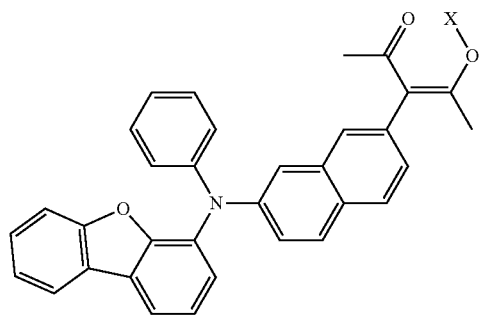
214 (X = H)
215 (X = BF$_2$)
216 (X = BMes$_2$)
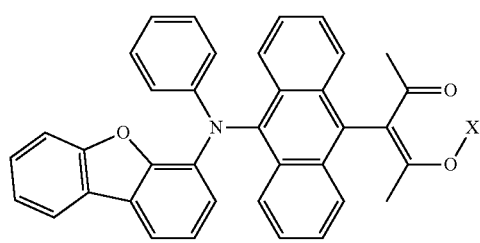
217 (X = H)
218 (X = BF$_2$)
219 (X = BMes$_2$)
-continued
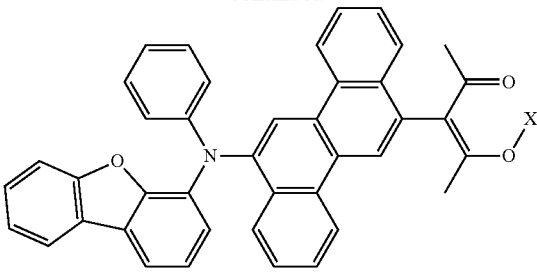
220 (X = H)
221 (X = BF$_2$)
222 (X = BMes$_2$)
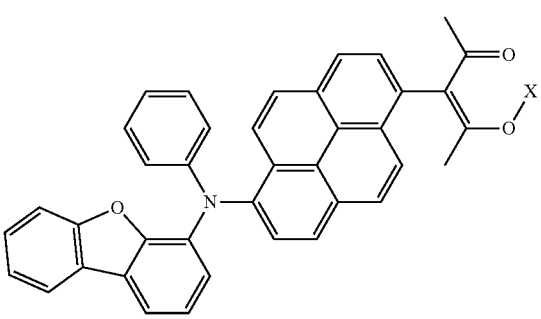
223 (X = H)
224 (X = BF$_2$)
225 (X = BMes$_2$)
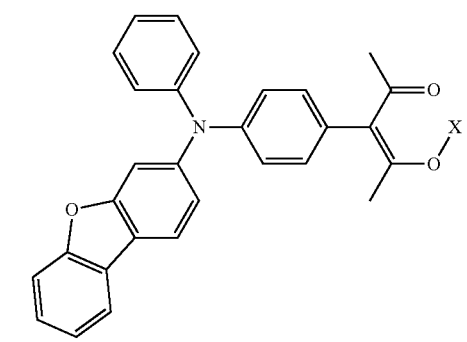
226 (X = H)
227 (X = BF$_2$)
228 (X = BMes$_2$)
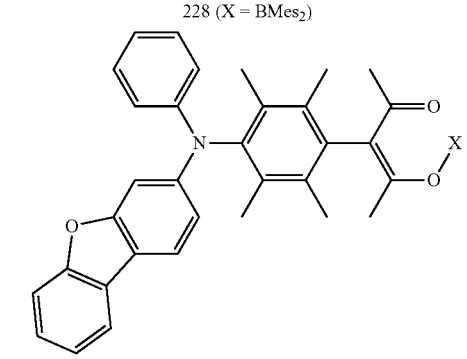
229 (X = H)
230 (X = BF$_2$)
231 (X = BMes$_2$)

-continued
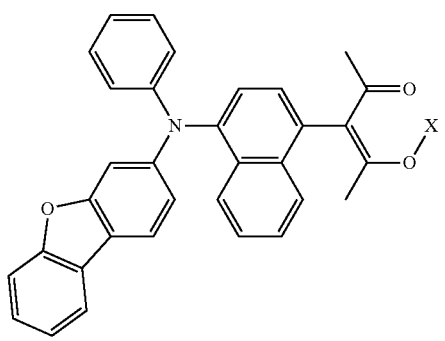
232 (X = H)
233 (X = BF₂)
234 (X = BMes₂)
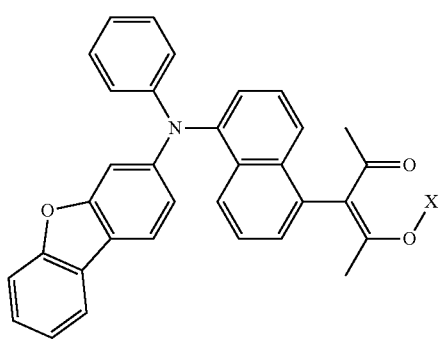
235 (X = H)
236 (X = BF₂)
237 (X = BMes₂)
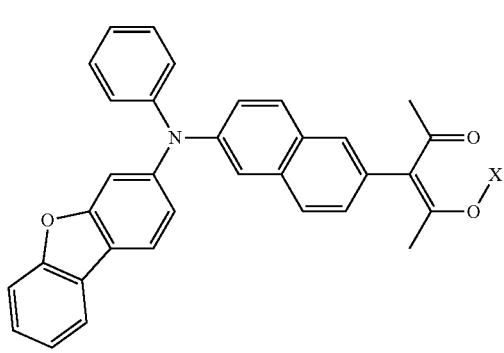
238 (X = H)
239 (X = BF₂)
240 (X = BMes₂)
-continued
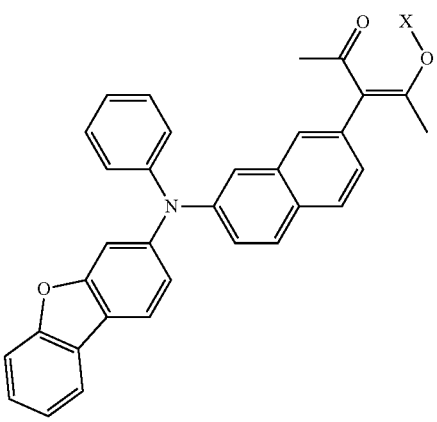
241 (X = H)
242 (X = BF₂)
243 (X = BMes₂)
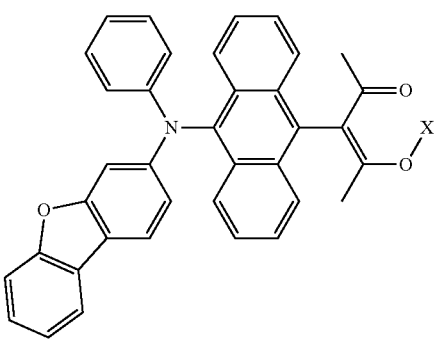
244 (X = H)
245 (X = BF₂)
246 (X = BMes₂)
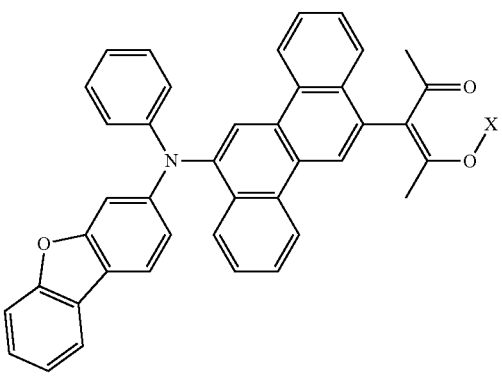
247 (X = H)
248 (X = BF₂)
249 (X = BMes₂)

-continued
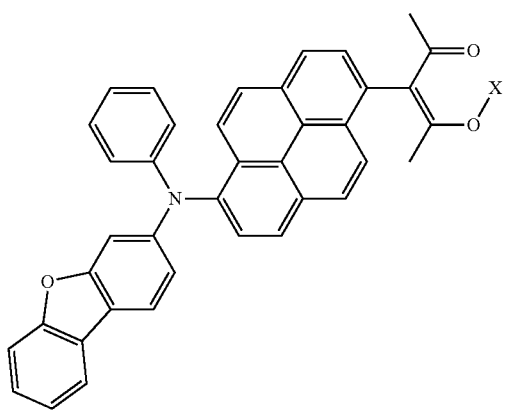
250 (X = H)
251 (X = BF$_2$)
252 (X = BMes$_2$)
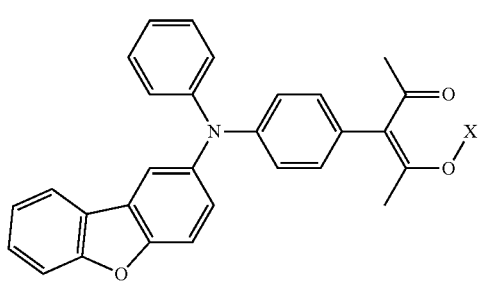
253 (X = H)
254 (X = BF$_2$)
255 (X = BMes$_2$)
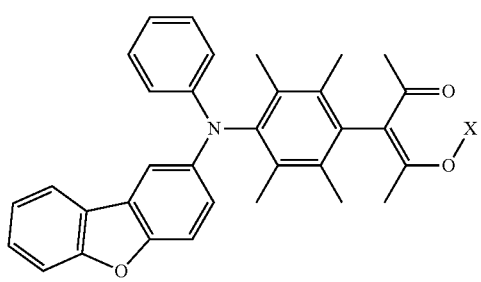
256 (X = H)
257 (X = BF$_2$)
258 (X = BMes$_2$)
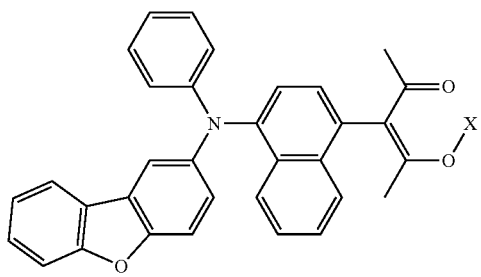
259 (X = H)
260 (X = BF$_2$)
261 (X = BMes$_2$)
-continued
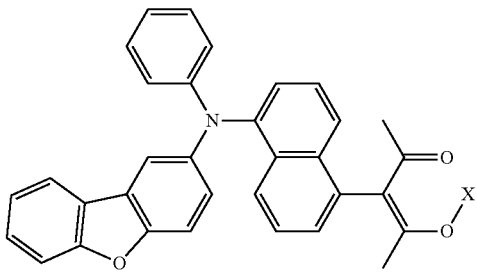
262 (X = H)
263 (X = BF$_2$)
264 (X = BMes$_2$)
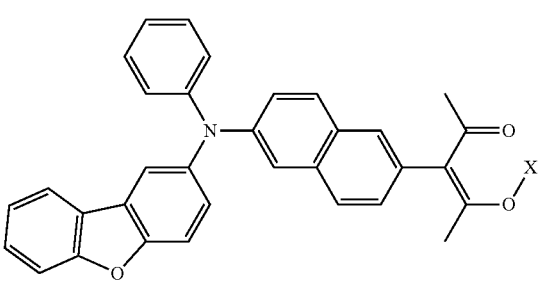
265 (X = H)
266 (X = BF$_2$)
267 (X = BMes$_2$)
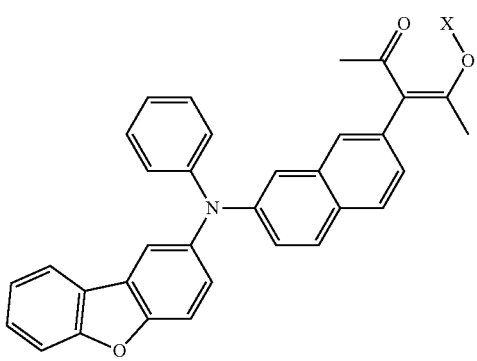
268 (X = H)
269 (X = BF$_2$)
270 (X = BMes$_2$)
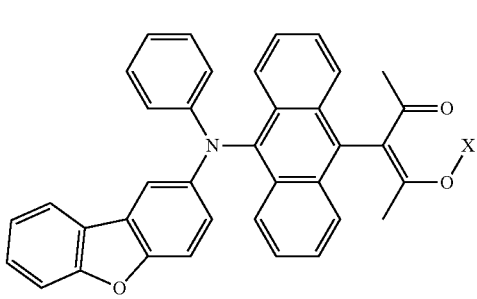
271 (X = H)
272 (X = BF$_2$)
273 (X = BMes$_2$)

-continued
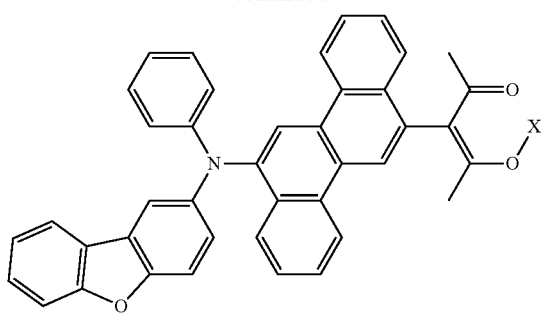
274 (X = H)
275 (X = BF$_2$)
276 (X = BMes$_2$)
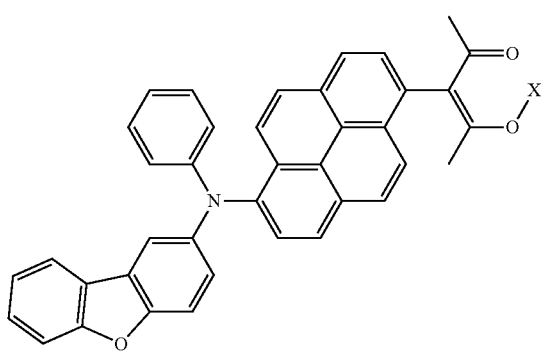
277 (X = H)
278 (X = BF$_2$)
279 (X = BMes$_2$)
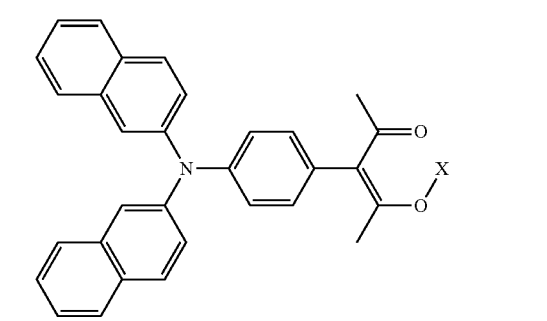
280 (X = H)
281 (X = BF$_2$)
282 (X = BMes$_2$)
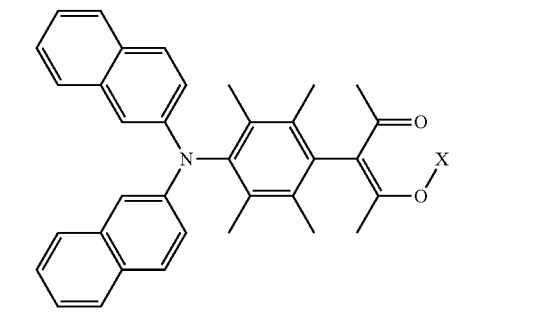
283 (X = H)
284 (X = BF$_2$)
285 (X = BMes$_2$)
-continued
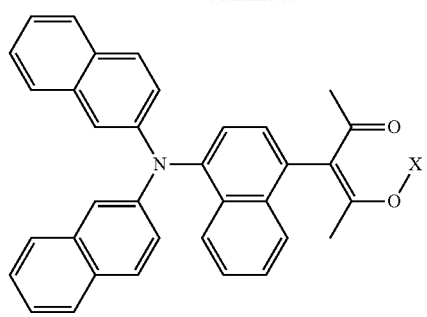
286 (X = H)
287 (X = BF$_2$)
288 (X = BMes$_2$)
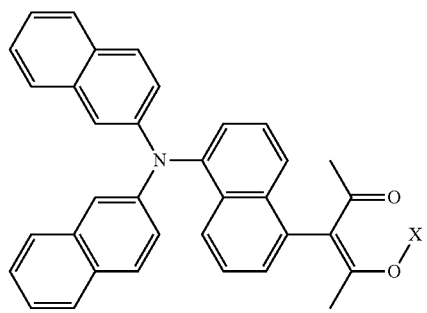
289 (X = H)
290 (X = BF$_2$)
291 (X = BMes$_2$)
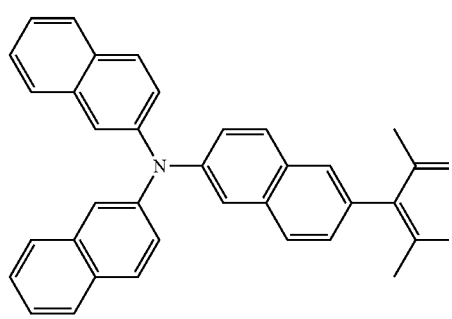
292 (X = H)
293 (X = BF$_2$)
294 (X = BMes$_2$)
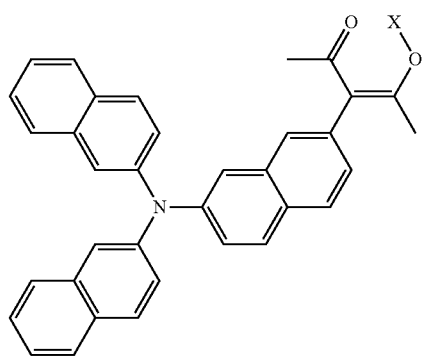
295 (X = H)
296 (X = BF$_2$)
297 (X = BMes$_2$)

-continued
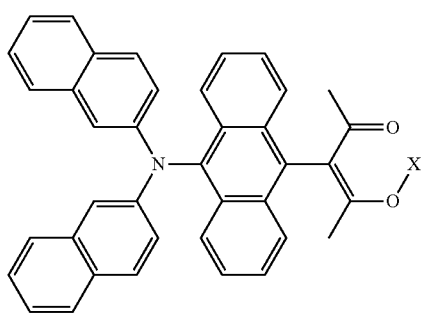
298 (X = H)
299 (X = BF₂)
300 (X = BMes₂)
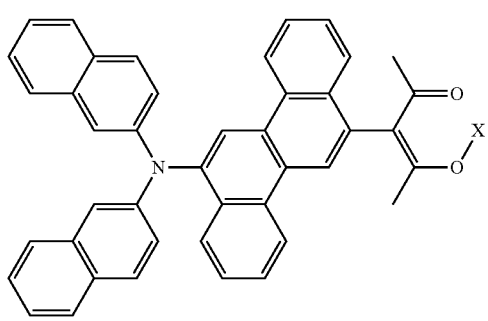
301 (X = H)
302 (X = BF₂)
303 (X = BMes₂)
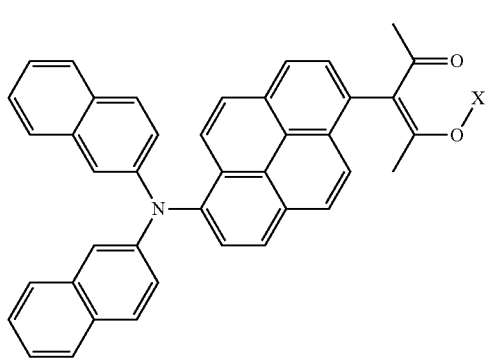
304 (X = H)
305 (X = BF₂)
306 (X = BMes₂)
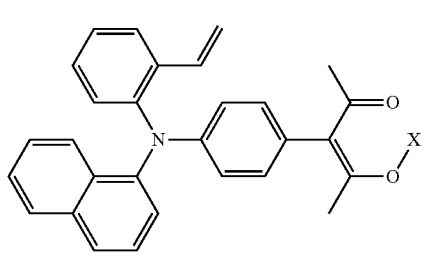
307 (X = H)
308 (X = BF₂)
309 (X = B(Mes)₂)
-continued
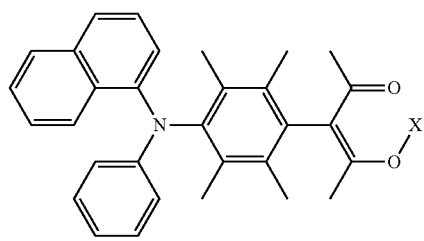
310 (X = H)
311 (X = BF₂)
312 (X = BMes₂)
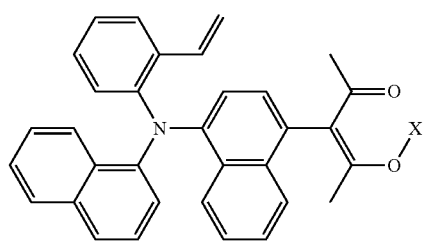
313 (X = H)
314 (X = BF₂)
315 (X = BMes₂)
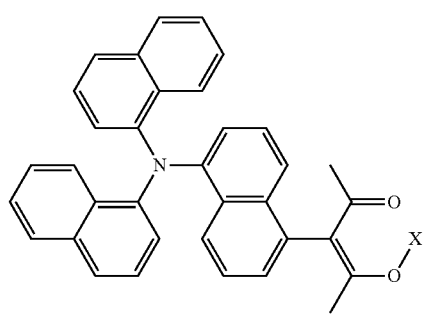
316 (X = H)
317 (X = BF₂)
318 (X = BMes₂)
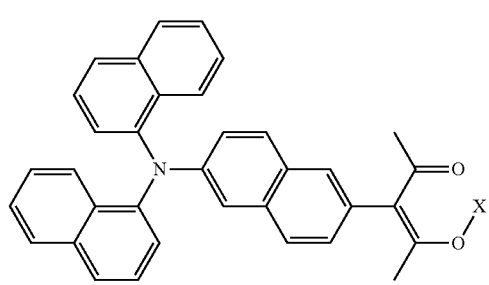
319 (X = H)
320 (X = BF₂)
321 (X = BMes₂)

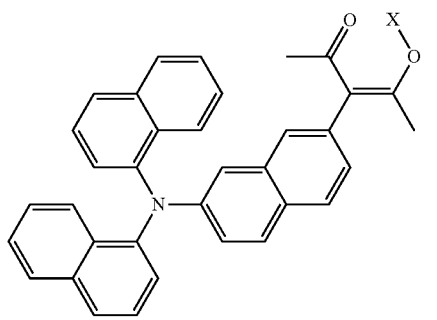
322 (X = H)
323 (X = BF₂)
324 (X = BMes₂)
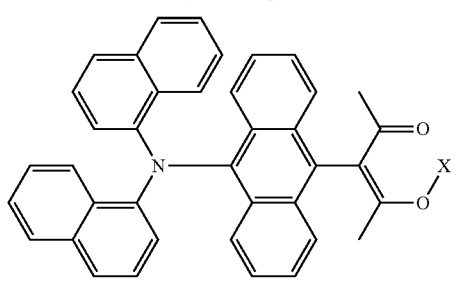
325 (X = H)
326 (X = BF₂)
327 (X = BMes₂)
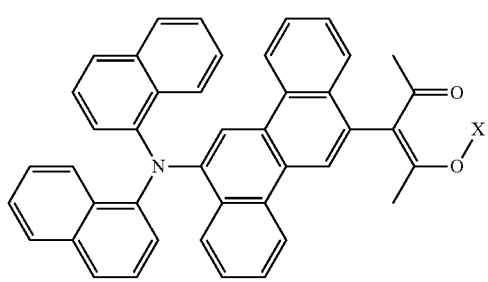
328 (X = H)
329 (X = BF₂)
330 (X = BMes₂)
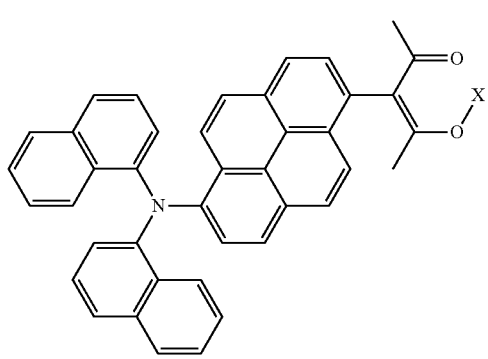
331 (X = H)
332 (X = BF₂)
333 (X = BMes₂)
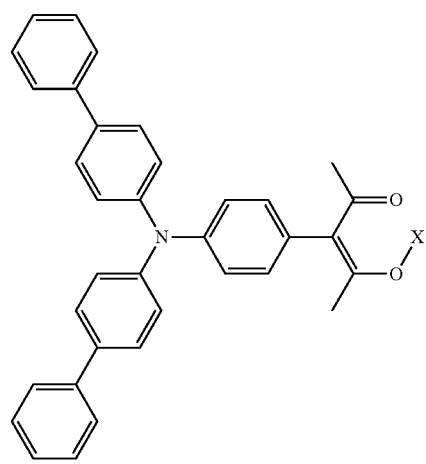
334 X = H)
335 (X = BF₂)
336 (X = BMes₂)
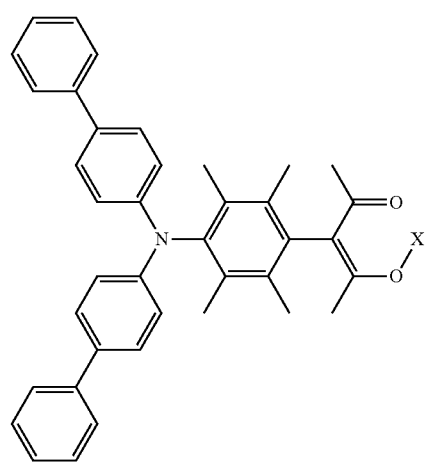
337 X = H)
338 (X = BF₂)
339 (X = BMes₂)
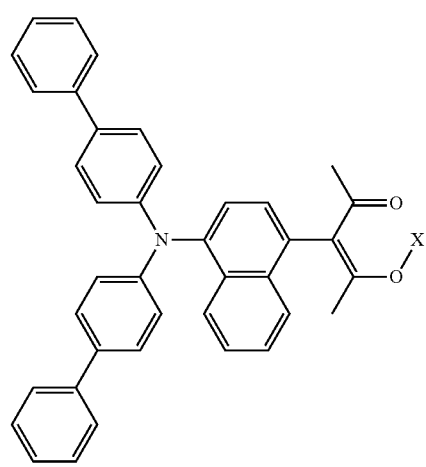
340 X = H)
341 (X = BF₂)
342 (X = BMes₂)

-continued
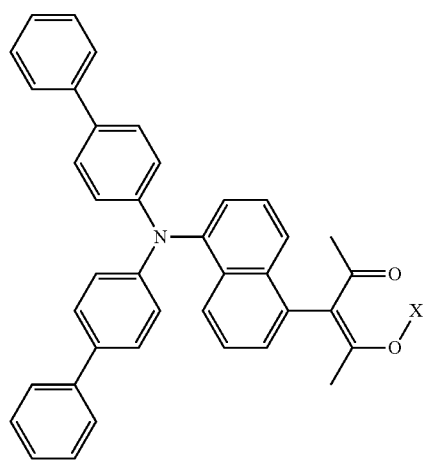
343 (X = H)
344 (X = BF₂)
345 (X = BMes₂)
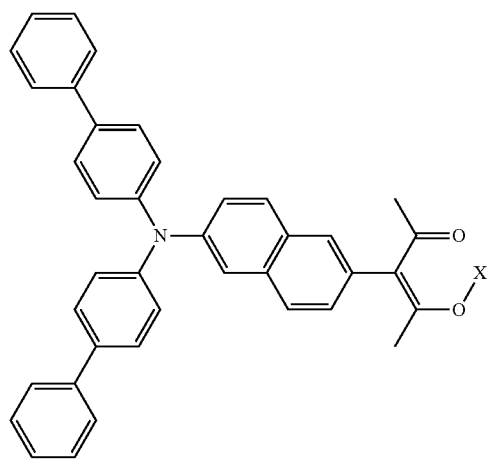
346 (X = H)
347 (X = BF₂)
348 (X = BMes₂)
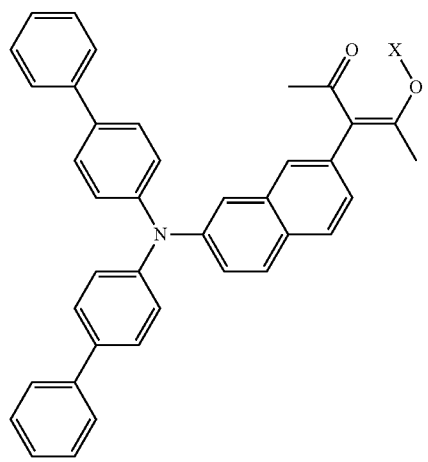
349 (X = H)
350 (X = BF₂)
351 (X = BMes₂)
-continued
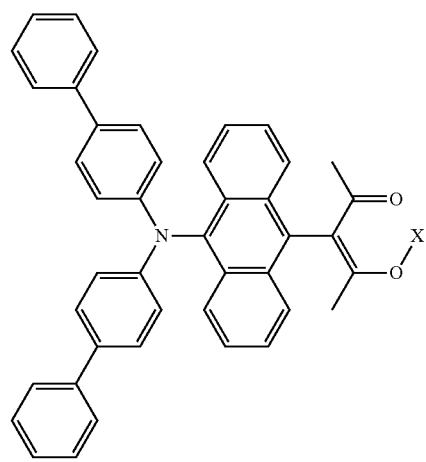
352 (X = H)
353 (X = BF₂)
354 (X = BMes₂)
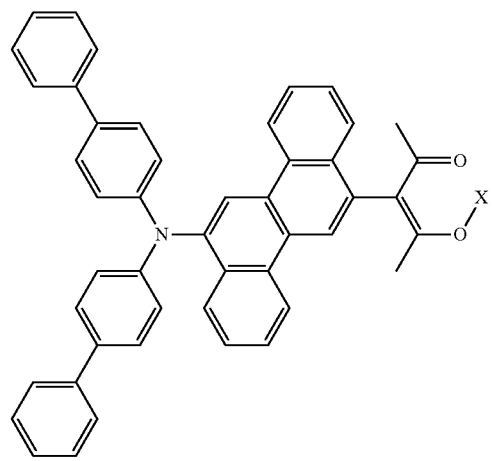
355 (X = H)
356 (X = BF₂)
357 (X = BMes₂)
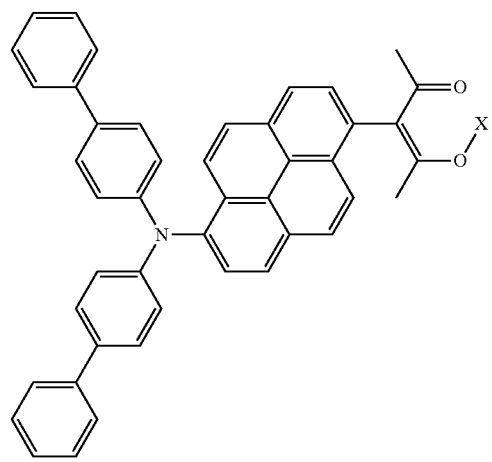
358 (X = H)
359 (X = BF₂)
360 (X = BMes₂)

-continued
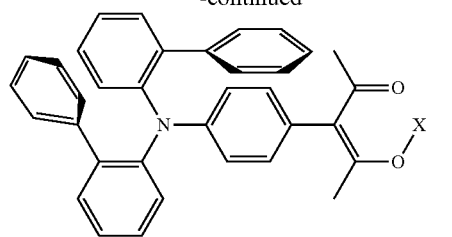
361 (X = H)
362 (X = BX₂)
363 (X = B(Ar₃)₂)
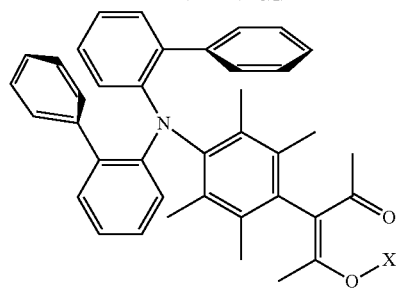
364 (X = H)
365 (X = BX₂)
366 (X = B(Ar₃)₂)
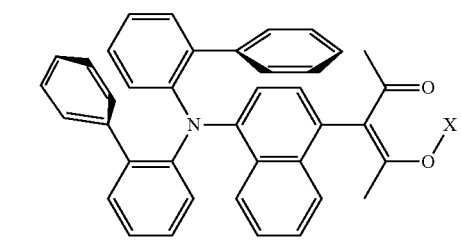
367 (X = H)
368 (X = BX₂)
369 (X = B(Ar₃)₂)
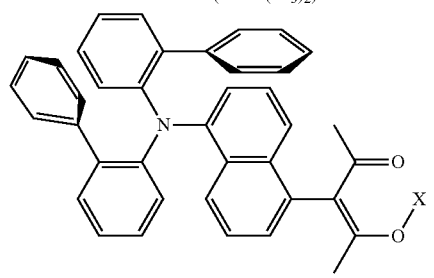
370 (X = H)
371 (X = BF₂)
372 (X = BMes₂)
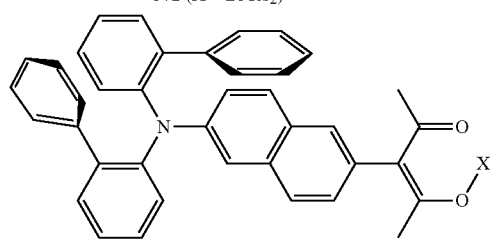
373 (X = H)
374 (X = BF₂)
375 (X = BMes₂)
-continued
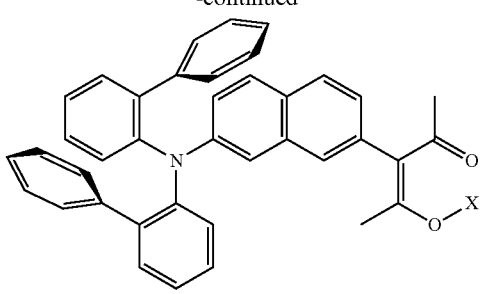
376 (X = H)
377 (X = BF₂)
378 (X = BMes₂)
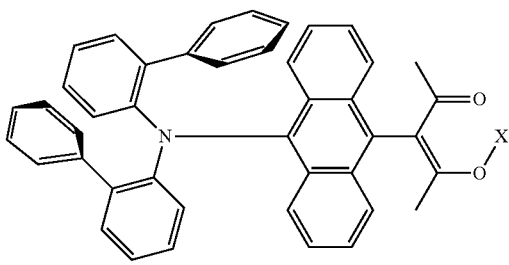
379 (X = H)
380 (X = BF₂)
381 (X = BMes₂)
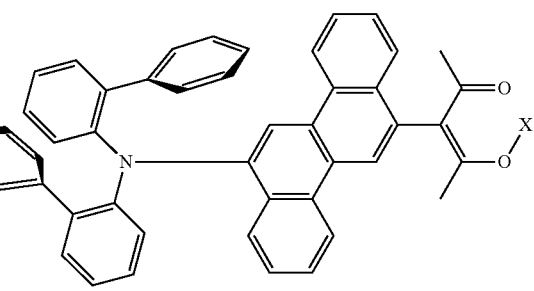
382 (X = H)
383 (X = BF₂)
384 (X = BMes₂)
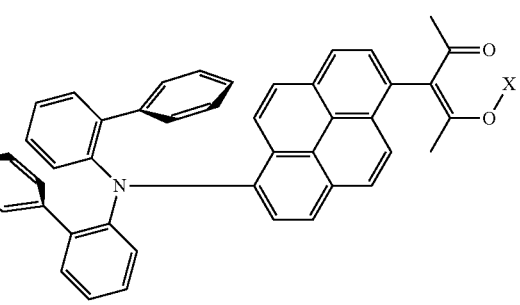
385 (X = H)
386 (X = BF₂)
387 (X = BMes₂)

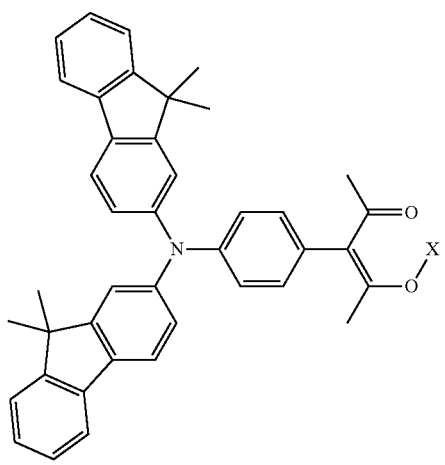
388 (X = H)
389 (X = BF₂)
390 (X = BMes₂)
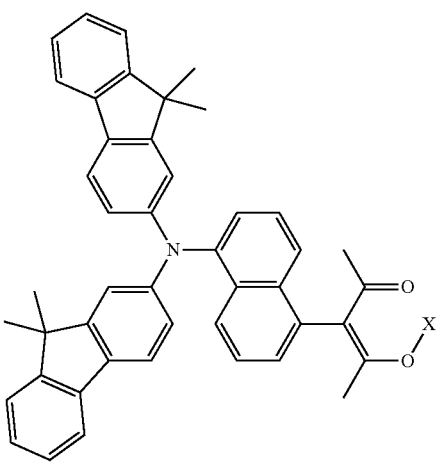
397 (X = H)
398 (X = BF₂)
399 (X = BMes₂)
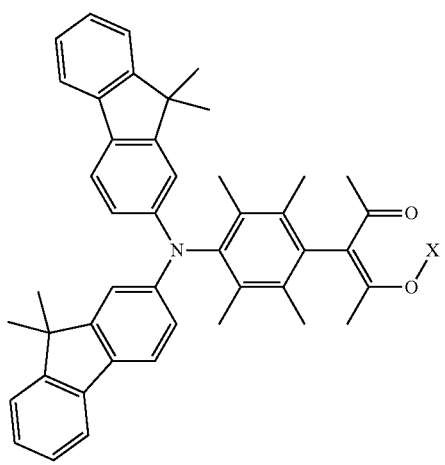
391 (X = H)
392 (X = BF₂)
393 (X = BMes₂)
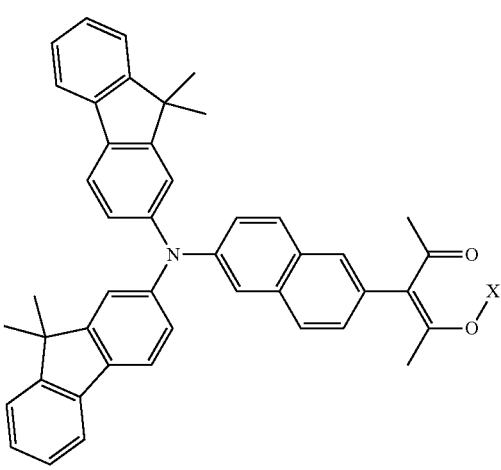
400 (X = H)
401 (X = BF₂)
402 (X = BMes₂)
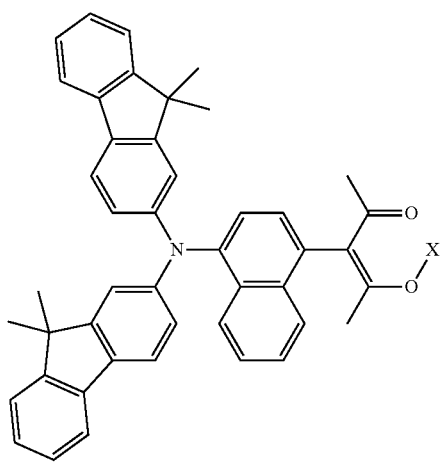
394 (X = H)
395 (X = BF₂)
396 (X = BMes₂)
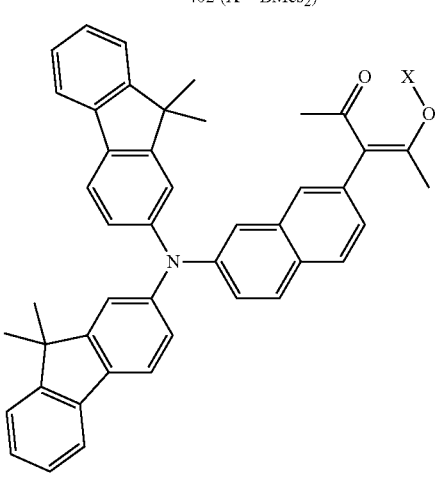
403 (X = H)
404 (X = BF₂)
405 (X = BMes₂)

-continued
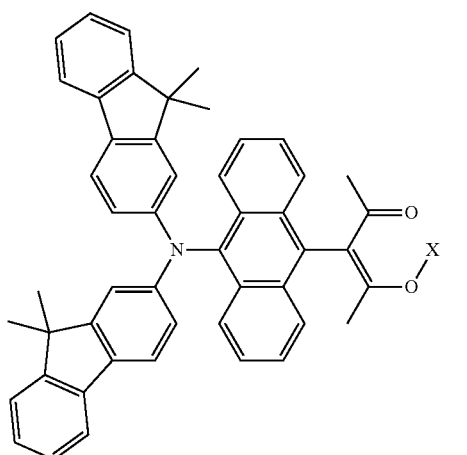
406 (X = H)
407 (X = BF₂)
408 (X = BMes₂)
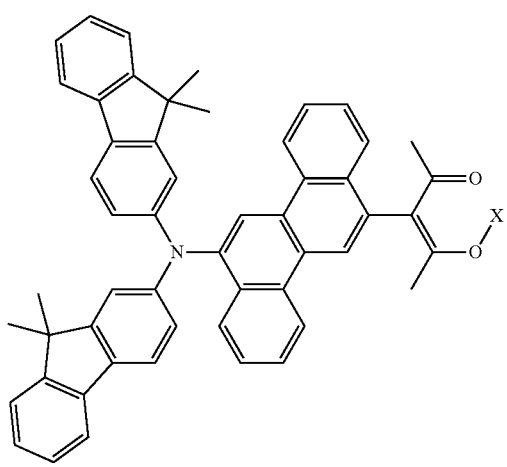
409 (X = H)
410 (X = BF₂)
411 (X = BMes₂)
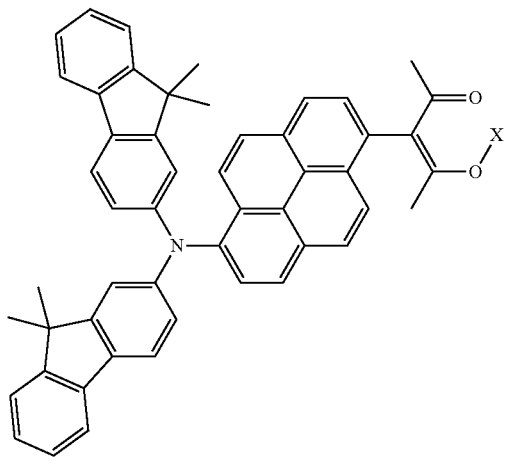
412 (X = H)
413 (X = BF₂)
414 (X = BMes₂)
-continued
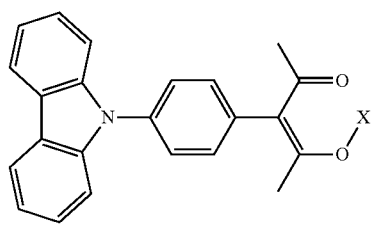
415 (X = H)
416 (X = BF₂)
417 (X = BMes₂)
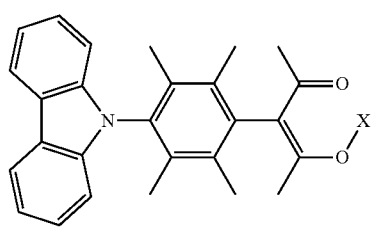
418 (X = H)
419 (X = BF₂)
420 (X = BMes₂)
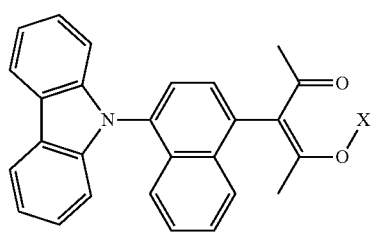
421 (X = H)
419 (X = BF₂)
420 (X = BMes₂)
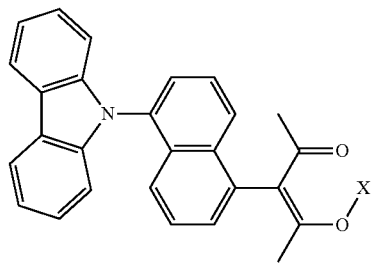
424 (X = H)
425 (X = BF₂)
426 (X = BMes₂)
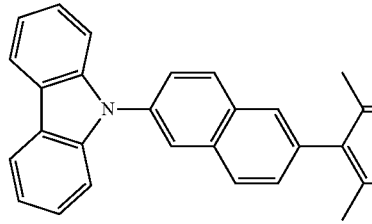
427 (X = H)
428 (X = BF₂)
429 (X = BMes₂)

-continued
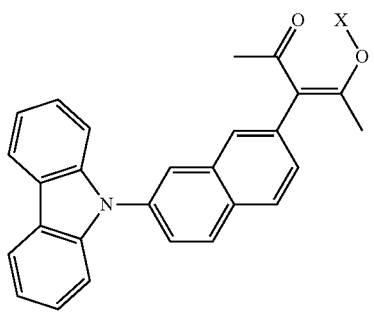
430 (X = H)
431 (X = BF₂)
432 (X = BMes₂)
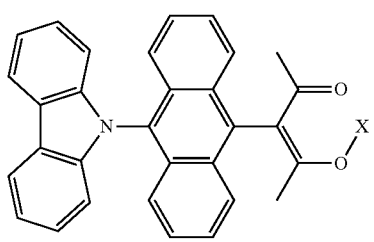
433 (X = H)
434 (X = BF₂)
435 (X = BMes₂)
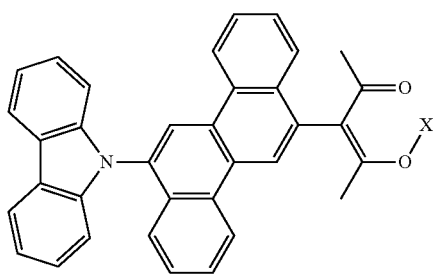
436 (X = H)
437 (X = BF₂)
438 (X = BMes₂)
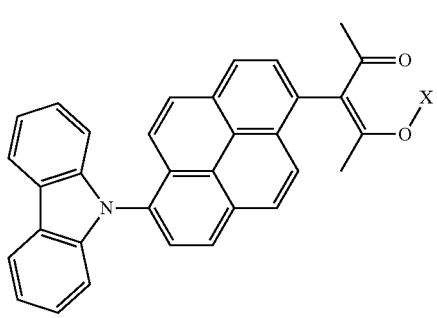
439 (X = H)
440 (X = BF₂)
441 (X = BMes₂)
-continued
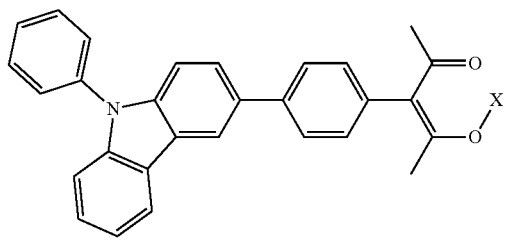
442 (X = H)
443 (X = BF₂)
444 (X = BMes₂)
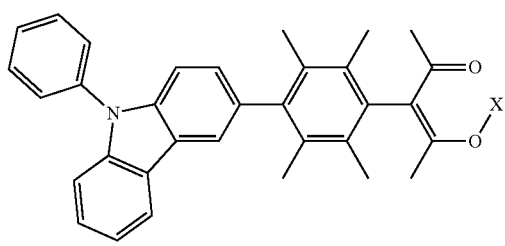
445 (X = H)
446 (X = BF₂)
447 (X = BMes₂)
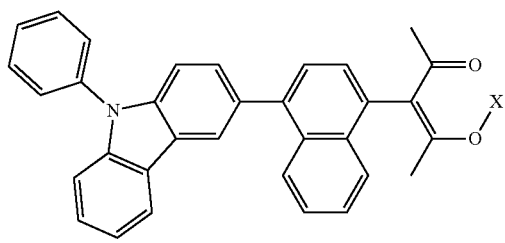
448 (X = H)
449 (X = BF₂)
450 (X = BMes₂)
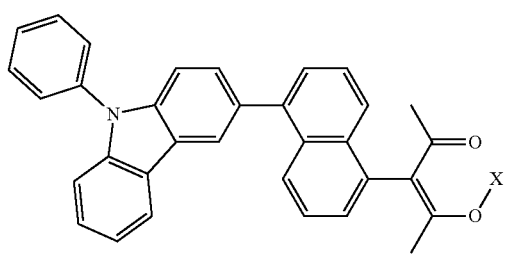
451 (X = H)
452 (X = BF₂)
453 (X = BMes₂)
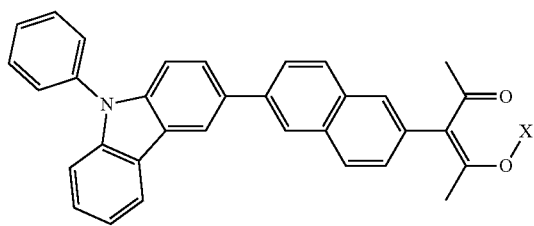
454 (X = H)
455 (X = BF₂)
456 (X = BMes₂)

-continued
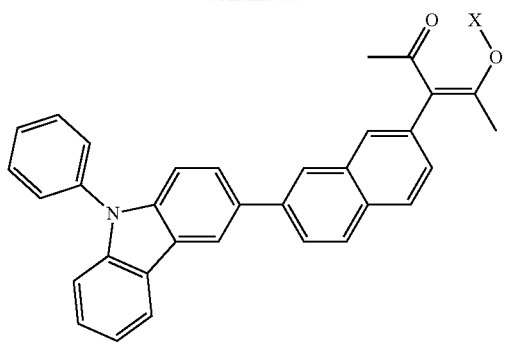
457 (X = H)
458 (X = BF₂)
459 (X = BMes₂)
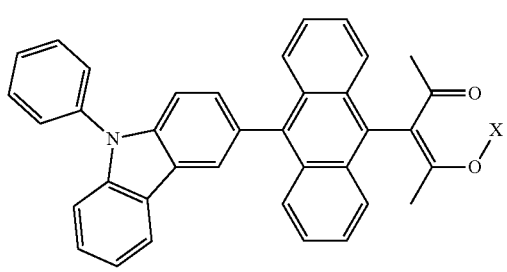
460 (X = H)
461 (X = BF₂)
462 (X = BMes₂)
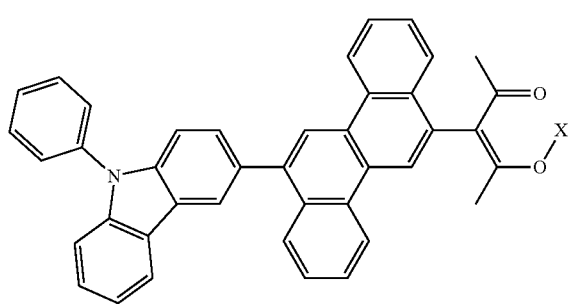
463 (X = H)
464 (X = BF₂)
465 (X = BMes₂)
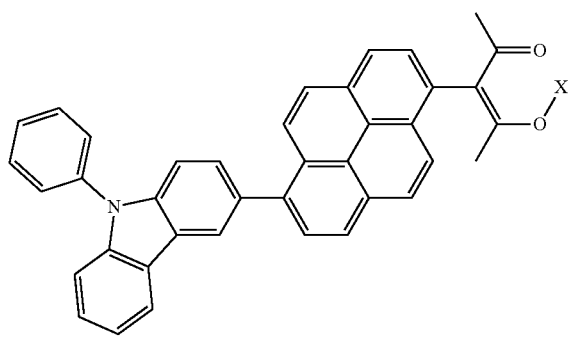
466 (X = H)
467 (X = BF₂)
468 (X = BMes₂)
-continued
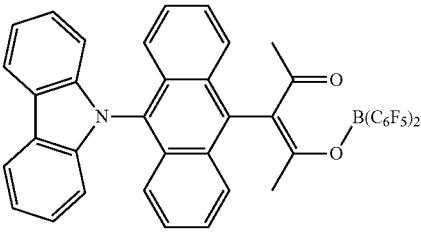
469
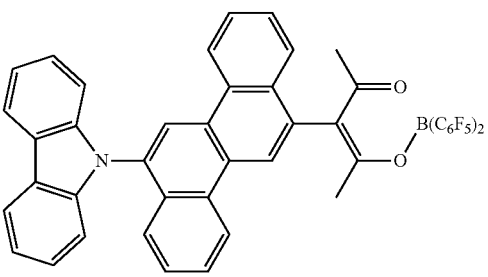
470
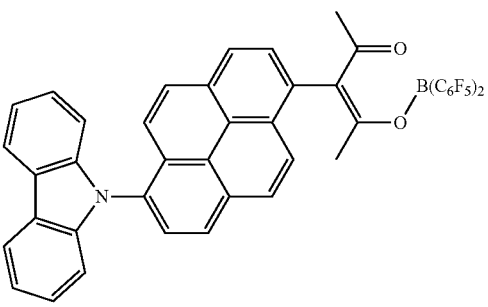
471
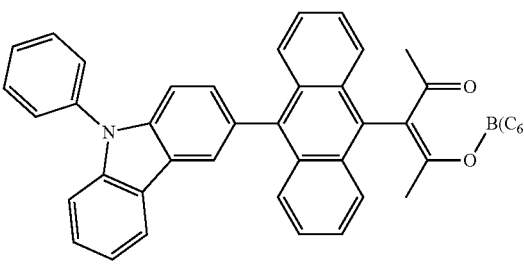
472
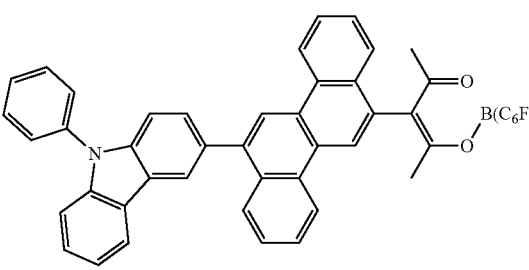
473

-continued

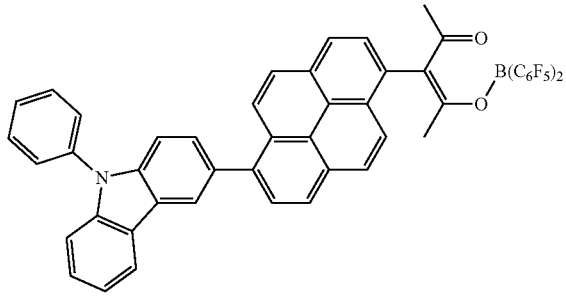

474

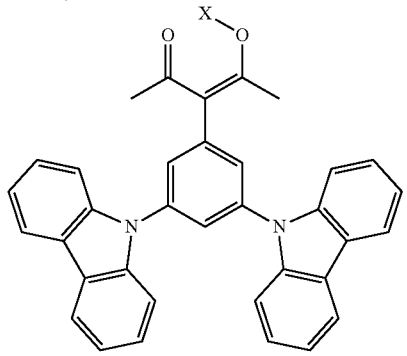

475 (X = H)
476 (X = BF$_2$)
477 (X = BMes$_2$)
478 (B(C$_6$F$_5$)$_2$)

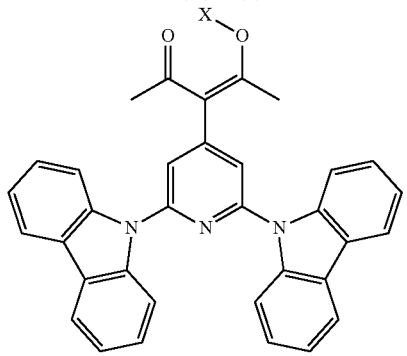

479 (X = H)
480 (X = BF$_2$)
481 (X = BMes$_2$)
482 (B(C$_6$F$_5$)$_2$)

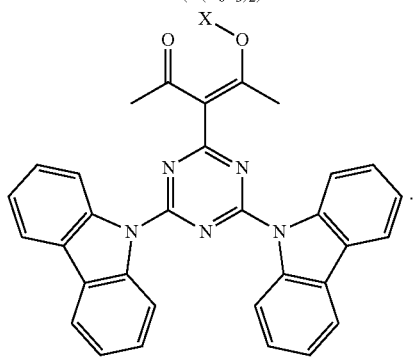

483 (X = H)
484 (X = BF$_2$)
485 (X = BMes$_2$)
486 (B(C$_6$F$_5$)$_2$)

The term "organic layer" used herein refers to a single layer and/or a plurality of layers disposed between the first electrode and the second electrode of an organic light-emitting device. A material included in the "organic layer" is not limited to an organic material.

FIG. 1 is a schematic view of an organic light-emitting device 10 according to an embodiment. The organic light-emitting device 10 includes a first electrode 110, an organic layer 150, and a second electrode 190.

Hereinafter, the structure of an organic light-emitting device according to an embodiment and a method of manufacturing an organic light-emitting device according to an embodiment will be described in connection with FIG. 1.

In FIG. 1, a substrate (not shown) may be disposed under the first electrode 110 or above the second electrode 190. The substrate may be a glass substrate or a transparent plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for forming the first electrode 110 may be selected from materials with a high work function to facilitate hole injection. The first electrode 110 may be a reflective electrode, a semi-transmissive electrode, or a transmissive electrode. The material for forming the first electrode 110 may be a transparent and highly conductive material, and examples of such a material are indium tin oxide (ITO), indium zinc oxide (IZO), tin oxide (SnO$_2$), and zinc oxide (ZnO). When the first electrode 110 is a semi-transmissive electrode or a reflective electrode, at least one selected from magnesium (Mg), aluminum (Al), aluminum-lithium (Al—Li), calcium (Ca), magnesium-indium (Mg—In), and magnesium-silver (Mg—Ag) may be used as a material for forming the first electrode 110.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

In one or more embodiments, the hole transport region may include at least one selected from a hole transport layer, a hole injection layer, a buffer layer, and an electron blocking layer, and an electron transport region may include at least one selected from a hole blocking layer, an electron transport layer, and an electron injection layer. However, it may be understood that embodiments of the present disclosure are not limited thereto.

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a hole injection layer/hole transport layer structure, a hole injection layer/hole transport layer/buffer layer structure, a hole injection layer/buffer layer structure, a hole transport layer/buffer layer structure, or a hole injection layer/hole transport layer/electron blocking layer structure, wherein layers of each structure are sequentially stacked from the first electrode 110 in this stated order, but are not limited thereto.

When the hole transport region includes a hole injection layer, the hole injection layer may be formed on the first electrode 110 by using one or more suitable methods selected from vacuum deposition, spin coating, casting, Langmuir-Blodgett (LB) deposition, ink-jet printing, laser-printing, and laser-induced thermal imaging.

When the hole injection layer is formed by vacuum deposition, the vacuum deposition may be performed at, for example, a deposition temperature of about 100° C. to about 500° C. at a vacuum degree of about $10^{-8}$ torr to about $10^{-3}$ torr, and a deposition rate of about 0.01 Å/sec to about 100 Å/sec by taking into account a compound to be deposited on a hole injection layer, and the structure of a hole injection layer to be formed.

When a hole injection layer is formed by spin coating, the spin coating may be performed at a coating rate of about 2,000 rpm to about 5,000 rpm, and at a temperature of about 80° C. to 200° C. by taking into account the compound for the hole injection layer to be deposited, and the structure of the hole injection layer to be formed.

When the hole transport region includes a hole transport layer, the hole transport layer may be formed on the first electrode 110 or the hole injection layer by using one or more suitable methods selected from vacuum deposition, spin coating, casting, a LB method, ink-jet printing, laser-printing, and laser-induced thermal imaging. When the hole transport layer is formed by vacuum deposition or spin coating, deposition and coating conditions for the hole transport layer may be the same as the deposition and coating conditions for the hole injection layer.

The hole transport region may include m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonicacid (PANI/CSA), polyaniline/poly(4-styrenesulfonate) (PANI/PSS), a compound represented by Formula 201 below, or a compound represented by Formula 202 below:

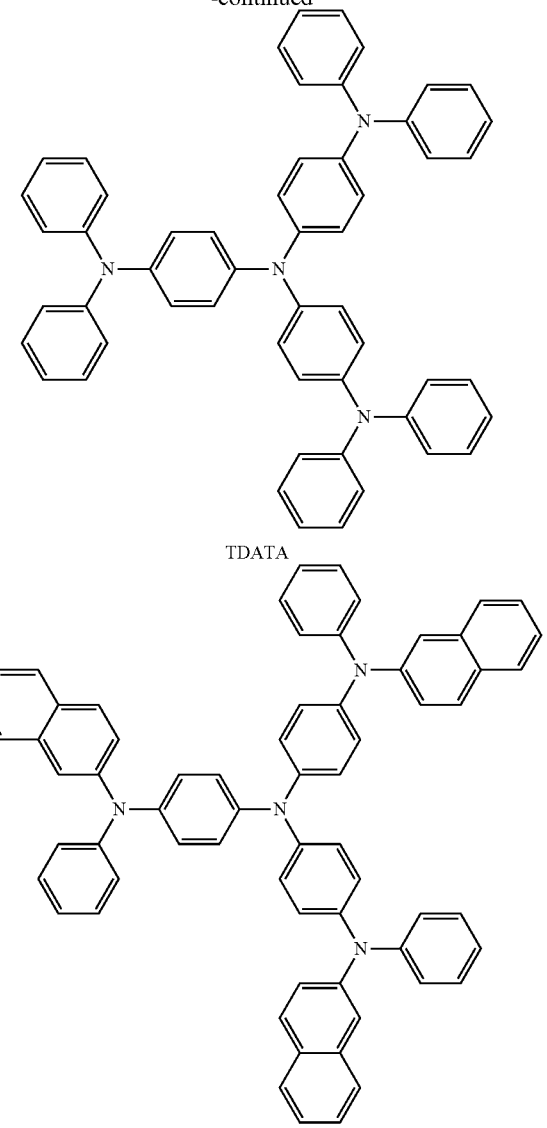

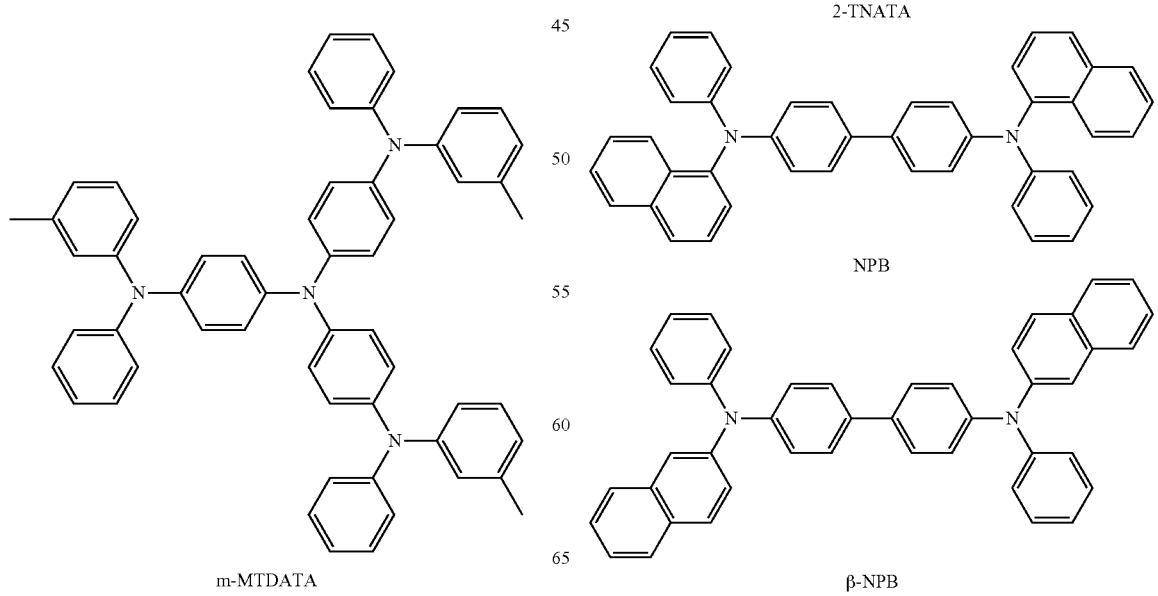

-continued

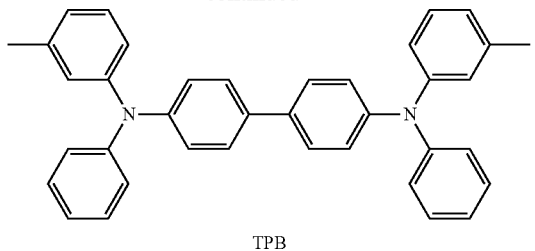

TPB

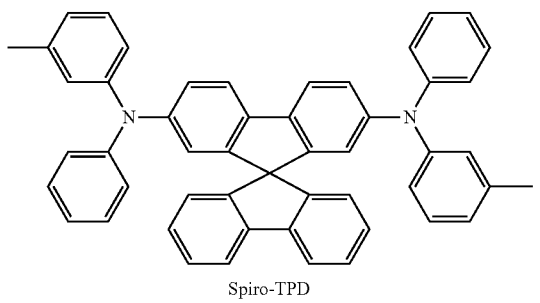

Spiro-TPD

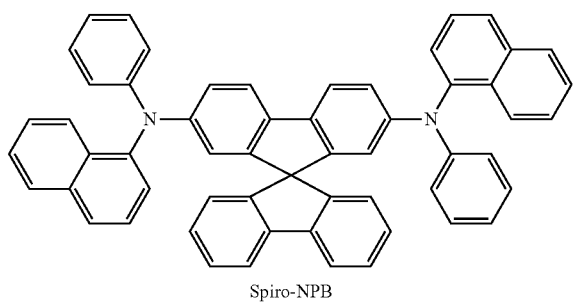

Spiro-NPB

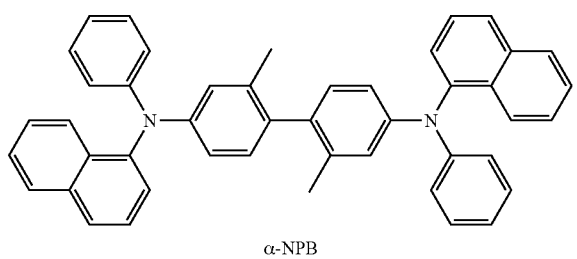

α-NPB

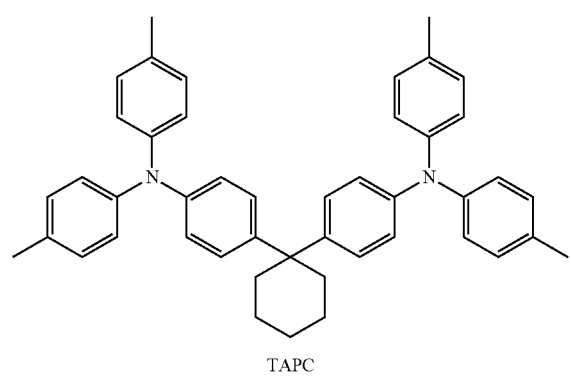

TAPC

-continued

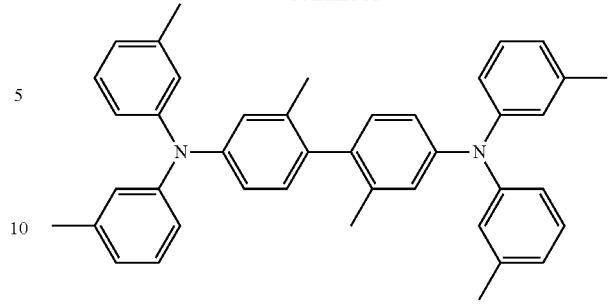

HMTPD

<Formula 201>

$$R_{201}\!-\!(L_{201})_{xa1}\!-\!N\!\!\begin{array}{c}(L_{202})_{xa2}\!-\!R_{202}\\ (L_{203})_{xa3}\!-\!R_{203}\end{array}$$

<Formula 202>

$$\begin{array}{cc}R_{201}\!-\!(L_{201})_{xa1}&(L_{203})_{xa3}\!-\!R_{203}\\ \diagdown N\!-\!(L_{205})_{xa5}\!-\!N\diagup\\ R_{202}\!-\!(L_{202})_{xa2}&(L_{204})_{xa4}\!-\!R_{204}.\end{array}$$

In Formulae 201 and 202, $L_{201}$ to $L_{205}$ may each independently be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xa1 to xa4 may each independently be selected from 0, 1, 2, and 3;

xa5 may be selected from 1, 2, 3, 4, and 5; and $R_{201}$ to $R_{204}$ may each independently be selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arythio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one or more embodiments, in Formulae 201 and 202, $L_{201}$ to $L_{205}$ may each independently be selected from:

a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may each independently be 0, 1, or 2, xa5 may be 1, 2, or 3, and $R_{201}$ to $R_{204}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments of the present disclosure are not limited thereto.

The compound represented by Formula 201 may be represented by Formula 201A:

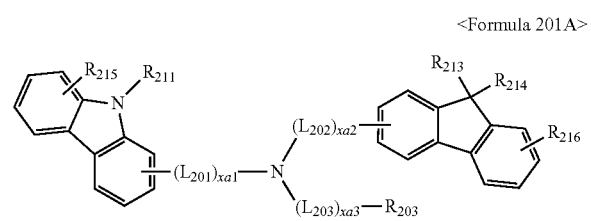

<Formula 201A>

In one embodiment, the compound represented by Formula 201 may be represented by Formula 201A-1 below, but embodiments of the present disclosure are not limited thereto:

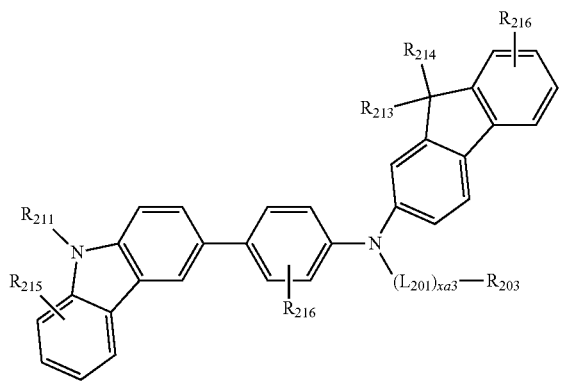

<Formula 201A-1>

For example, the compound represented by Formula 202 may be represented by Formula 202A below, but embodiments of the present disclosure are not limited thereto:

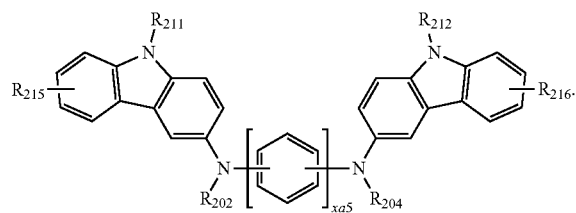

<Formula 202A>

$L_{201}$ to $L_{203}$, xa1 to xa3, xa5, and $R_{202}$ to $R_{204}$ in Formulae 201A, 201A-1 and 202A are already described in detail above, and $R_{211}$ may be understood by referring to the description provided herein in connection with $R_{203}$, and $R_{213}$ to $R_{216}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

For example, in Formulae 201A, 201A-1, and 202A, $L_{201}$ to $L_{203}$ may each independently be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, xa1 to xa3 may each independently be 0 or 1, $R_{203}$, $R_{211}$, and $R_{212}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may each independently be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and $R_{215}$ and $R_{216}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group, and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be 1 or 2.

$R_{213}$ and $R_{214}$ in Formulae 201A, and 201A-1 may be linked to each other to form a saturated or unsaturated ring.

The compound represented by Formula 201, and the compound represented by Formula 202 may each include compounds HT1 to HT20 illustrated below, but are not limited thereto:

HT1

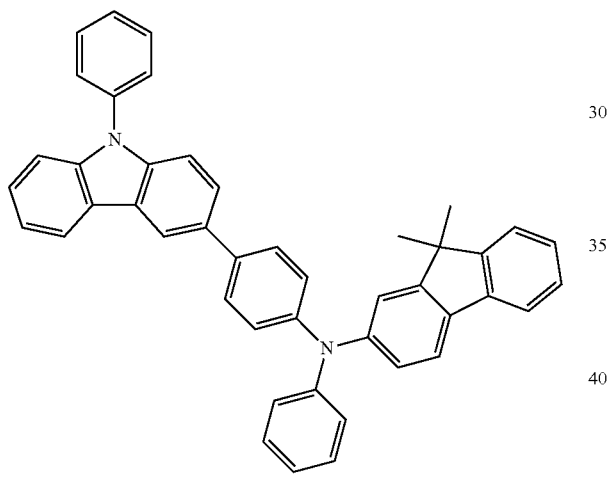

HT2

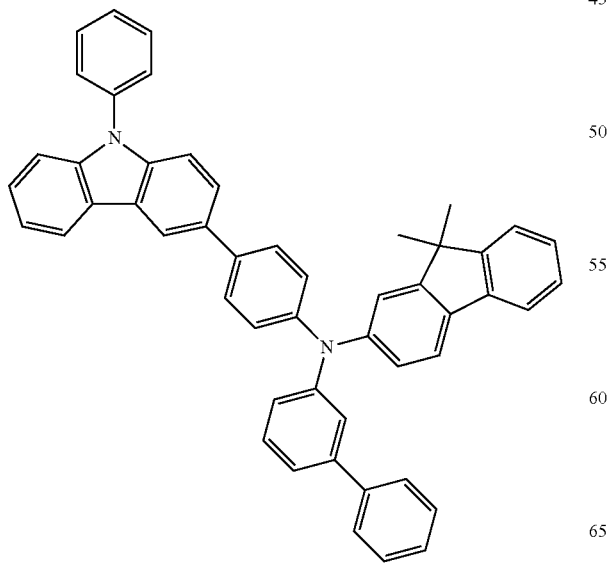

HT3

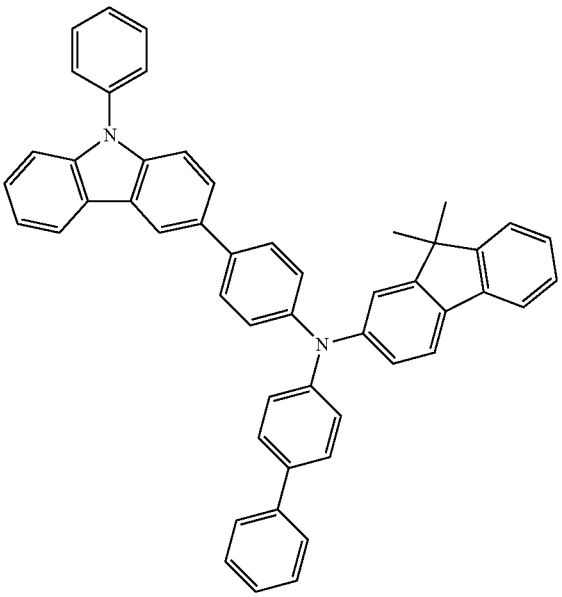

HT4

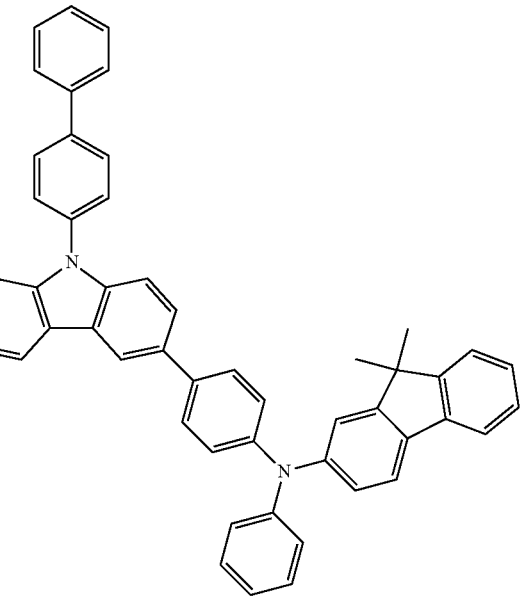

HT5
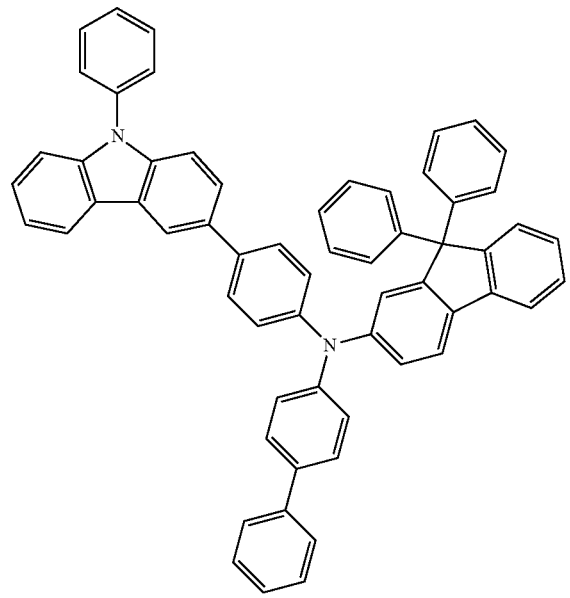
HT6
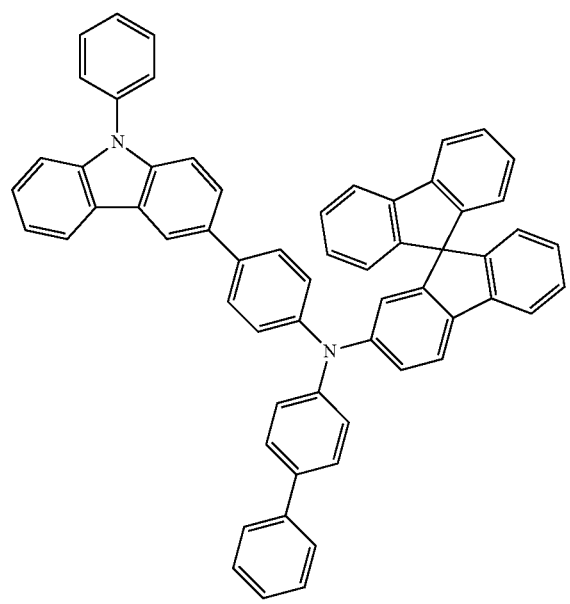
HT7
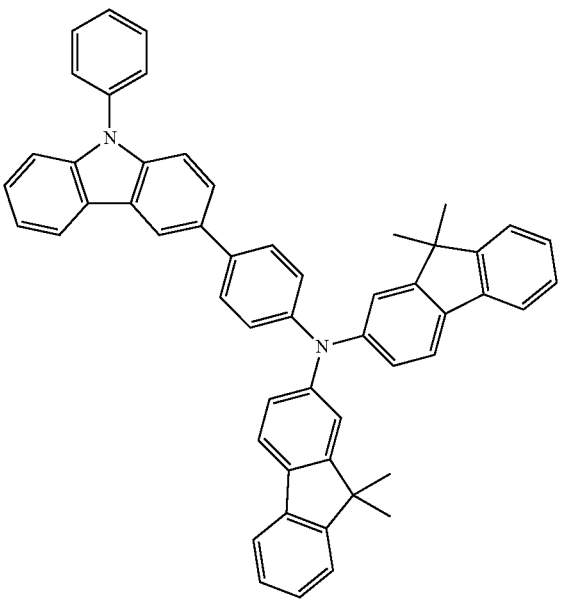
HT8
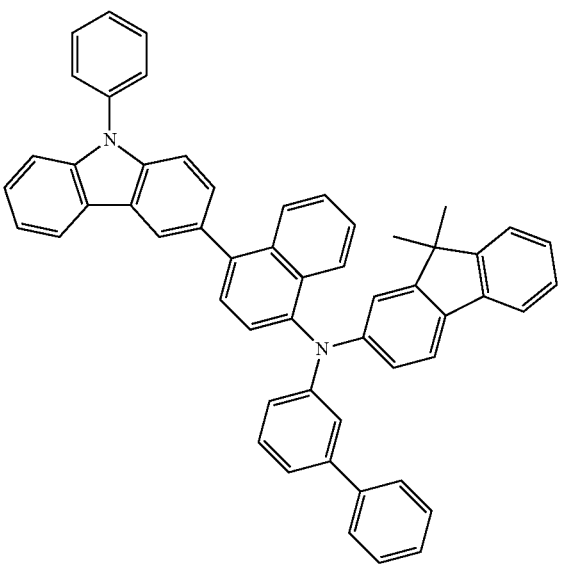

HT9
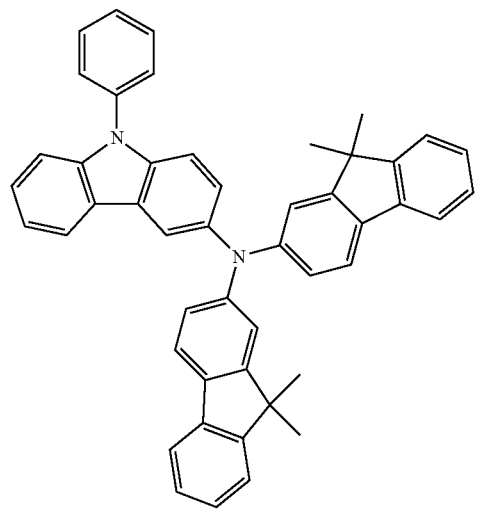
HT11
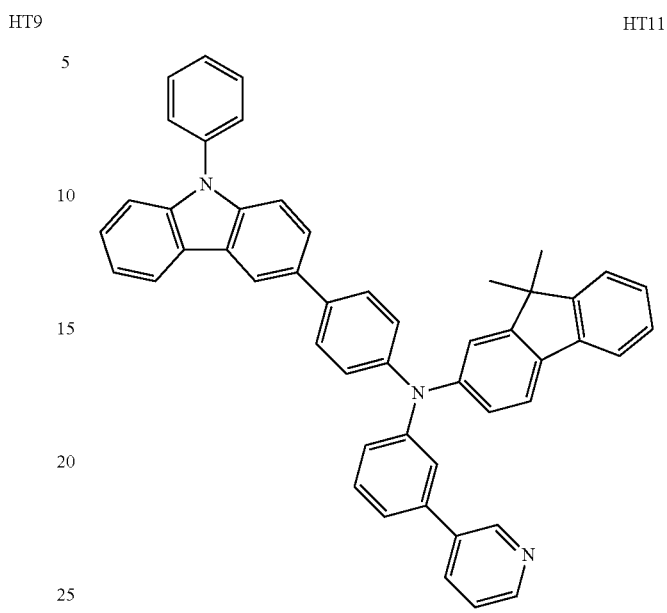
HT12
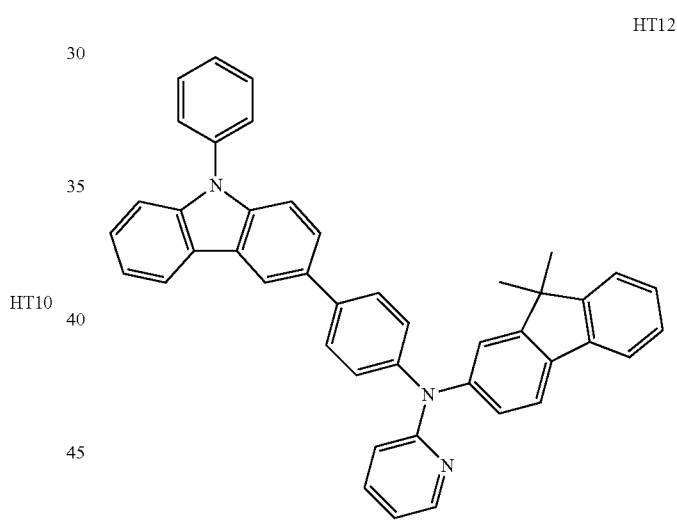
HT10
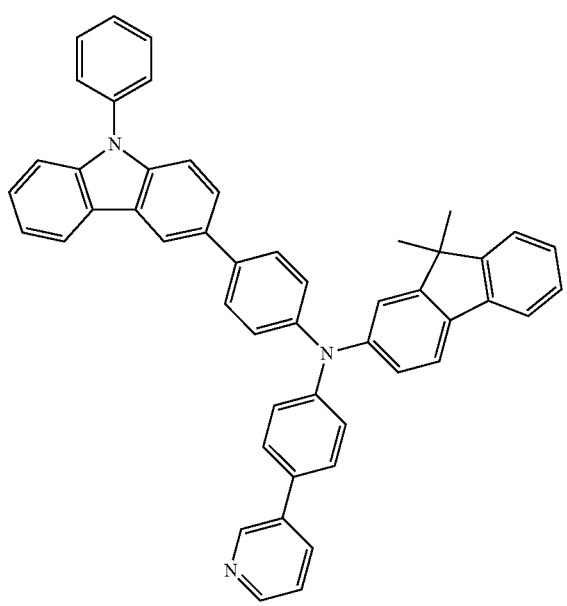
HT13
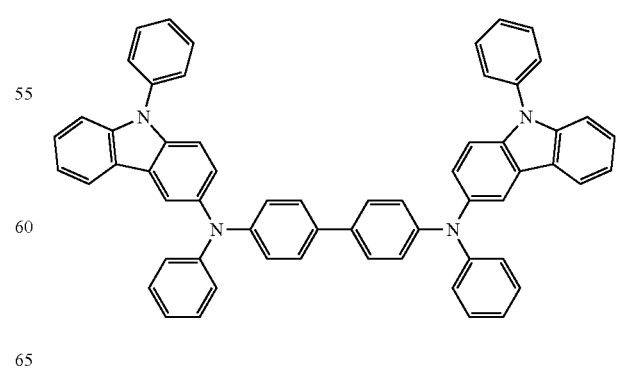

HT14
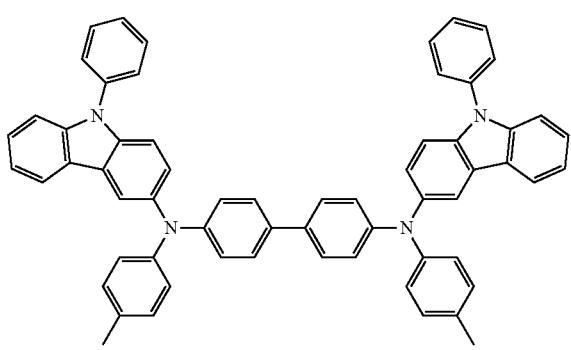

HT18
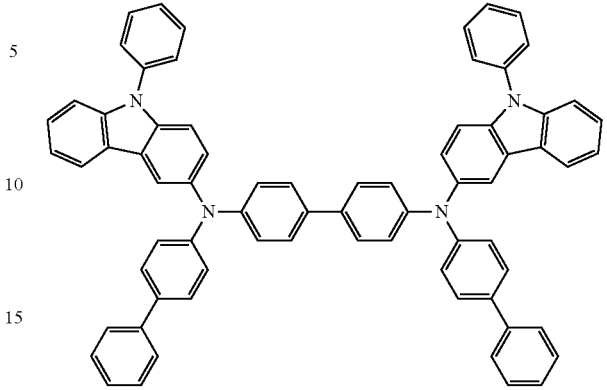

HT15
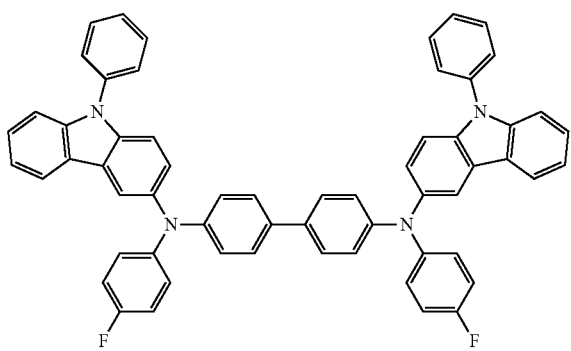

HT19
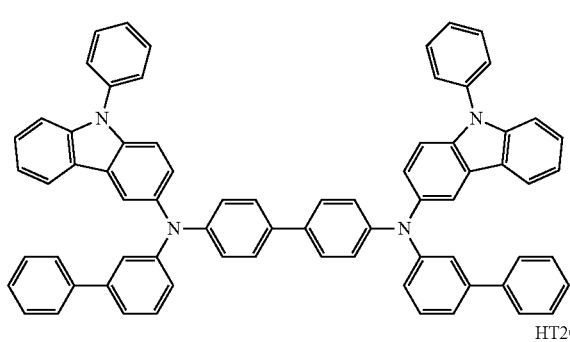

HT16
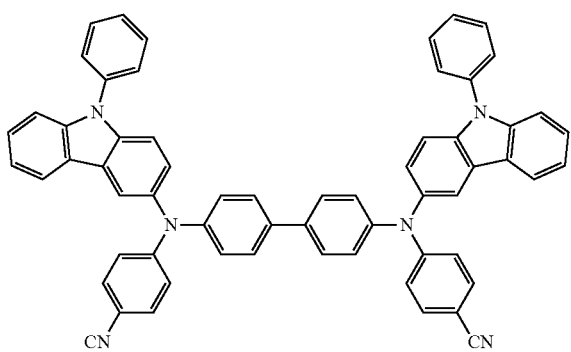

HT20
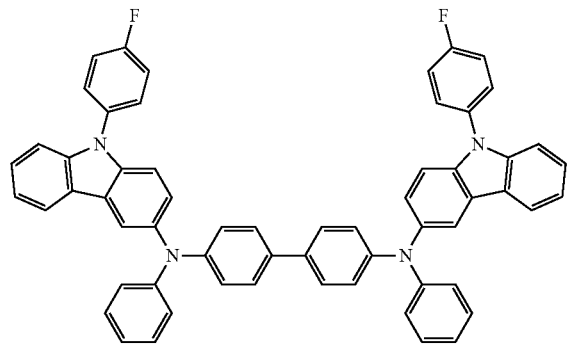

HT17
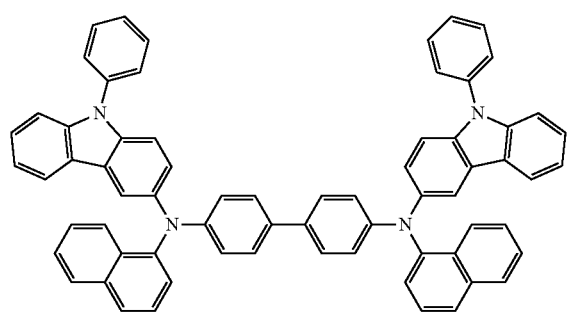

A thickness of the hole transport region may be in a range of about 100 Å to about 10,000 Å, for example, about 100 Å to about 1,000 Å When the hole transport region includes a hole injection layer and a hole transport layer, the thickness of the hole injection layer may be in a range of about 100 Å to about 10,000 Å, for example, about 100 Å to about 1,000 Å, and the thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for improving conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below, but are not limited thereto.

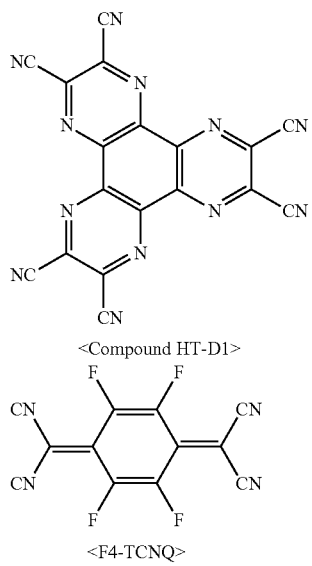

The hole transport region may further include a buffer layer, in addition to an electron blocking layer, a hole injection layer, and a hole transport layer. Since the buffer layer may compensate for an optical resonance distance according to a wavelength of light emitted from the emission layer, light-emission efficiency of a formed organic light-emitting device may be improved. For use as a material included in the buffer layer, materials that are to be included in the hole transport region may be used. The electron blocking layer prevents injection of electrons from the electron transport region.

An emission layer is formed on the first electrode 110 or the hole transport region by using one or more suitable methods selected from vacuum deposition, spin coating, casting, a LB method, ink-jet printing, laser-printing, and laser-induced thermal imaging. When an emission layer is formed by vacuum deposition or spin coating, deposition and coating conditions for the emission layer may be the same as those for the hole injection layer.

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure including a red emission layer, a green emission layer, and a blue emission layer, or may include a red light-emitting material, a green light-emitting material, and a blue light-emitting material, which are mixed with each other in a single layer, to emit white light.

The emission layer may include a host and a dopant.

For example, the host may include at least one selected from TPBi, TBADN, ADN (also referred to as "DNA"), CBP, CDBP, and TCP:

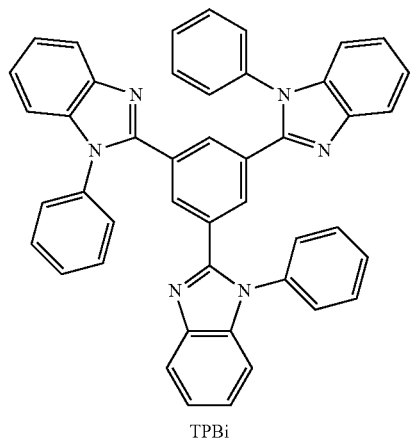

TPBi

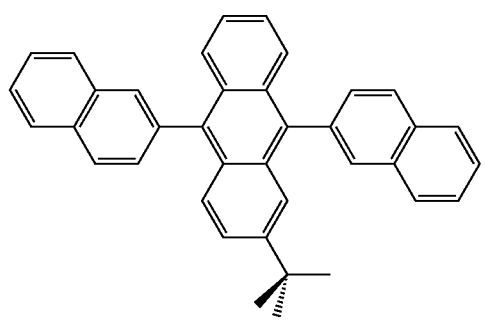

TBADN

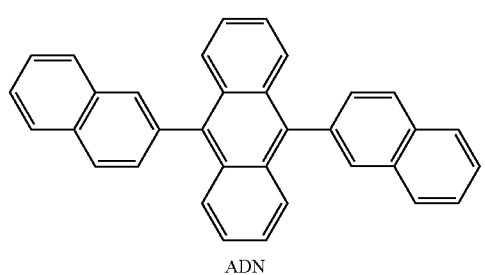

ADN

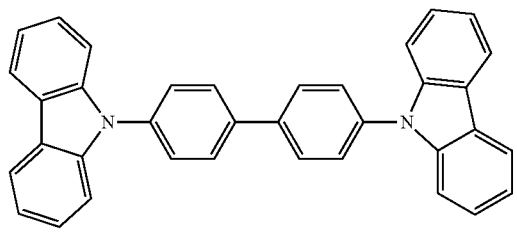

CBP

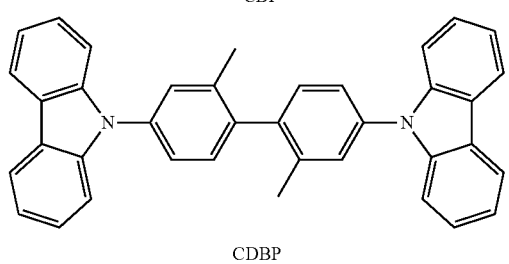

CDBP

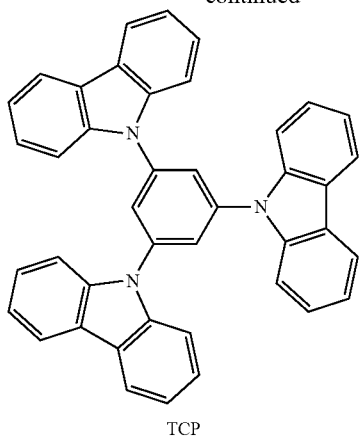

TCP

In one or more embodiments, the host may include a compound represented by Formula 301 below.

$Ar_{301}-[(L_{301})_{xb1}-R_{301}]_{xb2}$ <Formula 301>

In Formula 301, $Ar_{301}$ may be selected from:

a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylenev, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) ($Q_{301}$ to $Q_{303}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

$L_{301}$ may be selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

$R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xb1 may be selected from 0, 1, 2, and 3, and xb2 may be selected from 1, 2, 3, and 4.

For example, in Formula 301, $L_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but embodiments of the present disclosure are not limited thereto.

For example, the host may include a compound represented by Formula 301A below:

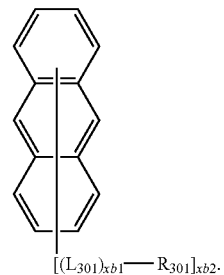
<Formula 301A>

Substituents of Formula 301A may be understood by referring to the descriptions provided herein.

The compound represented by Formula 301 may include at least one of Compounds H1 to H42, but embodiments of the present disclosure are not limited thereto:

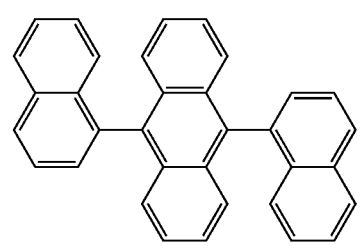
H1

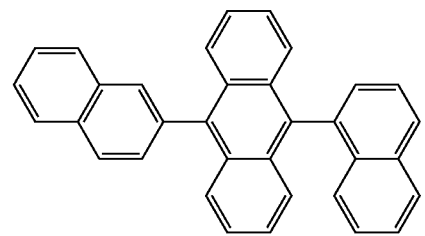
H2

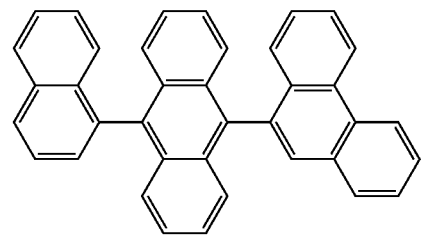
H3

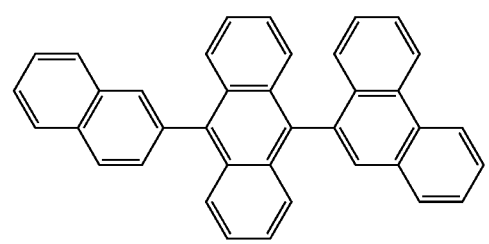
H4

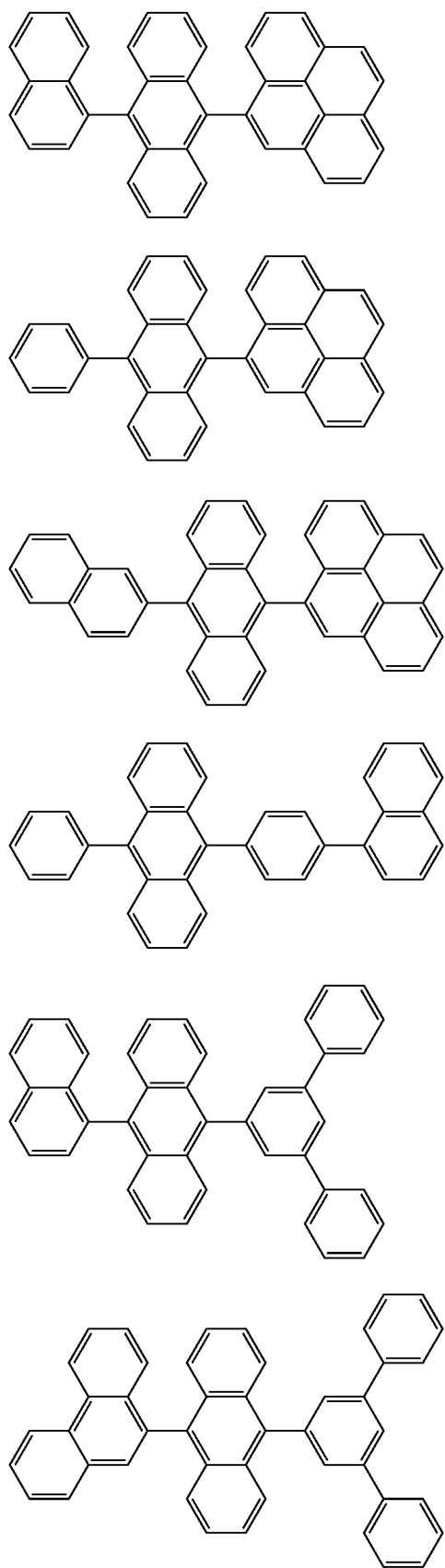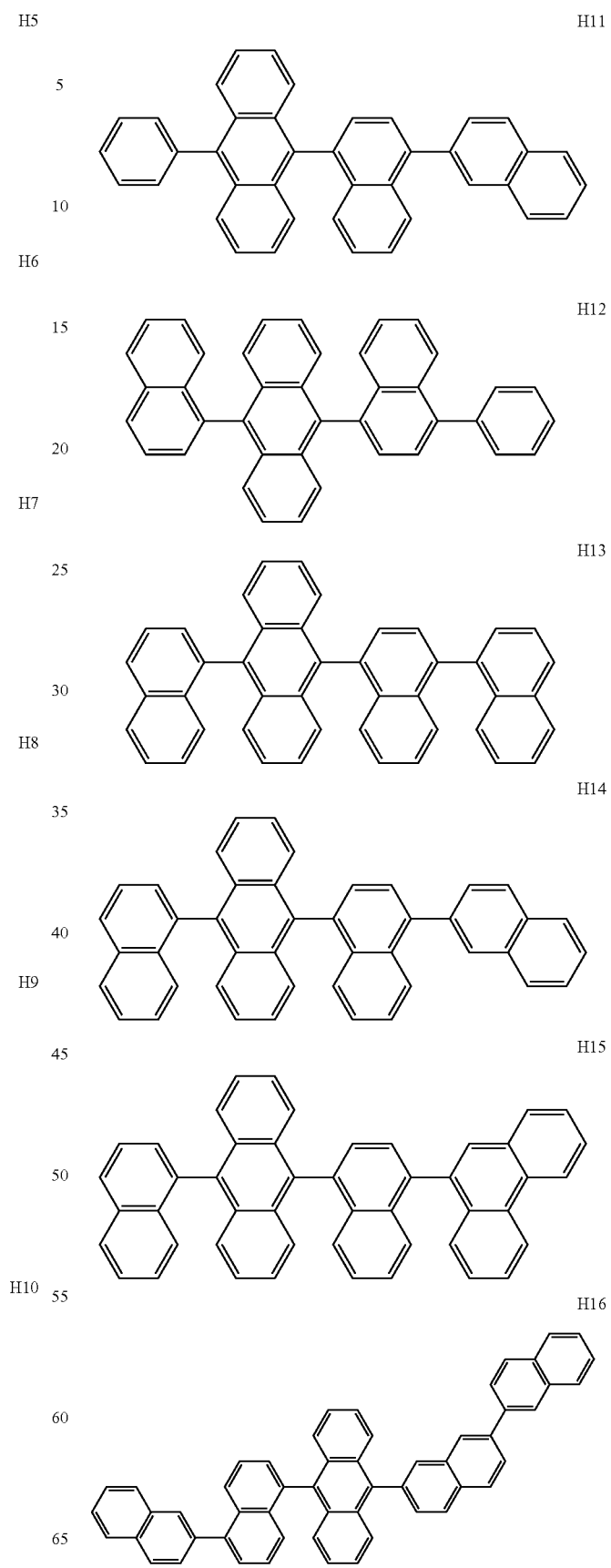

H17
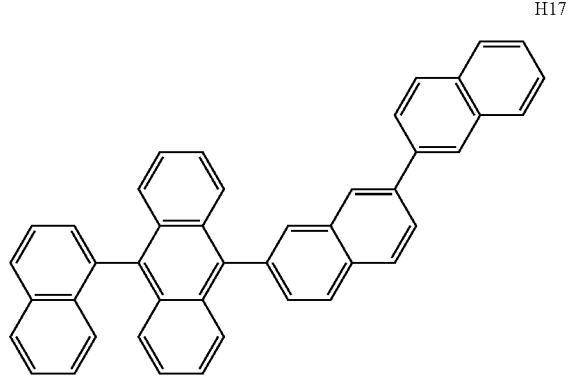
H18
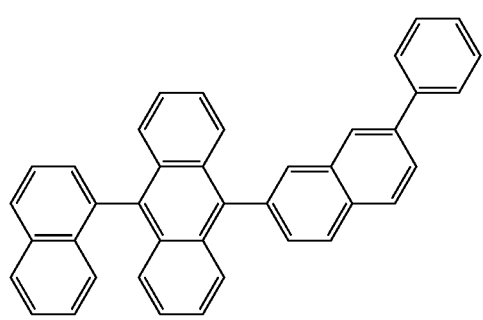
H19
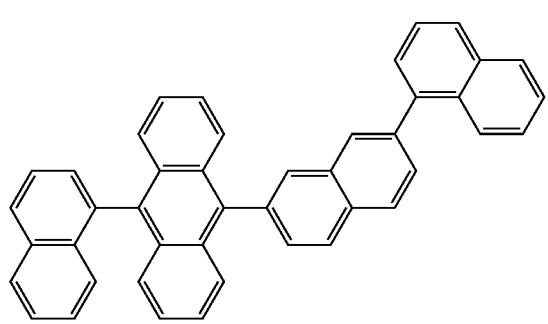
H20
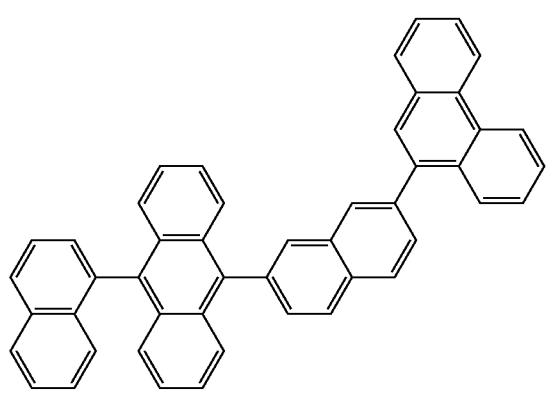
H21
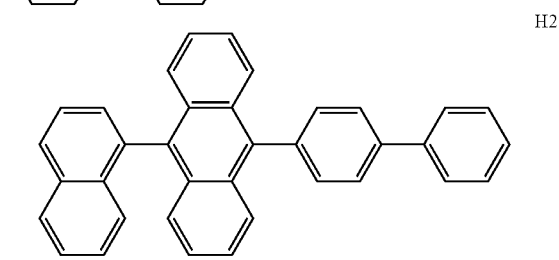
H22
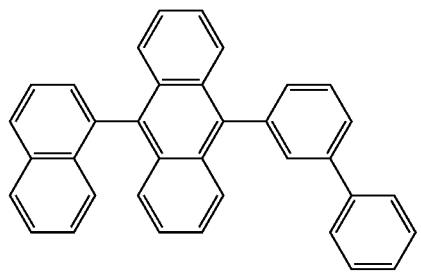
H23
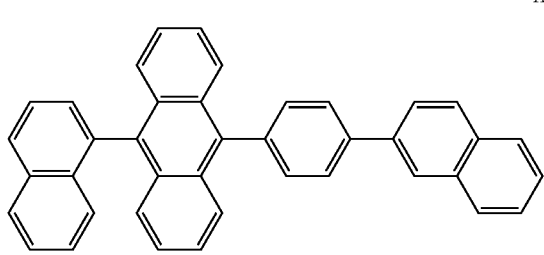
H24
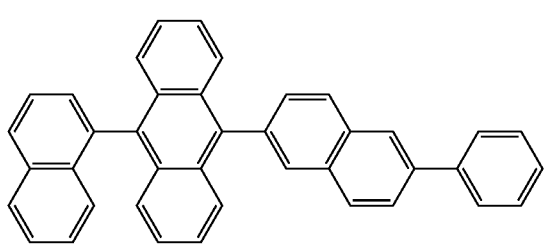
H25
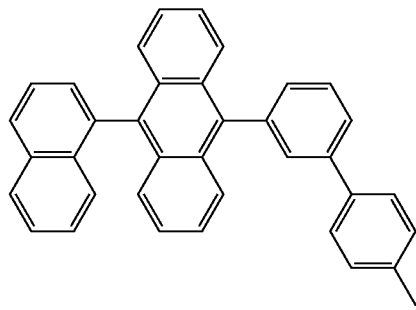
H26
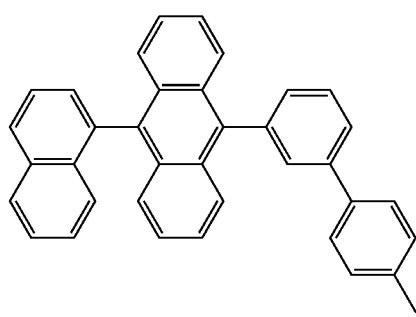

-continued
H27
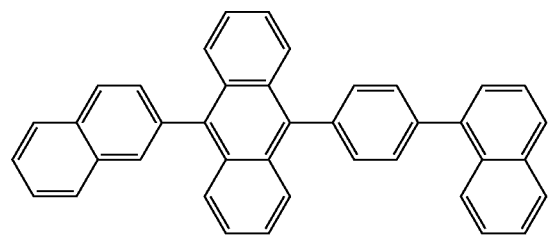
H28
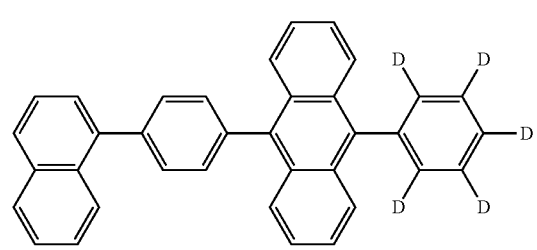
H29
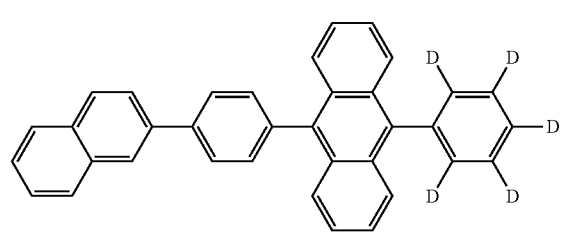
H30
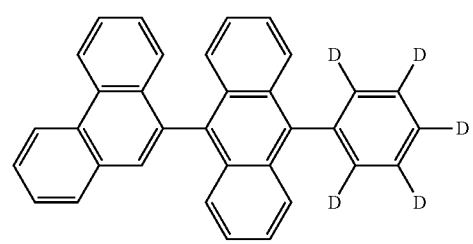
H31
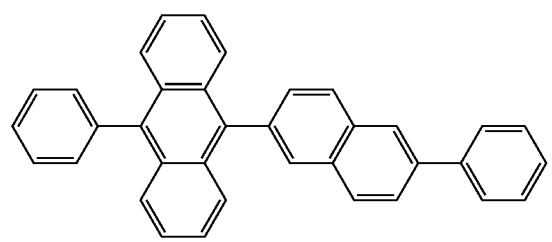
-continued
H32
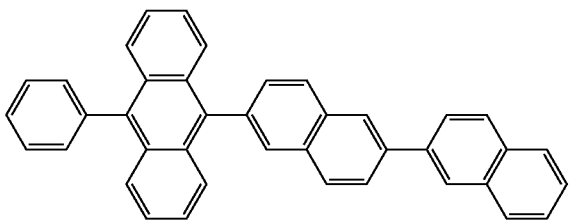
H33
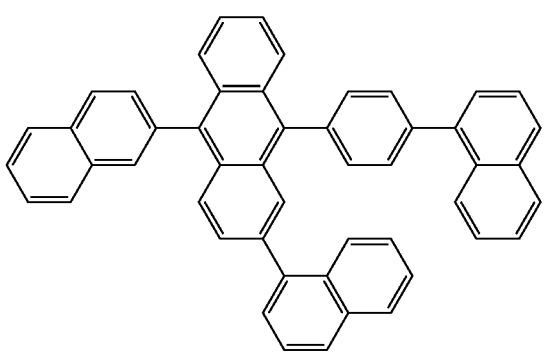
H34
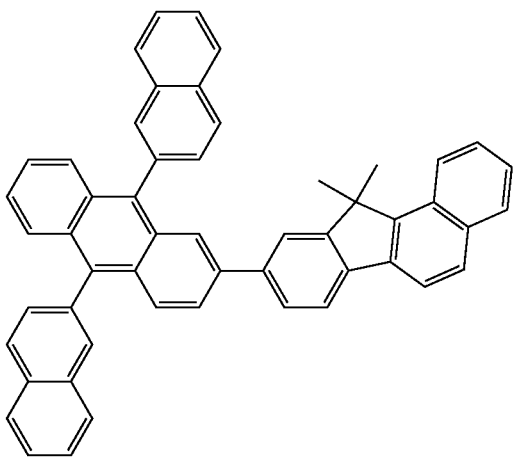
H35
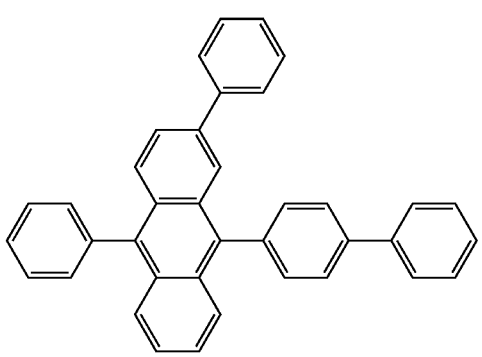

-continued
H36
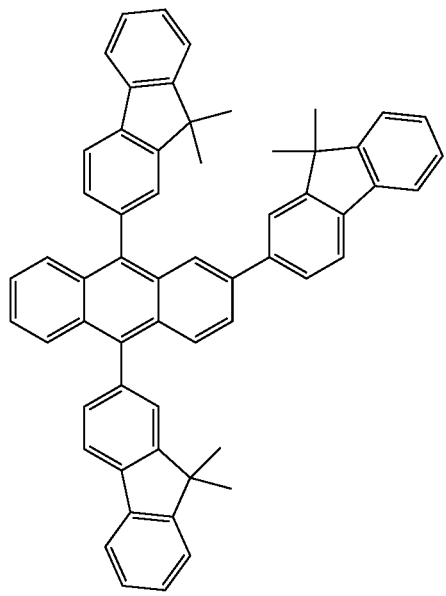
H37
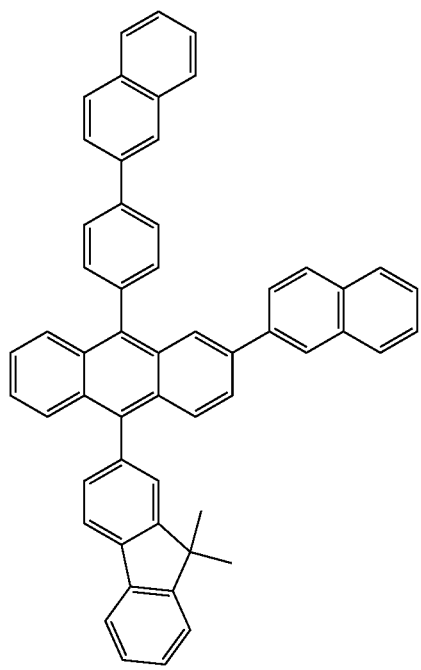
H38
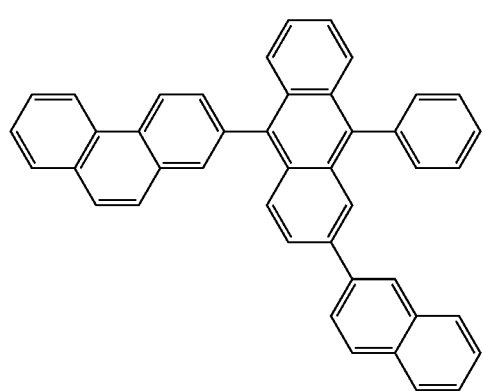
-continued
H39
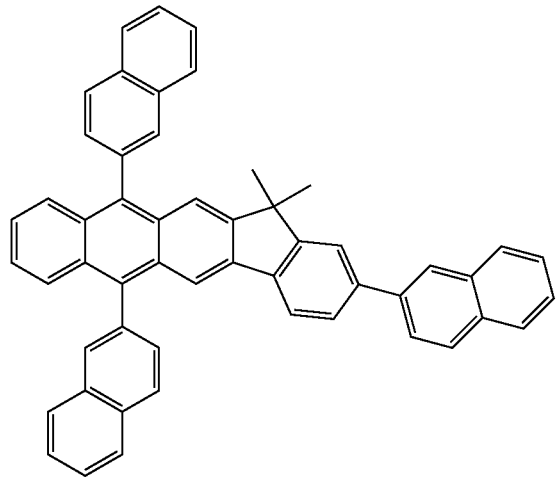
H40
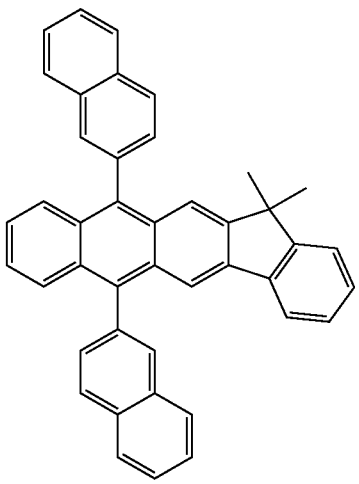
H41
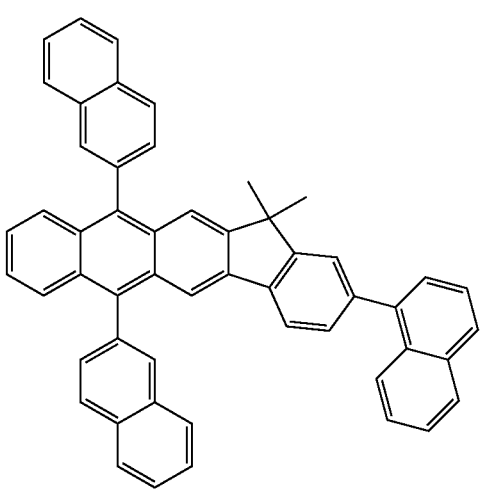

H42
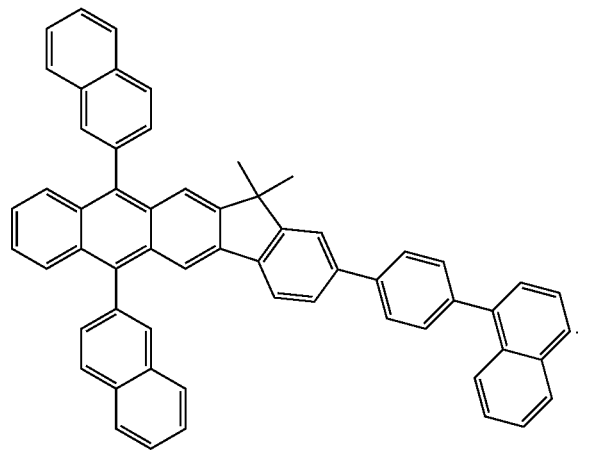
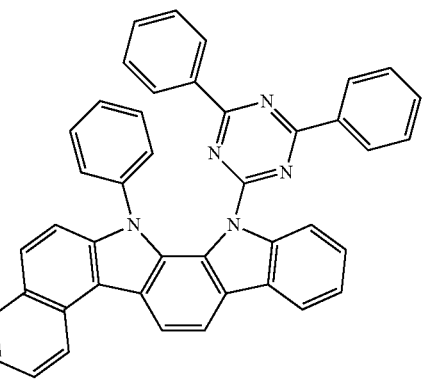
H45
In one or more embodiments, the host may include at least one of Compounds H43 to H49 below, but embodiments of the present disclosure are not limited thereto:
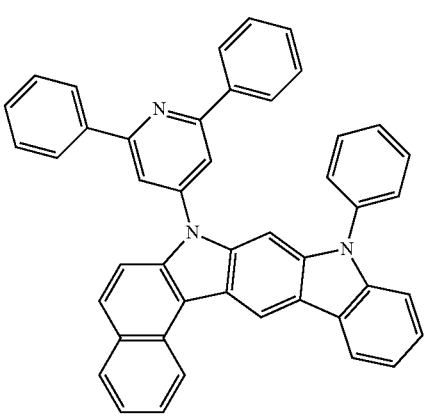
H46
H43
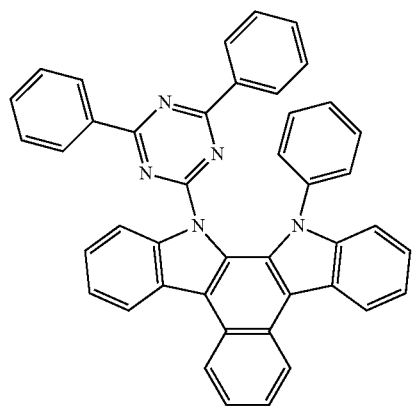
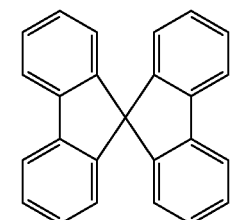
H47
H44
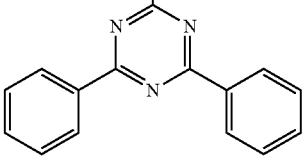
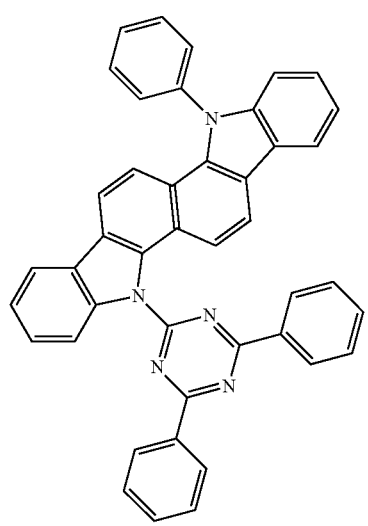
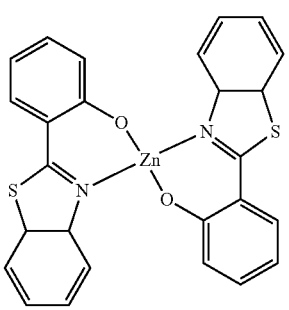
H48

-continued

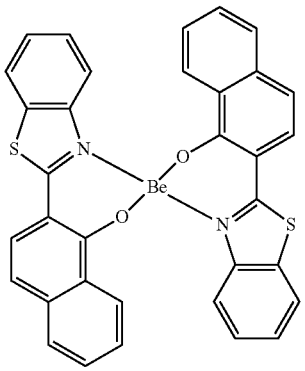

H49

In one or more embodiments, the dopant may include Dopant 1 and Dopant 2.

Dopant 1 may include a known fluorescent dopant or a known phosphorescent dopant.

The phosphorescent dopant may include an organometallic complex represented by Formula 401 below:

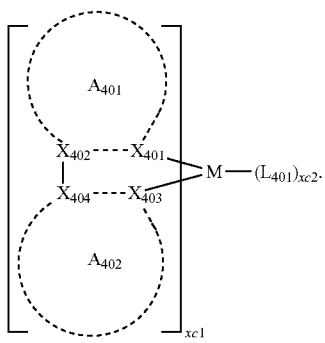

<Formula 401>

In Formula 401,

M may be selected from iridium (Ir), platinum (Pt), osmium (Os), titanium (Ti), zirconium (Zr), hafnium (Hf), europium (Eu), terbium (Tb), and thulium (TM), $X_{401}$ to $X_{404}$ may each independently be nitrogen or carbon, $A_{401}$ and $A_{402}$ rings may each independently be selected from a substituted or unsubstituted benzene group, a substituted or unsubstituted naphthalene group, a substituted or unsubstituted fluorene group, a substituted or unsubstituted spiro-fluorene group, a substituted or unsubstituted indene group, a substituted or unsubstituted pyrrole group, a substituted or unsubstituted thiophene group, a substituted or unsubstituted furan group, a substituted or unsubstituted imidazole group, a substituted or unsubstituted pyrazole group, a substituted or unsubstituted thiazole group, a substituted or unsubstituted isothiazole group, a substituted or unsubstituted oxazole group, a substituted or unsubstituted isoxazole group, a substituted or unsubstituted pyridine group, a substituted or unsubstituted pyrazine group, a substituted or unsubstituted pyrimidine group, a substituted or unsubstituted pyridazine group, a substituted or unsubstituted quinoline group, a substituted or unsubstituted isoquinoline group, a substituted or unsubstituted benzoquinoline group, a substituted or unsubstituted quinoxaline group, a substituted or unsubstituted quinazoline group, a substituted or unsubstituted carbazol group, a substituted or unsubstituted benzimidazole group, a substituted or unsubstituted benzofuran group, a substituted or unsubstituted benzothiophene group, a substituted or unsubstituted isobenzothiophene group, a substituted or unsubstituted benzoxazole group, a substituted or unsubstituted isobenzoxazole group, a substituted or unsubstituted triazole group, a substituted or unsubstituted oxadiazole group, a substituted or unsubstituted triazine group, a substituted or unsubstituted dibenzofuran group, and a substituted or unsubstituted dibenzothiophene group, at least one substituent of the substituted benzene group, the substituted naphthalene group, the substituted fluorene group, the substituted spiro-fluorene group, the substituted indene group, the substituted pyrrole group, the substituted thiophene group, the substituted furan group, the substituted imidazole group, the substituted pyrazole group, the substituted thiazole group, the substituted isothiazole group, the substituted oxazole group, the substituted isoxazole group, the substituted pyridine group, the substituted pyrazine group, the substituted pyrimidine group, the substituted pyridazine group, the substituted quinoline group, the substituted isoquinoline group, the substituted benzoquinoline group, the substituted quinoxaline group, the substituted quinazoline group, the substituted carbazol group, the substituted benzimidazole group, the substituted benzofuran group, the substituted benzothiophene group, the substituted isobenzothiophene group, the substituted benzoxazole group, the substituted isobenzoxazole group, the substituted triazole group, the substituted oxadiazole group, the substituted triazine group, the substituted dibenzofuran group, and the substituted dibenzothiophene group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{401})(Q_{402})$, —$Si(Q_{403})(Q_{404})(Q_{405})$, and —$B(Q_{406})(Q_{407})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, and a non-aromatic condensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_1$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$), $L_{401}$ is an organic ligand, xc1 is 1, 2, or 3, and xc2 is 0, 1, 2, or 3.

$L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propandionate, 2,2,6,6-tetramethyl-3,5-heptandionate, or hexafluoroacetonate), a carboxylic acid ligand (for example, picolinate, dimethyl-3-pyrazolecarboxylate, or benzoate), a carbon monooxide ligand, an isonitrile ligand, a cyano ligand, and a phosphorous ligand (for example, phosphine, and phosphite), but embodiments of the present disclosure are not limited thereto.

When $A_{401}$ in Formula 401 has two or more substituents, the substituents of $A_{401}$ may be linked to each other to form a saturated or unsaturated ring.

When $A_{401}$ in Formula 402 has two or more substituents, the substituents of $A_{402}$ may be linked to each other to form a saturated or unsaturated ring.

When xc1 in Formula 401 is two or more, a plurality of ligands

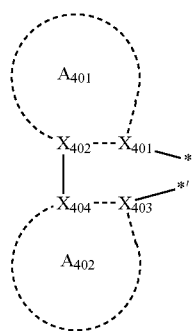

in Formula 401 may be identical or different from each other. When xc1 in Formula 401 is two or more, $A_{401}$ and $A_{402}$ may be respectively directly connected to $A_{401}$ and $A_{402}$ of other neighboring ligands with or without a linker (for example, a $C_1$-$C_5$ alkylene, or —N(R')— (wherein R' may be a $C_1$-$C_{10}$ alkyl group or a $C_6$-$C_{20}$ aryl group) or —C(=O)—) therebetween.

The phosphorescent dopant may include at least one of Compounds PD1 to PD74 below, but embodiments of the present disclosure are not limited thereto:

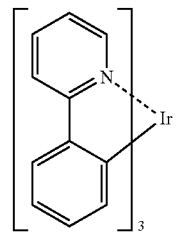

PD1

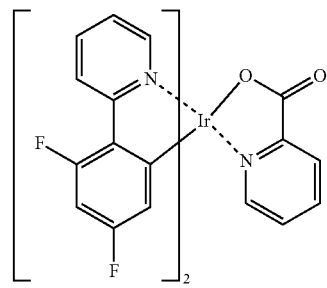

PD2

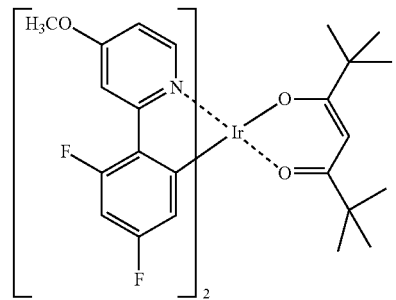

PD3

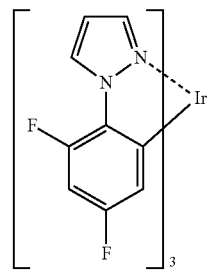

PD4

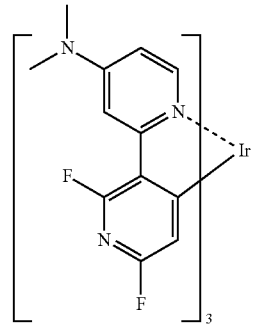

PD5

PD6 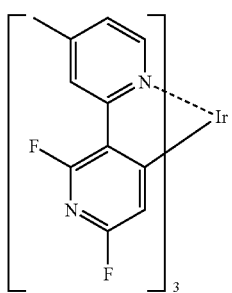
PD7 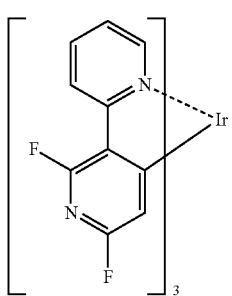
PD8 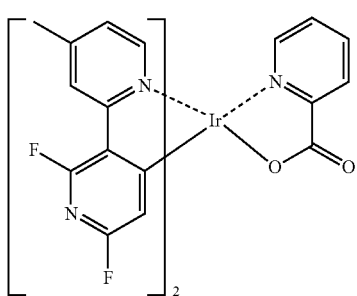
PD9 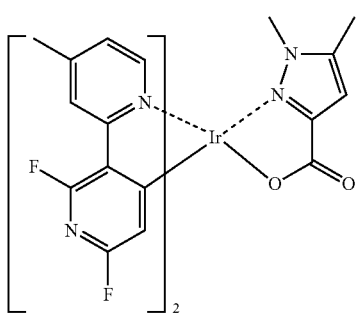
PD10 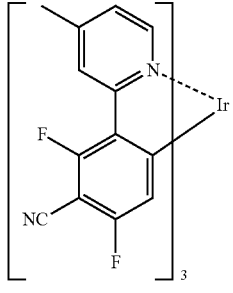
PD11 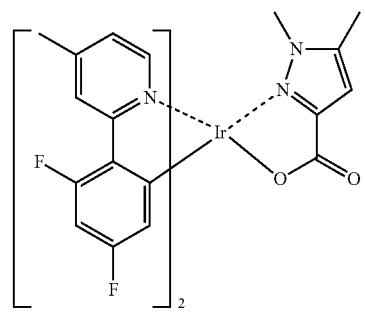
PD12 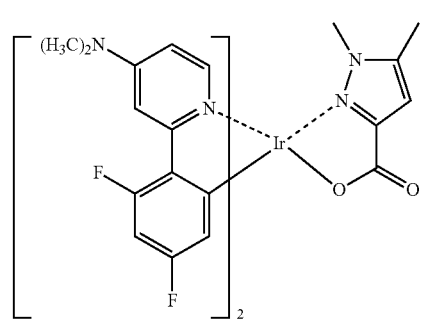
PD13 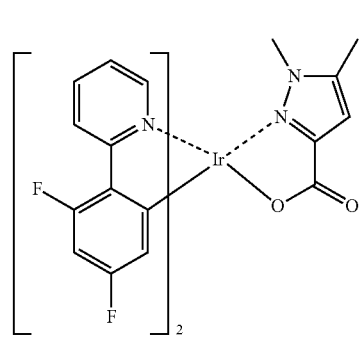
PD14 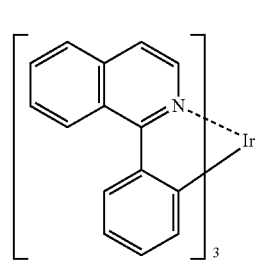
PD15 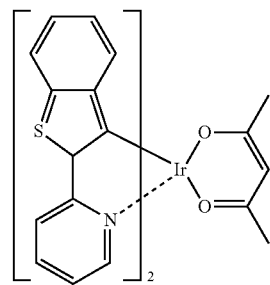

PD16
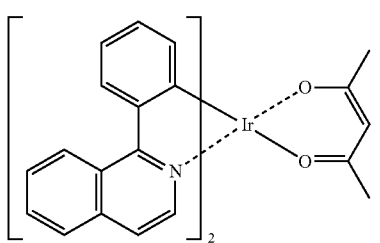
PD17
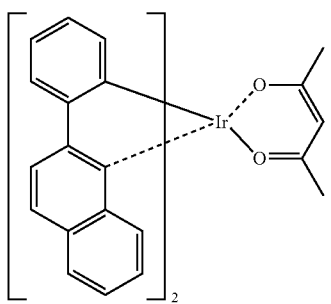
PD18
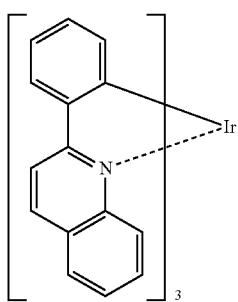
PD19
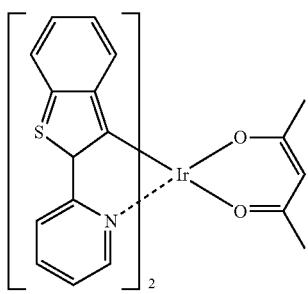
PD20
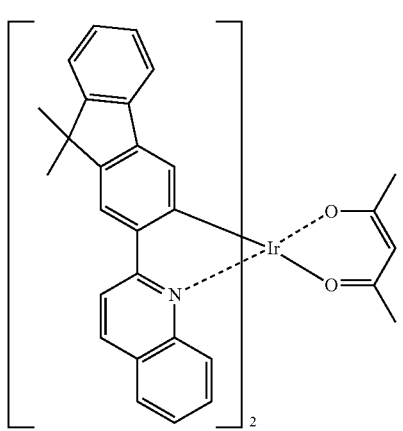
PD21
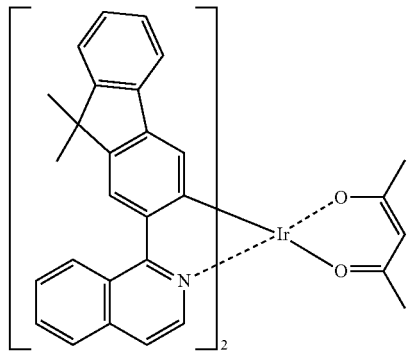
PD22
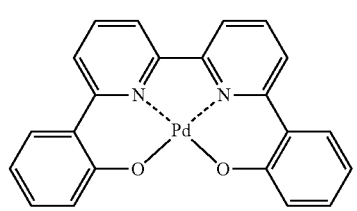
PD23
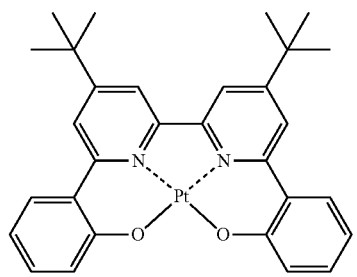
PD24
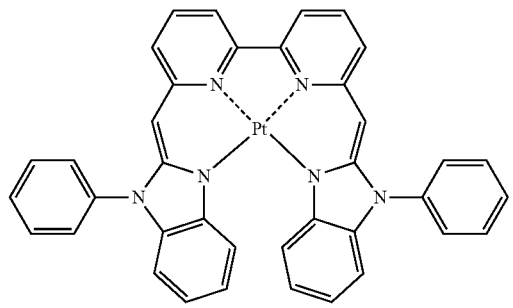
PD25
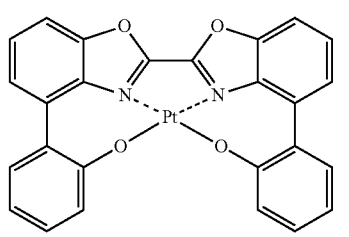
PD26
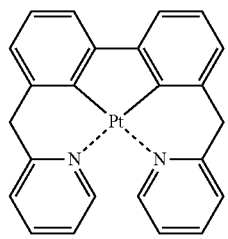

-continued
PD27 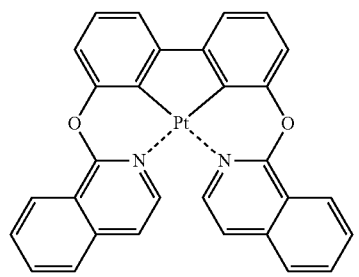
PD28 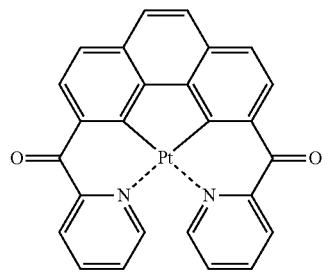
PD29 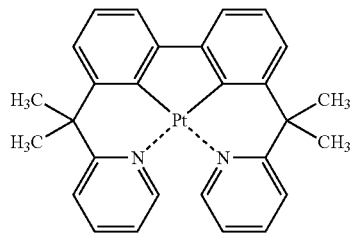
PD30 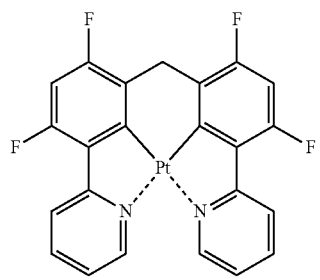
PD31 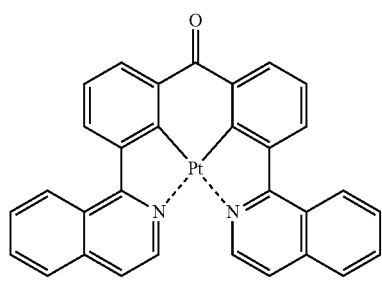
PD32 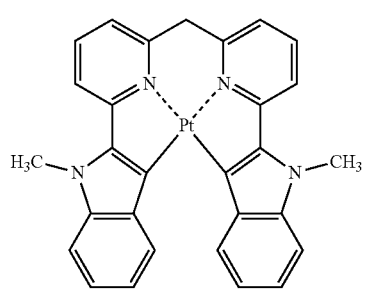
-continued
PD33 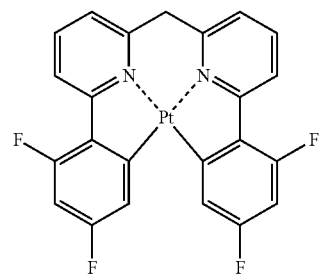
PD34 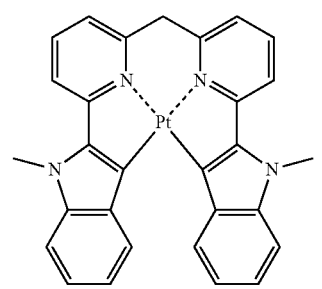
PD35 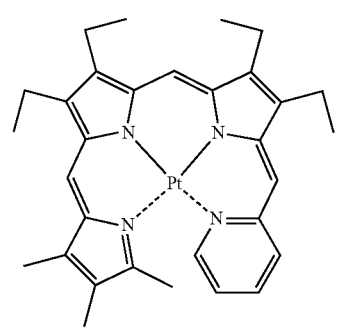
PD36 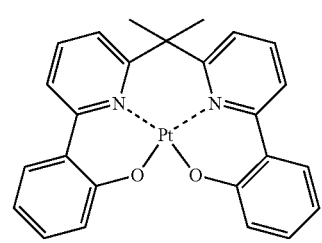
PD37 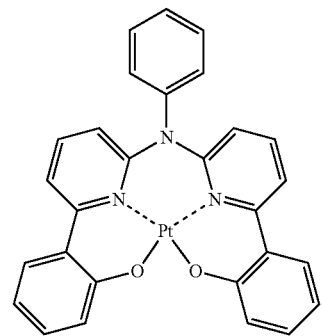

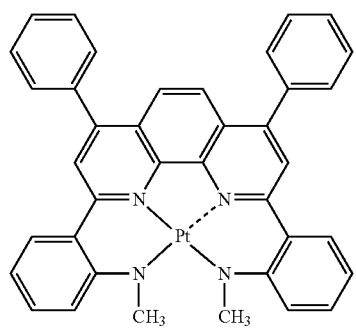
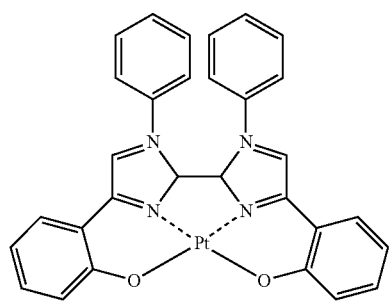
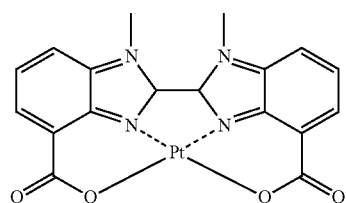
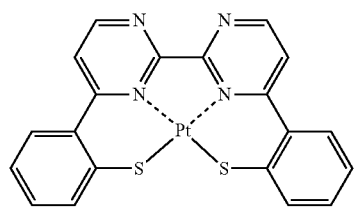
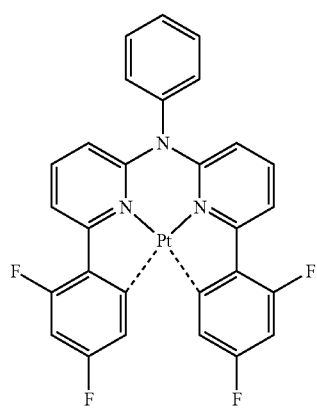
PD38
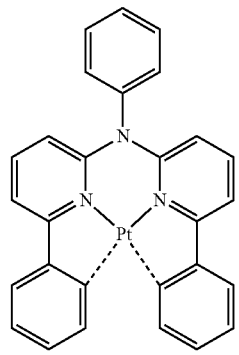
PD39
PD40
PD41
PD42
PD43
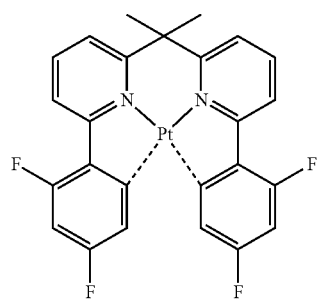
PD44
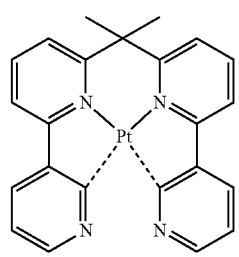
PD45
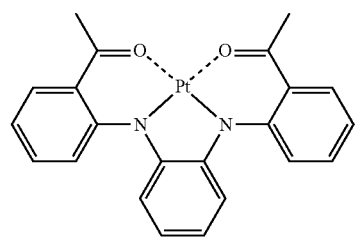
PD46
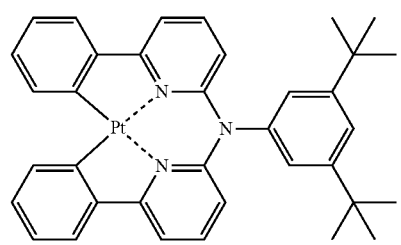
PD47
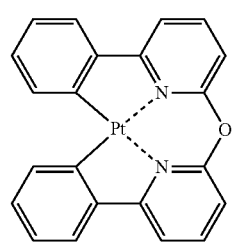
PD48

PD49 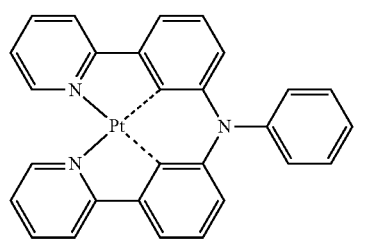
PD50 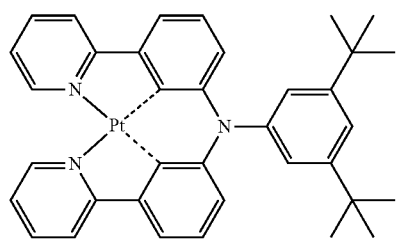
PD51 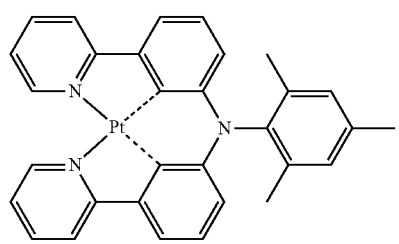
PD52 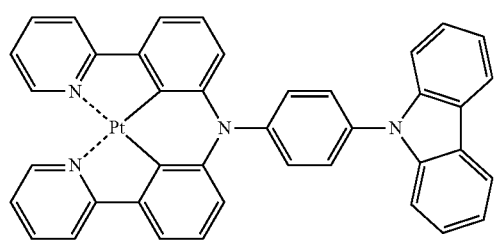
PD53 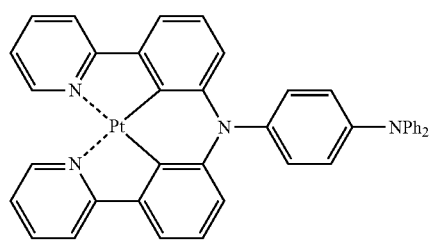
PD54 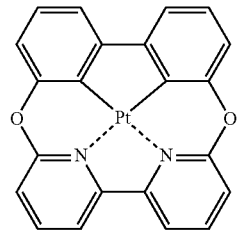
PD55 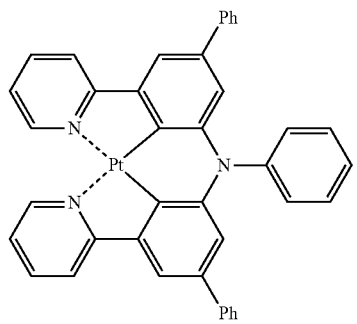
PD56 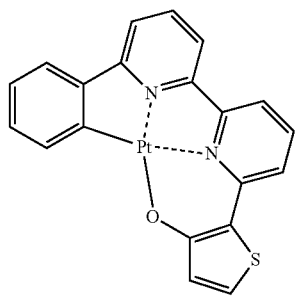
PD57 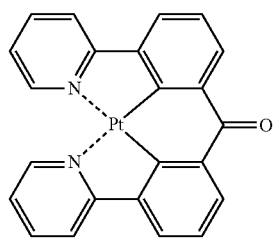
PD58 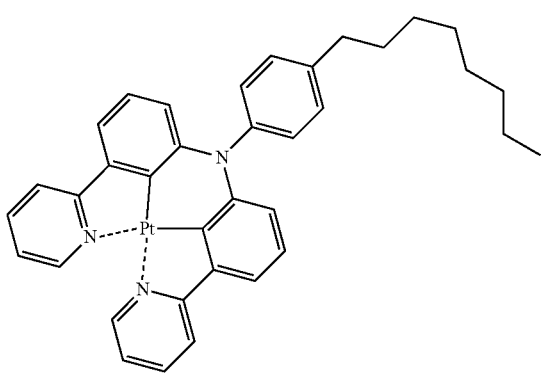
PD59 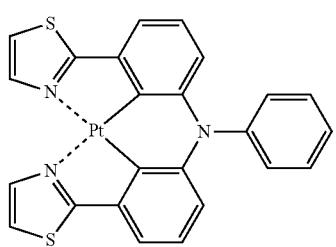

-continued
PD60 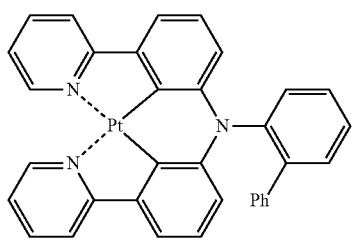
PD61 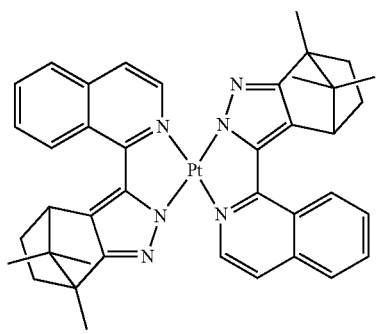
PD62 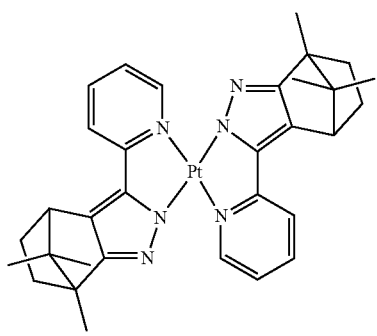
PD63 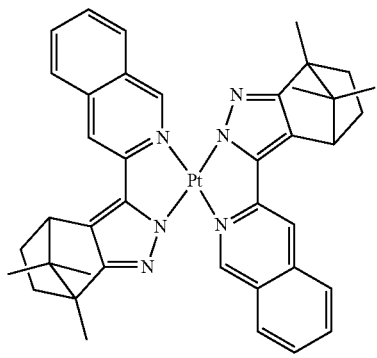
PD64 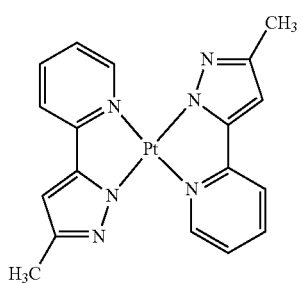
-continued
PD65 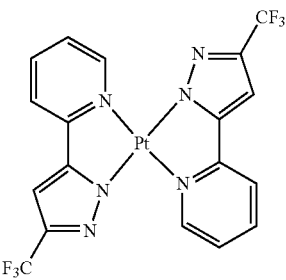
PD66 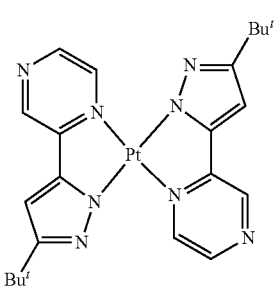
PD67 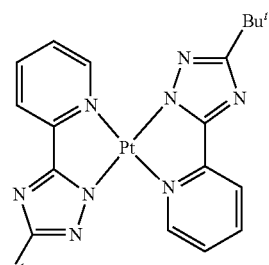
PD68 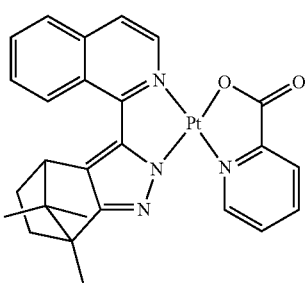
PD69 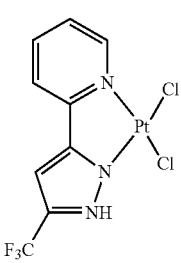

-continued
PD70
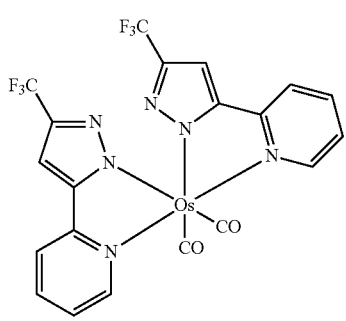
PD71
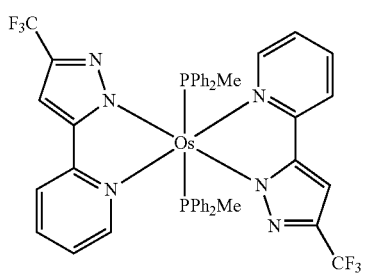
PD72
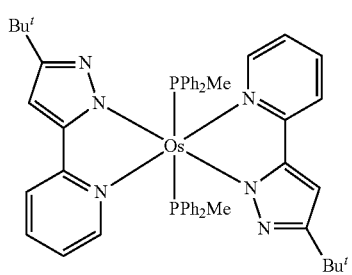
PD73
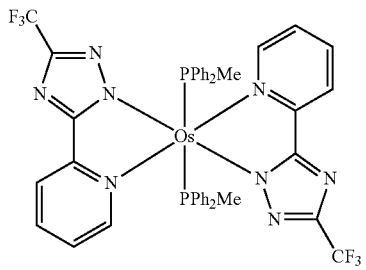
-continued
PD74
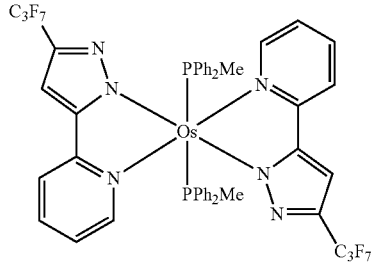
In one or more embodiments, the phosphorescent dopant may include PtOEP:
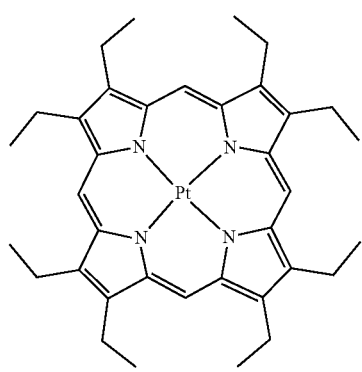
PtOEP
The fluorescent dopant may include at least one selected from DPAVBi, BDAVBi, TBPe, DCM, DCJTB, Coumarin 6, and C545T.
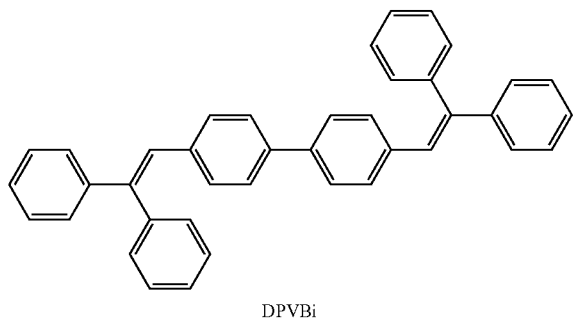
DPVBi -continued

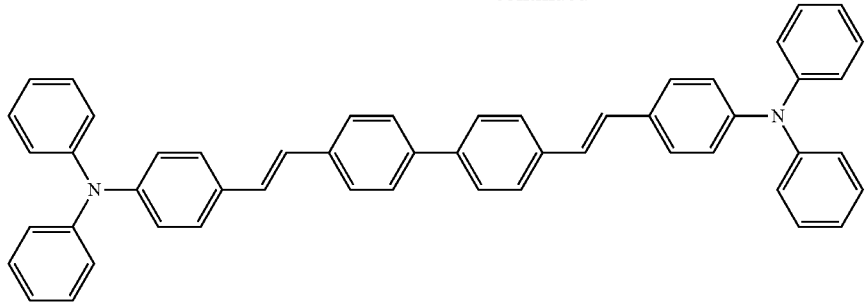

DPAVBi

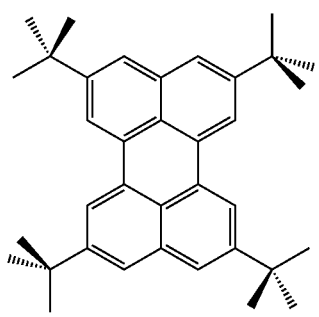

TBPe

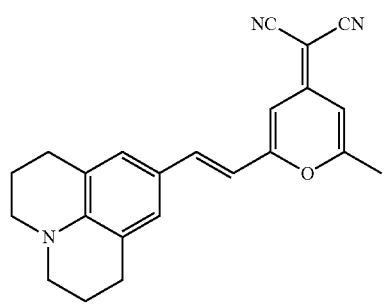

DCM

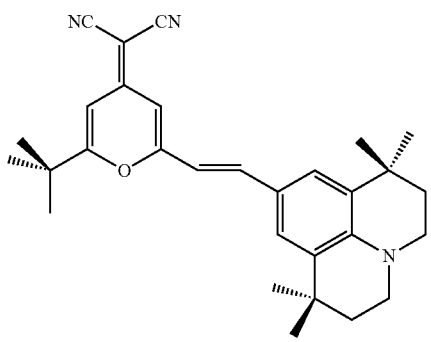

DCJTB

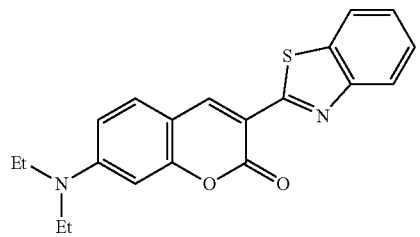

Coumarin 6

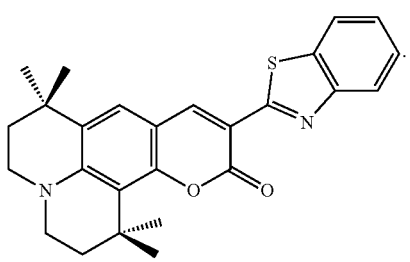

C545T

In one or more embodiments, the fluorescent dopant may include a compound represented by Formula 501 below.

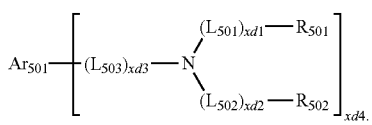

<Formula 501>

In Formula 501, $Ar_{501}$ may be selected from:

a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) ($Q_{501}$ to $Q_{503}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group).

Descriptions of $L_{501}$ to $L_{503}$ are the same as the descriptions provided herein in connection with $L_{203}$;

$R_{501}$ and $R_{502}$ may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may each independently be selected from 0, 1, 2, and 3, and xb4 may be selected from 1, 2, 3, and 4.

The fluorescent dopant may include at least one of Compounds FD1 to FD8:

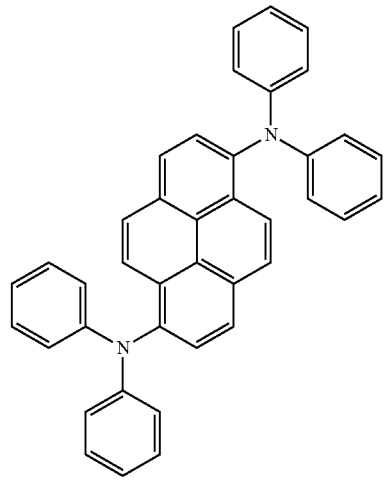

FD1

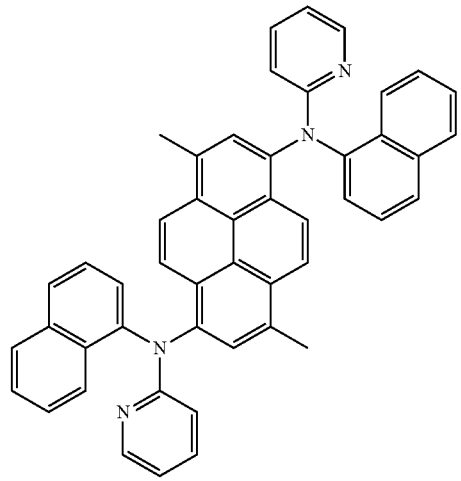

FD2

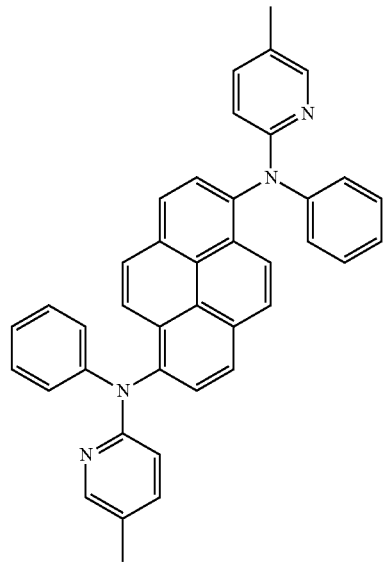

FD3

FD4

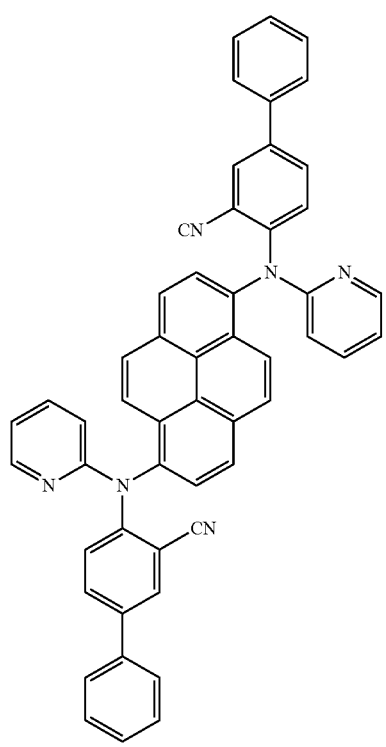

FD6

FD7

FD8

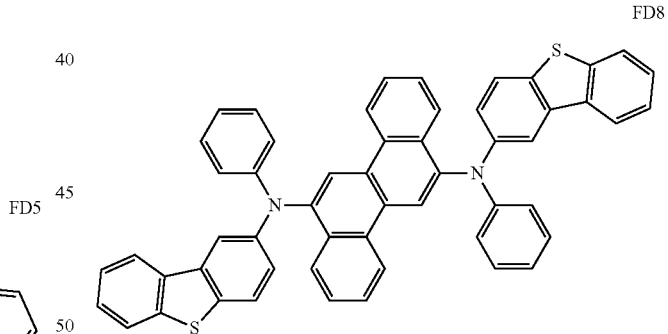

FD5

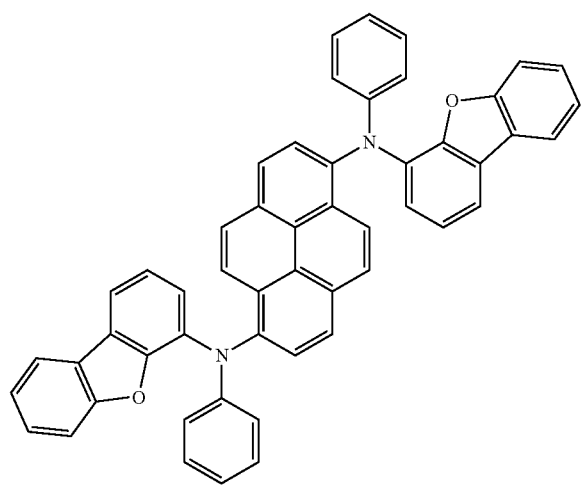

In one embodiment, Dopant 2 may include the compound represented by Formula 1.

In one embodiment, weight ratios of the host, Dopant 1, and Dopant 2 may be in the following ranges:

75 wt %≤host≤83 wt %
16 wt %≤Dopant 1≤24 wt %
0.7 wt %≤Dopant 2≤1.5 wt %

(the sum of the weight ratios of the host, Dopant 1, and Dopant 2 is 100 wt %).

A thickness of the emission layer may be in a range of about 100 Å to about 1,000 Å, for example, about 200 Å to about 600 Å When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer, but embodiments of the present disclosure are not limited thereto.

When the electron transport region includes a hole blocking layer, the hole blocking layer may be formed on the emission layer by using one or more suitable methods selected from vacuum deposition, spin coating, casting, an LB deposition, ink-jet printing, laser-printing, and/or laser-induced thermal imaging. When the hole blocking layer is formed by vacuum deposition or spin coating, deposition and coating conditions for the hole blocking layer may be determined by referring to the deposition and coating conditions for the hole injection layer.

The hole blocking layer may include, for example, at least one of BCP and Bphen, but embodiments of the present disclosure are not limited thereto.

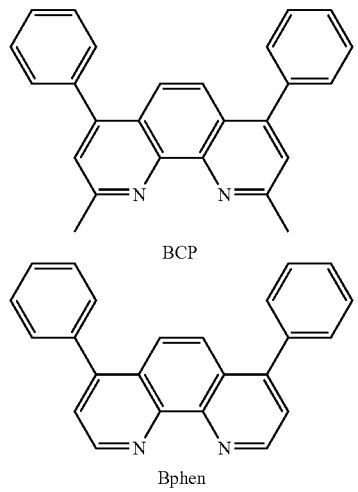

A thickness of the hole blocking layer may be in a range of about 20 Å to about 1,000 Å, for example, about 30 Å to about 300 Å When the thickness of the hole blocking layer is within these ranges, the hole blocking layer may have excellent hole blocking characteristics without a substantial increase in driving voltage.

For example, the electron transport region may have an electron transport layer/electron injection layer structure or a hole blocking layer/electron transport layer/electron injection layer structure, wherein layers of each structure are sequentially stacked from the emission layer in the stated order, but the structure thereof is not limited thereto.

According to an embodiment, the organic layer 150 of the organic light-emitting device 10 includes an electron transport region between the emission layer and the second electrode 190, and the electron transport region may include an electron transport layer. The electron transport layer may include a plurality of layers. For example, the electron transport layer may include a first electron transport layer and a second electron transport layer.

The electron transport layer may further include at least one selected from BCP, Bphen, Alq$_3$, BAlq, TAZ, and NTAZ.

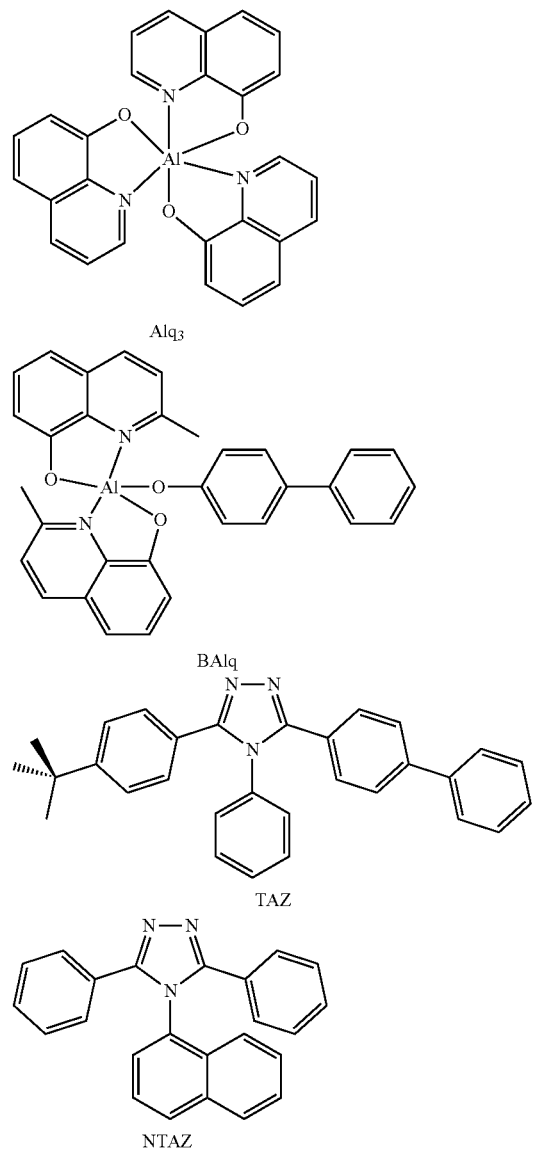

In one or more embodiments, the electron transport layer may include at least one compound selected from a compound represented by Formula 601 and a compound represented by Formula 602 illustrated below:

$$Ar_{601}\text{-}[(L_{601})_{xe1}\text{-}E_{601}]_{xe2} \qquad \text{<Formula 601>}$$

In Formula 601, $Ar_{601}$ may be selected from:

a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group; and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) ($Q_{301}$ to $Q_{303}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group), a description of $L_{601}$ may be understood by referring to the description provided in connection with $L_{301}$, $E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, xe1 may be selected from 0, 1, 2, and 3, and
xe2 may be selected from 1, 2, 3, and 4.

<Formula 602>

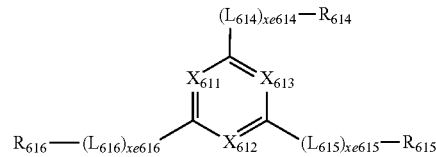

In Formula 602, $X_{611}$ may be N or C-($L_{611}$)xe$_{611}$-$R_{611}$, $X_{612}$ may be N or C-($L_{612}$)xe$_{612}$-$R_{612}$, and $X_{613}$ may be N or C-($L_{613}$)xe$_{613}$-$R_{613}$, and at least one selected from $X_{611}$ to $X_{613}$ may be N, $L_{611}$ to $L_{616}$ may be understood by referring to the description provided herein in connection with $L_{301}$, $R_{611}$ to $R_{616}$ may each independently be selected from:

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C1-C20 alkyl group, a C1-C20 alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and xe611 to xe616 may each independently be selected from 0, 1, 2, and 3.

The compound represented by Formula 601 and the compound represented by Formula 602 may each be selected from Compounds ET1 to ET15 illustrated below.

ET1

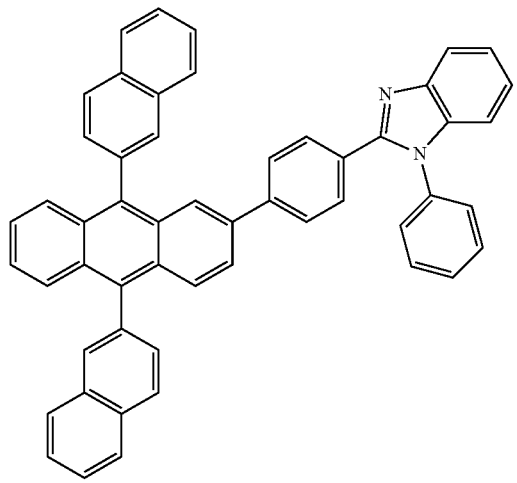

ET2

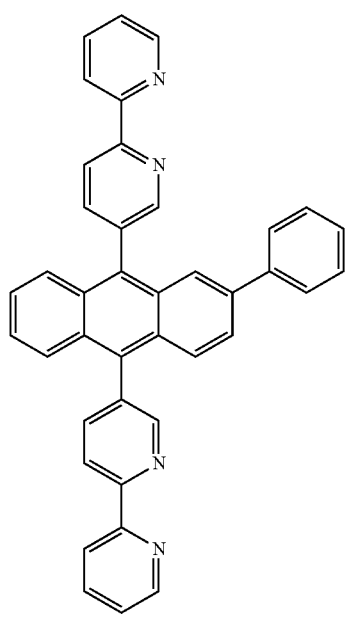

ET3

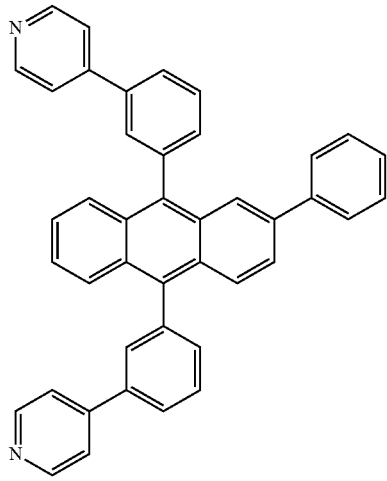

ET4

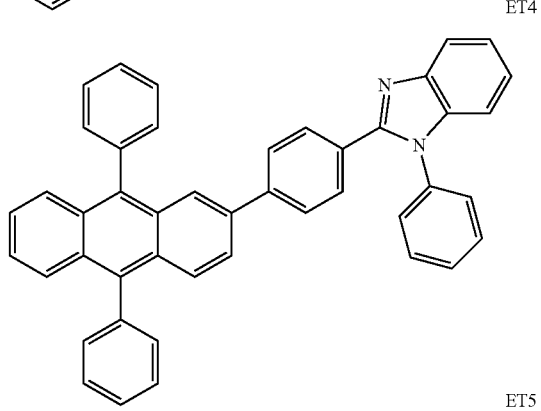

ET5

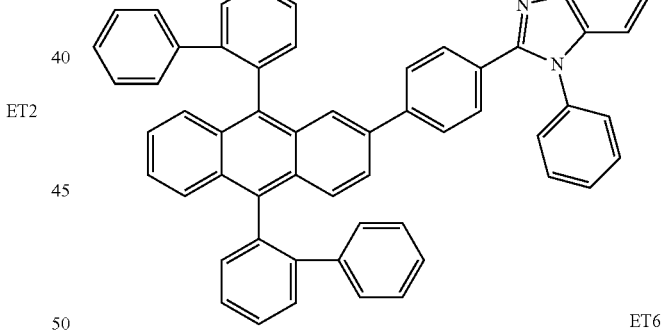

ET6

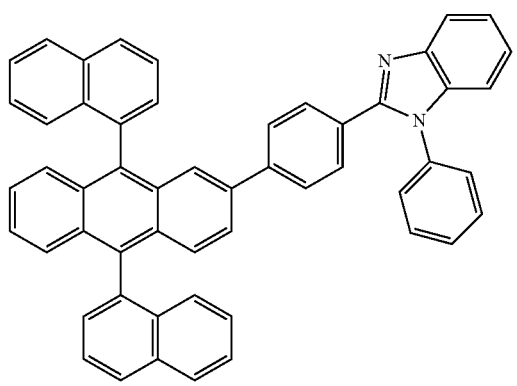

ET7
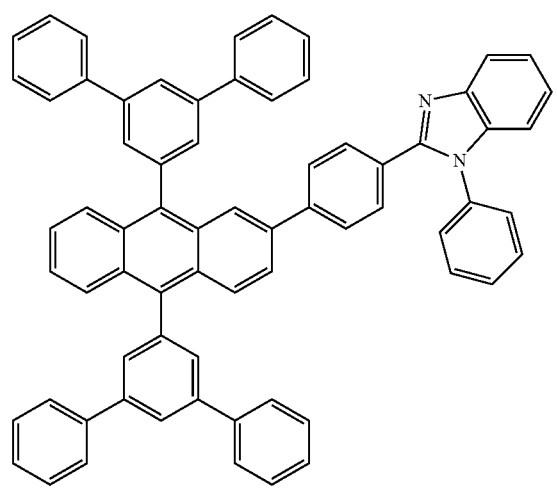
ET8
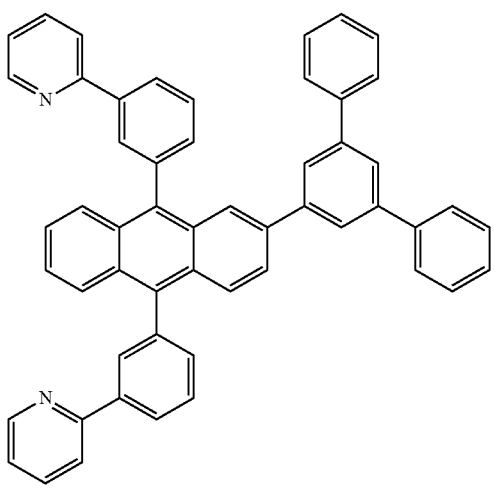
ET9
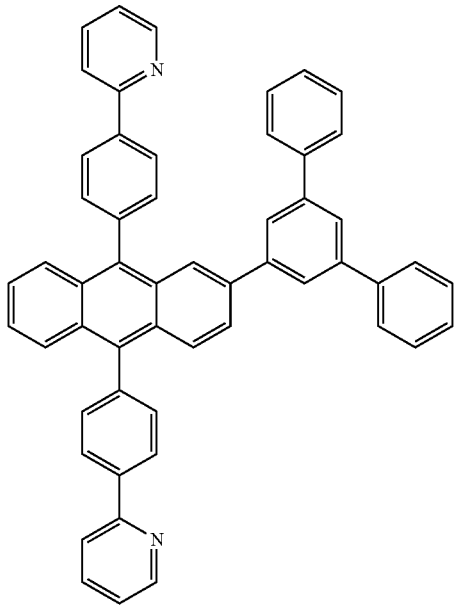
ET10
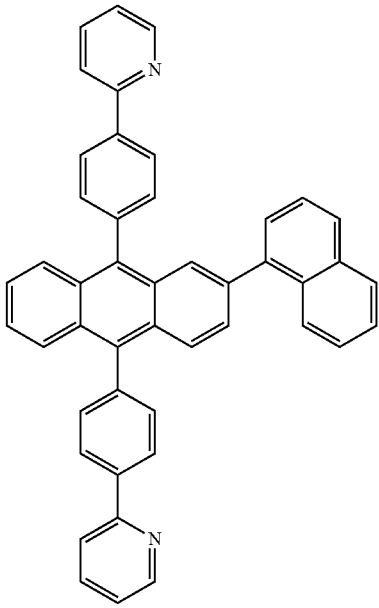
ET11
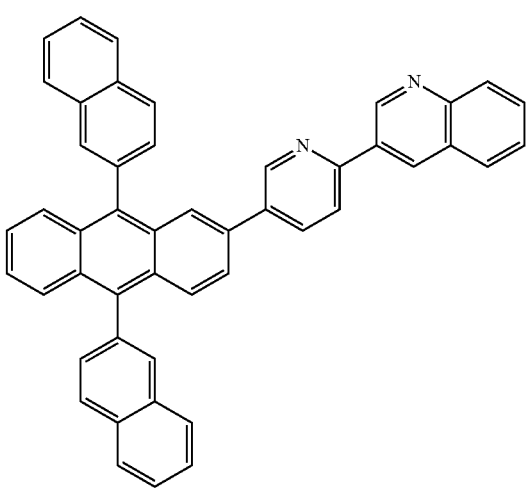
ET12
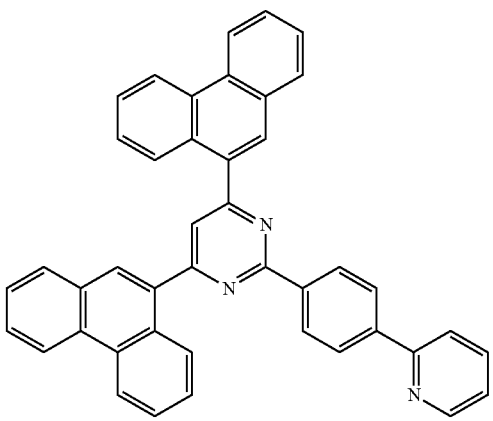

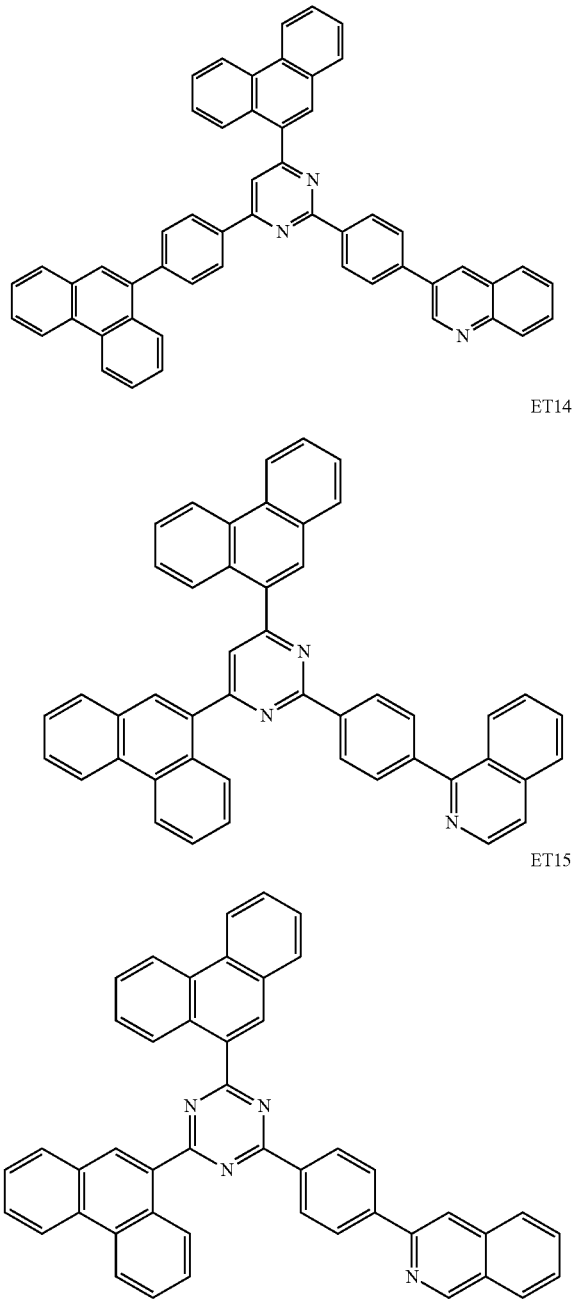

A thickness of the electron transport layer may be in a range of about 100 Å to about 1,000 Å, for example, about 150 Å to about 500 Å When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

The electron transport region may include an electron injection layer that facilitates injection of electrons from the second electrode 190.

The electron injection layer may be formed on the electron transport layer by using one or more suitable methods selected from vacuum deposition, spin coating, casting, a LB method, ink-jet printing, laser-printing, and laser-induced thermal imaging. When an electron injection layer is formed by vacuum deposition or spin coating, deposition and coating conditions for the electron injection layer may be the same as those for the hole injection layer.

The electron injection layer may include at least one selected from LiF, a NaCl, CsF, $Li_2O$, BaO, and LiQ.

A thickness of the electron injection layer may be in a range of about 1 Å to about 100 Å, for example, about 3 Å to about 90 Å When the thickness of the electron injection layer is within the range described above, the electron injection layer may have satisfactory electron injection characteristics without a substantial increase in driving voltage.

The second electrode 190 may be disposed on the organic layer 150 having such a structure. The second electrode 190 may be a cathode which is an electron injection electrode, and in this regard, a material for forming the second electrode 190 may be selected from metal, an alloy, an electrically conductive compound, and a mixture thereof, which have a relatively low work function. Examples of the second electrode 190 are lithium (Li), magnesium (Mg), aluminum (Al), aluminum-lithium (Al—Li), calcium (Ca), magnesium-indium (Mg—In), and magnesium-silver (Mg—Ag). In one or more embodiments, the material for forming the second electrode 190 may be ITO or IZO. The second electrode 190 may be a reflective electrode, a semi-transmissive electrode, or a transmissive electrode.

Also, an organic layer according to an embodiment may be formed by depositing the compound according to an embodiment, or may be formed by using a wet method in which the compound according to an embodiment is prepared in the form of solution and then the solution of the compound is used for coating.

An organic light-emitting device according to an embodiment may be used in various flat panel display apparatuses, such as a passive matrix organic light-emitting display apparatus or an active matrix organic light-emitting display apparatus. For example, when the organic light-emitting device is included in an active matrix organic light-emitting display apparatus, a first electrode disposed on a substrate acts as a pixel and may be electrically connected to a source electrode or a drain electrode of a thin film transistor. In addition, the organic light-emitting device may be included in a flat panel display apparatus that emits light in opposite directions.

Hereinbefore, the organic light-emitting device has been described with reference to FIG. 1, but embodiments of the present disclosure are not limited thereto.

Hereinafter, definitions of substituents of compounds used herein will be presented (the number of carbon atoms used to restrict a substituent is not limited, and does not limit properties of the substituent, and unless defined otherwise, the definition of the substituent is consistent with a general definition thereof).

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, and S as a ring-forming atom and 1 to 10 carbon atoms, and examples thereof include a tetrahydrofuranyl group and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_2$-$C_{10}$ heterocycloalkenyl group" as used herein refers to a monovalent monocyclic group that has at least one heteroatom selected from N, O, P, and S as a ring-forming atom, 2 to 10 carbon atoms, and at least one carbon-carbon double bond in its ring. Examples of the $C_2$-$C_{10}$ heterocycloalkenyl group include a 2,3-dihydrofuranyl group and a 2,3-dihydrothiophenyl group. The term "$C_2$-$C_{10}$ heterocycloalkenylene group" as used herein refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Examples of the $C_6$-$C_{60}$ aryl group include a phenyl group, a biphenyl group, a terphenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a carbocyclic aromatic system that has at least one heteroatom selected from N, O, P, and S as a ring-forming atom, in addition to 1 to 60 carbon atoms. A $C_1$-$C_{60}$ heteroarylene group used herein refers to a divalent group having a carbocyclic aromatic system that has at least one heteroatom selected from N, O, P, and S as a ring-forming atom, in addition to 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein indicates —$OA_{102}$ (wherein $A_{102}$ is the $C_6$-$C_{60}$ aryl group), and a $C_6$-$C_{60}$ arylthio group indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, has a heteroatom selected from N, O, P, and S, other than carbon atoms, as a ring-forming atom, and has no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

In the present specification, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_1$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), and $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, $-N(Q_{11})(Q_{12})$, $-Si(Q_{13})(Q_{14})(Q_{15})$, and $-B(Q_{16})(Q_{17})$;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, $-N(Q_{21})(Q_{22})$, $-Si(Q_{23})(Q_{24})(Q_{25})$, and $-B(Q_{26})(Q_{27})$; and $-N(Q_{31})(Q_{32})$, $-Si(Q_{33})(Q_{34})(Q_{35})$, and $-B(Q_{36})(Q_{37})$, and $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The expression "Ph" used herein refers to a phenyl group, the expression "Me" used herein refers to a methyl group, the expression "Et" used herein refers to an ethyl group, and the expression "ter-Bu" or "Bu$^t$" used herein refers to a tert-butyl group.

Hereinafter, an organic light-emitting device according to an embodiment will be described in detail with reference to Synthesis Examples and Examples.

Synthesis Example

Synthesis Example 1: Synthesis of Compounds 433 to 435

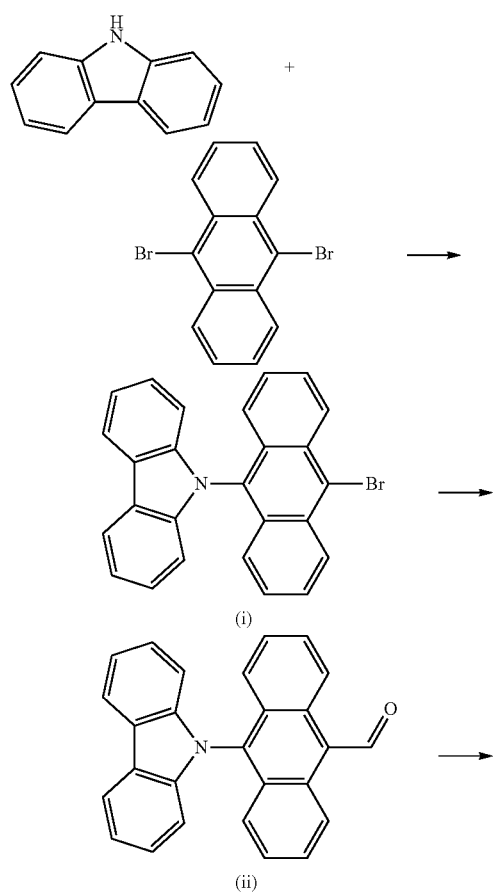

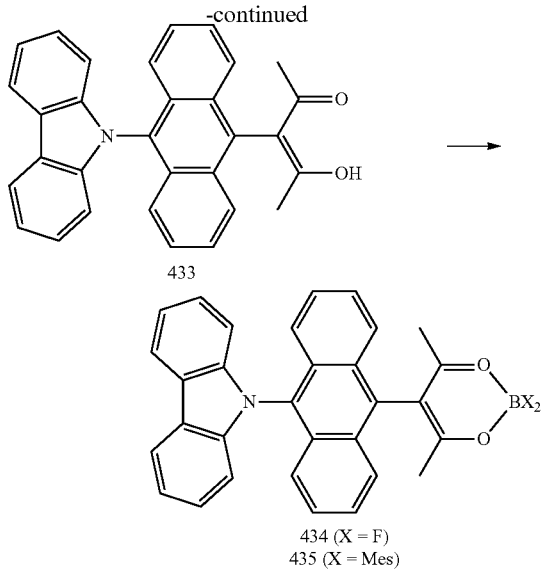

434 (X = F)
435 (X = Mes)

[Intermediate (i)]

5.0 g (29.90 mmol) of carbazole, 12.06 g (35.88 mmol) of 9,10-dibromoanthracene, 1.14 g (5.98 mmol) of CuI, 1.08 g (5.98 mmol) of 1,10-phenanthroline, and 7.79 g (59.80 mmol) of potassium carbonate were dissolved in 25 mL of N,N-dimethylformamide solvent. The reaction mixture was heated to a temperature of 160° C. and stirred for 10 hours. Then, the reaction mixture was cooled to room temperature, and an organic layer was extracted therefrom three times by using dichloromethane and water. The extracted organic layer was dried by using magnesium sulfate, and a solvent was evaporated therefrom. Then, the residue obtained therefrom was separated and purified by silica gel column chromatography to obtain Intermediate (i). The obtained compound was identified by $^1$H, $^{13}$C NMR, and HR-EIMS. Yield: 8.21 g (19.44 mmol, 65%). $^1$H NMR (500 MHz, CDCl$_3$, δ, ppm): 8.72 (td, $J_{H-H}$=8.9 Hz, $J_{H-H}$=0.9 Hz, 2H), 8.29 (td, $J_{H-H}$=7.0 Hz, $J_{H-H}$=1.3 Hz, 2H), 7.67-7.61 (m, 2H), 7.35-7.24 (8H, m), 6.72 (tt, $J_{H-H}$=7.0 Hz, $J_{H-H}$=1.0 Hz, 2H). $^{13}$C NMR (125 MHz, CDCl$_3$, δ, ppm): 139.7, 137.6, 131.3, 128.0, 127.4, 126.6, 126.1, 125.8, 123.7, 122.7, 121.4, 120.8, 119.8, 109.5. HR-EIMS (m/z) [M+] calcd for C$_{26}$H$_{16}$BrN 421.0466; found, 421.0468.

[Intermediate (ii)]

10.00 g (26.92 mmol) of Intermediate (i) was dissolved in 250 mL of tetrahydrofuran solvent, and the reactant was cooled to a temperature of −78° C. 11.84 mL (29.62 mmol) of N-butyl lithium (2.5 M solution in hexane) solution was slowly added dropwise to the reactant and stirred at the same temperature for 1 hour. Then, 4.2 mL (53.84 mmol) of N,N-dimethylformamide was added dropwise to the reaction mixture. The resultant mixture was heated to room temperature and stirred for 10 hours. After the reaction was completed, an organic layer was extracted therefrom three times by using dichloromethane and water. The extracted organic layer was dried by using magnesium sulfate, and a solvent was evaporated therefrom. Then, the residue obtained therefrom was separated and purified by silica gel column chromatography to obtain Intermediate (ii). The obtained compound was identified by $^1$H, $^{13}$C NMR, and HR-EIMS. Yield: 6.80 g (18.31 mmol, 68%). $^1$H NMR (500 MHz, CDCl$_3$, δ, ppm): 10.54 (s, 1H), 8.73 (td, $J_{H-H}$=8.9 Hz, $J_{H-H}$=0.9 Hz, 2H), 8.42 (td, $J_{H-H}$=7.0 Hz, $J_{H-H}$=1.3 Hz, 2H), 7.68-7.61 (m, 2H), 7.36-7.22 (8H, m), 6.74 (tt, $J_{H-H}$=7.0 Hz, $J_{H-H}$=1.0 Hz, 2H). $^{13}$C NMR (125 MHz, CDCl$_3$, δ, ppm): 170.1, 144.8, 139.7, 132.6, 128.2, 126.9, 126.6, 126.3, 125.9, 122.7, 122.6, 121.4, 119.8, 109.5. HR-EIMS (m/z) [M$^+$] calcd for C$_{27}$H$_{17}$NO 371.1310; found, 371.1315.

Compound 433

5.00 g (13.46 mmol) of Intermediate (ii) and 8.49 g (40.38 mmol) of 2,2,2,2-tetramethoxy-4,5-dimethyl-1,3,2-dioxaphospholene were dissolved in 5 mL of dichloromethane, and the reaction mixture was heated to a temperature of 70° C. and stirred for 24 hours. The reaction mixture was cooled to room temperature, and 5 mL of methanol was added dropwise thereto. Then, the reaction mixture was heated again at a temperature of 70° C. for 6 hours. Then, the reaction mixture was cooled to room temperature, and an organic layer was extracted therefrom three times by using dichloromethane and water. The extracted organic layer was dried by using magnesium sulfate, and a solvent was evaporated therefrom. Then, the residue obtained therefrom was separated and purified by silica gel column chromatography to obtain Compound 433. The obtained compound was identified by $^1$H, $^{13}$C NMR, and HR-EIMS. Yield: 3.74 g (8.48 mmol, 63%). $^1$H NMR (500 MHz, CDCl$_3$, δ, ppm): 16.30 (s, 1H), 8.63 (td, $J_{H-H}$=8.9 Hz, $J_{H-H}$=0.9 Hz, 2H), 8.32 (td, $J_{H-H}$=7.0 Hz, $J_{H-H}$=1.3 Hz, 2H), 7.68-7.61 (m, 2H), 7.36-7.22 (m, 8H), 6.74 (tt, $J_{H-H}$=7.0 Hz, $J_{H-H}$=1.0 Hz, 2H), 1.90 (s, 6H). $^{13}$C NMR (125 MHz, CDCl$_3$, δ, ppm): 191.8, 139.7, 138.1, 132.8, 128.3, 126.6, 126.4, 125.9, 125.6, 125.4, 123.1, 121.4, 119.8, 109.5, 109.1, 23.9. HR-EIMS (m/z) [M+1$^+$] calcd for C$_{31}$H$_{23}$NO$_2$ 442.1729; found, 442.1733.

Compound 434

1.50 g (3.40 mmol) of Compound 433 was dissolved in 20 mL of toluene, and 1.42 mL (10.19 mmol) of triethylamine was added dropwise thereto. The resultant mixture was stirred at room temperature for 0.5 hours, and then, 1.26 mL (10.19 mmol) of boron trifluoride diethyl etherate was slowly added dropwise thereto. The reaction mixture was additionally stirred at room temperature for 10 hours, and an organic layer was extracted therefrom three times by using ethyl acetate and water. The extracted organic layer was dried by using magnesium sulfate, and a solvent was evaporated therefrom. Then, the residue obtained therefrom was separated and purified by silica gel column chromatography to obtain Compound 434. The obtained compound was identified by $^1$H, $^{13}$C NMR, and HR-EIMS. Yield: 1.33 g (2.72 mmol, 80%). $^1$H NMR (500 MHz, CDCl$_3$, δ, ppm): 8.43 (td, $J_{H-H}$=8.9 Hz, $J_{H-H}$=0.9 Hz, 2H), 8.32 (td, $J_{H-H}$=7.0 Hz, $J_{H-H}$=1.3 Hz, 2H), 7.66-7.60 (m, 2H), 7.38-7.24 (8H, m), 6.76 (tt, $J_{H-H}$=7.0 Hz, $J_{H-H}$=1.0 Hz, 2H), 2.20 (s, 3H), 2.19 (s, 3H). $^{13}$C NMR (125 MHz, CDCl$_3$, δ, ppm): 190.8, 140.5, 139.1, 133.3, 129.6, 127.6, 127.4, 126.0, 125.8, 125.6, 125.4, 123.1, 121.4, 119.8, 110.5, 110.1, 24.9. $^{11}$B NMR (160 MHz, CDCl$_3$, δ, ppm): 0.93. $^{19}$F NMR (470 MHz, CDCl$_3$, δ, ppm): −138.0. HR-EIMS (m/z) [M+1$^+$] calcd for C$_{31}$H$_{22}$BF$_2$NO$_2$ 490.1712; found, 490.1719.

Compound 435

1.50 g (3.40 mmol) of Compound 433 was dissolved in 20 mL of toluene, and 0.49 g (5.10 mmol) of sodium tert-butoxide was added dropwise thereto. The resultant mixture was stirred at room temperature for 1.0 hour, and then, 1.37 g (5.10 mmol) of dimesitylboron fluoride was slowly added dropwise. The reaction mixture was additionally stirred at room temperature for 10 hours, and an organic layer was extracted therefrom three times by using ethyl acetate and water. The extracted organic layer was dried by using magnesium sulfate, and a solvent was evaporated therefrom. Then, the residue obtained therefrom was separated and purified by silica gel column chromatography to obtain Compound 435. The obtained compound was identified by $^1$H, $^{13}$C NMR, and HR-EIMS. Yield: 1.22 g (1.77 mmol, 52%). $^1$H NMR (500 MHz, CDCl$_3$, δ, ppm): 8.55 (dd, $J_{H-H}$=1.5 Hz, $J_{H-H}$=0.9 Hz, 1H), 8.19 (dd, $J_{H-H}$=1.5 Hz, $J_{H-H}$=0.9 Hz, 1H), 8.16-8.12 (m, 2H), 7.68-7.41 (m, 3H), 7.50-7.44 (m, 5H), 7.35 (m, 1H), 7.20-7.16 (m, 3H), 6.80 (s, 4H), 2.33 (s, 12H), 2.05 (s, 6H), 2.00 (s, 3H), 1.90 (s, 3H). $^{13}$C NMR (125 MHz, CDCl$_3$, δ, ppm): 191.6, 179.1, 140.4, 139.7, 138.1, 132.8, 128.3, 127.9, 126.6, 126.4, 125.9, 125.6, 125.4, 123.1, 121.4, 119.8, 109.5, 109.1, 23.9, 22.7, 21.0. HR-EIMS (m/z) [M+1$^+$] calcd for C$_{49}$H$_{44}$BNO$_2$ 689.3465; found, 689.3470.

Synthesis Example 2: Synthesis of Compounds 460 to 462 and 472

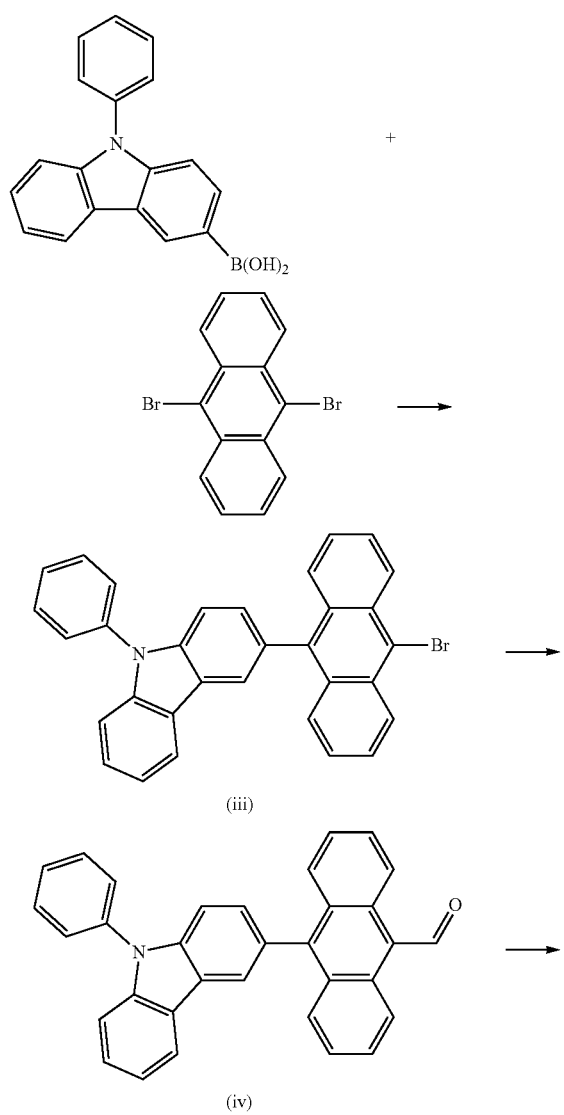

-continued

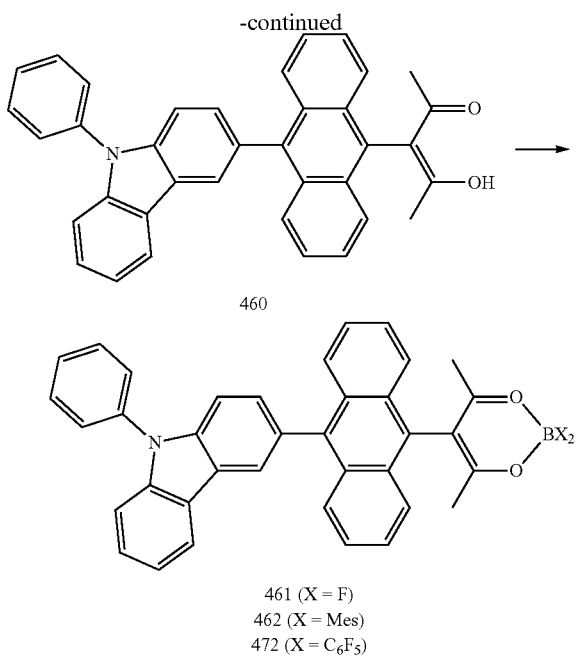

460

461 (X = F)
462 (X = Mes)
472 (X = C₆F₅)

[Intermediate (iii)]

10.0 g (34.83 mmol) of (9-phenyl-9H-carbazol-3-yl)boronic acid, 12.90 g (38.31 mmol) of 9,10-dibromoanthracene, 14.40 g (104.49 mmol) of potassium carbonate, and 2.00 g (1.74 mmol) of tetrakis(triphenylphosphine)palladium(0) were dissolved in a mixed solvent of 260 mL of tetrahydrofuran and 80 mL of water, and the reaction mixture was heated to a temperature of 100° C. and stirred for 10 hours. The reaction mixture was cooled to room temperature, and an organic layer was extracted therefrom three times by using dichloromethane and water. The extracted organic layer was dried by using magnesium sulfate, and a solvent was evaporated therefrom. Then, the residue obtained therefrom was separated and purified by silica gel column chromatography to obtain Intermediate (iii). The obtained compound was identified by $^1$H, $^{13}$C NMR, and HR-EIMS. Yield: 13.89 g (27.86 mmol, 80%). HR-EIMS (m/z) [M⁺] calcd for $C_{32}H_{20}BrN$ 497.0779; found, 497.0783.

[Intermediate (iv)]

10.00 g (20.06 mmol) of Intermediate (iii) was dissolved in 250 mL of tetrahydrofuran solvent, and the reactant was cooled to a temperature of −78° C. 8.82 mL (22.06 mmol) of N-Butyl lithium (2.5 M solution in hexane) solution was slowly added dropwise to the reactant and stirred at the same temperature for 1 hour. Then, 3.1 mL (40.12 mmol) of N,N-dimethylformamide was added dropwise to the reaction mixture. The resultant mixture was heated to room temperature and stirred for 10 hours. After the reaction was completed, an organic layer was extracted therefrom three times by using dichloromethane and water. The extracted organic layer was dried by using magnesium sulfate, and a solvent was evaporated therefrom. Then, the residue obtained therefrom was separated and purified by silica gel column chromatography to obtain Intermediate (iv). The obtained compound was identified by $^1$H, $^{13}$C NMR, and HR-EIMS. Yield: 6.28 g (14.04 mmol, 70%). HR-EIMS (m/z) [M+1⁺] calcd for $C_{33}H_{21}NO$ 448.1623; found, 448.16230.

Compound 460

5.00 g (11.17 mmol) of Intermediate (iv) was dissolved in 7.04 g (33.51 mmol) of 2,2,2,2-tetramethoxy-4,5-dimethyl-1,3,2-dioxaphospholene and 5 mL of dichloromethane, and the reaction mixture was heated to a temperature of 70° C. and stirred for 24 hours. Then, the reaction mixture was cooled to room temperature, and 5 mL of methanol was added dropwise thereto. Then, the resultant mixture was heated at a temperature of 70° C. for 6 hours. The reaction mixture was cooled to room temperature, and an organic layer was extracted therefrom three times by using dichloromethane and water. The extracted organic layer was dried by using magnesium sulfate, and a solvent was evaporated therefrom. Then, the residue obtained therefrom was separated and purified by silica gel column chromatography to obtain Compound 460. The obtained compound was identified by $^1$H, $^{13}$C NMR, and HR-EIMS. Yield: 3.76 g (7.26 mmol, 65%). $^1$H NMR (500 MHz, CDCl₃, δ, ppm): 16.65 (s, 1H), 8.24 (d, $J_{H-H}$=1.1 Hz, 1H), 8.10 (d, $J_{H-H}$=7.6 Hz, 1H), 8.05 (d, $J_{H-H}$=8.7 Hz, 2H), 7.84 (d, $J_{H-H}$=8.70 Hz, 2H), 7.73-7.62 (m, 5H), 7.54-7.49 (m, 5H), 7.45 (td, $J_{H-H}$=7.6 Hz, $J_{H-H}$=1.1 Hz, 1H), 7.36 (dd, $J_{H-H}$=8.70, $J_{H-H}$=1.1 Hz, 2H), 7.29 (td, $J_{H-H}$=7.4 Hz, $J_{H-H}$=1.1 Hz, 1H), 1.73 (s, 3H), 1.72 (s, 3H). $^{13}$C NMR (125 MHz, CDCl₃, δ, ppm): 192.4, 192.3, 141.5, 140.4, 139.1, 137.8, 134.1, 131.0, 130.1, 130.0, 129.8, 129.2, 128.1, 127.7, 127.2, 126.3, 126.2, 125.4, 125.2, 123.5, 123.2, 123.1, 120.4, 120.2, 110.1, 109.7, 23.9. HR-EIMS (m/z) [M+1⁺] calcd for $C_{37}H_{26}NO_2$ 518.2042; found, 518.2046.

Compound 461

1.50 g (2.90 mmol) of Compound 460 was dissolved in 20 mL of toluene, and 1.21 mL (8.70 mmol) of triethylamine was added dropwise thereto. The resultant mixture was stirred at room temperature for 0.5 hours, and then, 1.07 mL (8.70 mmol) of boron trifluoride diethyl etherate was slowly added dropwise thereto. The reaction mixture was additionally stirred at room temperature for 10 hours, and an organic layer was extracted therefrom three times by using ethyl acetate and water. The extracted organic layer was dried by using magnesium sulfate, and a solvent was evaporated therefrom. Then, the residue obtained therefrom was separated and purified by silica gel column chromatography to obtain Compound 461. The obtained compound was identified by $^1$H, $^{13}$C NMR, and HR-EIMS. Yield: 1.39 g (2.47 mmol, 85%). $^1$H NMR (500 MHz, CDCl₃, δ, ppm): 8.25 (d, $J_{H-H}$=1.2 Hz, 1H), 8.10 (d, $J_{H-H}$=7.6 Hz, 1H), 8.05 (d, $J_{H-H}$=8.7 Hz, 2H), 7.84 (d, $J_{H-H}$=8.70 Hz, 2H), 7.73-7.62 (m, 5H), 7.54-7.49 (m, 5H), 7.45 (td, $J_{H-H}$=7.6 Hz, $J_{H-H}$=1.1 Hz, 1H), 7.36 (dd, $J_{H-H}$=8.70, $J_{H-H}$=1.1 Hz, 2H), 7.29 (td, $J_{H-H}$=7.4 Hz, $J_{H-H}$=1.1 Hz, 1H), 1.73 (s, 3H), 1.72 (s, 3H). $^{11}$B NMR (160 MHz, Acetone-d₆, δ, ppm): 0.90. $^{19}$F NMR (470 MHz, Acetone-d₆, δ, ppm): −140.0. HR-EIMS (m/z) [M+1⁺] calcd for $C_{37}H_{26}BF_2NO_2$ 566.2025; found, 566.2029.

Compound 462

1.50 g (2.90 mmol) of Compound 460 was dissolved in 20 mL of toluene, and 0.42 g (4.35 mmol) of sodium tert-butoxide was added dropwise thereto. The resultant mixture was stirred at room temperature for 1.0 hour, and 1.17 g (4.35 mmol) of dimesitylboron fluoride was slowly added dropwise thereto. The reaction mixture was additionally stirred at room temperature for 10 hours, and an organic layer was extracted therefrom three times by using ethyl acetate and water. The extracted organic layer was dried by using magnesium sulfate, and a solvent was evaporated therefrom. Then, the residue obtained therefrom was separated and purified by silica gel column chromatography to obtain Compound 462. The obtained compound was identified by $^1$H, $^{13}$C NMR, and HR-EIMS. Yield: 1.22 g (1.60 mmol, 55%). $^1$H NMR (500 MHz, CDCl$_3$, δ, ppm): 8.26 (d, $J_{H-H}$=1.2 Hz, 1H), 8.08 (d, $J_{H-H}$=7.6 Hz, 1H), 8.06 (d, $J_{H-H}$=8.7 Hz, 2H), 7.82 (d, $J_{H-H}$=8.70 Hz, 2H), 7.71-7.60 (m, 5H), 7.54-7.49 (m, 5H), 7.45 (td, $J_{H-H}$=7.6 Hz, $J_{H-H}$=1.1 Hz, 1H), 7.30 (dd, $J_{H-H}$=8.70, $J_{H-H}$=1.1 Hz, 2H), 7.26 (td, $J_{H-H}$=7.4 Hz, $J_{H-H}$=1.1 Hz, 1H), 7.00-6.90 (m, 4H), 2.33 (s, 6H), 2.31 (s, 6H), 2.15 (s, 6H), 1.73 (s, 3H), 1.72 (s, 3H). $^{11}$B NMR (160 MHz, Acetone-d$_6$, δ, ppm): 10.50. HR-EIMS (m/z) [M+1$^+$] calcd for C$_{55}$H$_{48}$BNO$_2$ 766.3778; found, 766.3782.

Compound 472

1.50 g (2.90 mmol) of Compound 460 was dissolved in 20 mL of toluene, and 0.42 g (4.35 mmol) of sodium tert-butoxide was added dropwise thereto. The resultant mixture was stirred at room temperature for 1.0 hour, and 2.23 g (4.35 mmol) of tris(pentafluorophenyl)borane was slowly added dropwise thereto. The reaction mixture was additionally stirred at room temperature for 10 hours, and an organic layer was extracted therefrom three times by using ethyl acetate and water. The extracted organic layer was dried by using magnesium sulfate, and a solvent was evaporated therefrom. Then, the residue obtained therefrom was separated and purified by silica gel column chromatography to obtain Compound 472. The obtained compound was identified by $^1$H, $^{13}$C NMR, and HR-EIMS. Yield: 1.57 g (1.83 mmol, 63%). $^1$H NMR (500 MHz, CDCl$_3$, δ, ppm): 8.23 (d, $J_{H-H}$=1.2 Hz, 1H), 8.11 (d, $J_{H-H}$=7.6 Hz, 1H), 8.07 (d, $J_{H-H}$=8.7 Hz, 2H), 7.88 (d, $J_{H-H}$=8.70 Hz, 2H), 7.70-7.61 (m, 5H), 7.55-7.40 (m, 5H), 7.41 (td, $J_{H-H}$=7.6 Hz, $J_{H-H}$=1.1 Hz, 1H), 7.32 (dd, $J_{H-H}$=8.70, $J_{H-H}$=1.1 Hz, 2H), 7.20 (td, $J_{H-H}$=7.4 Hz, $J_{H-H}$=1.1 Hz, 1H), 1.68 (s, 3H), 1.65 (s, 3H). $^{11}$B NMR (160 MHz, Acetone-d$_6$, δ, ppm): 3.50. HR-EIMS (m/z) [M+1$^+$] calcd for C$_{49}$H$_{26}$BF$_{10}$NO$_2$ 862.1897; found, 862.1903.

Comparative Example 1

As an anode, a Corning 15 Ω/cm$^2$ (1,200 Å) ITO glass substrate was cut to a size of 50 mm×50 mm×0.7 mm, sonicated with isopropyl alcohol and pure water each for 5 minutes, and then cleaned by exposure to ultraviolet rays and ozone for 30 minutes. Then, the ITO glass substrate was provided to a vacuum deposition apparatus.

2-TNATA, which is a known compound, was vacuum-deposited on the ITO glass substrate to form a hole injection layer having a thickness of 600 Å, and NPB, which is a hole transport compound, was vacuum-deposited on the hole injection layer to form a hole transport layer having a thickness of 300 Å

9,10-di-naphthalene-2-yl-anthracene (ADN), which is a known blue fluorescent host, and N,N,N',N'-tetraphenyl-pyrene-1,6-diamine (TPD), which is a known blue fluorescent dopant, were co-deposited on the hole transport layer at a weight ratio of 98:2 to form an emission layer having a thickness of 300 Å

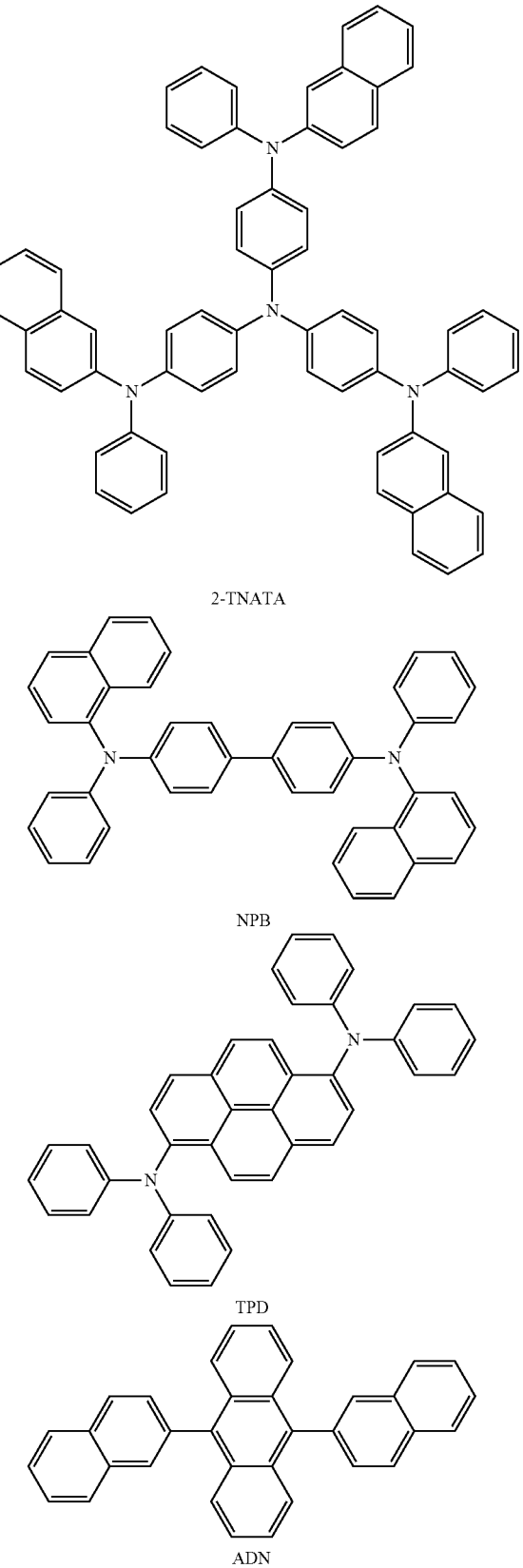

2-TNATA

NPB

TPD

ADN

Then, Alq$_3$ was deposited on the emission layer to form an electron transport layer having a thickness of 300 Å LiF, which is an alkali metal halide, was deposited the electron transport layer to form an electron injection layer having a thickness of 10 Å and Al was vacuum-deposited on the electron injection layer to form a LiF/Al electrode (cathode electrode) having a thickness of 3,000 Å thereby completing the manufacture of an organic light-emitting device.

Example 1

An organic light-emitting device was manufactured in the same manner as in Comparative Example 1, except that an emission layer was formed by co-depositing ADN (host), Compound 433 (Dopant 2), and TPD (Dopant 1) at a weight ratio of 79:20:1 in forming a blue emission layer.

Example 2

An organic light-emitting device was manufactured in the same manner as in Comparative Example 1, except that an emission layer was formed by co-depositing ADN, Compound 434, and TPD at a weight ratio of 79:20:1 in forming a blue emission layer.

Example 3

An organic light-emitting device was manufactured in the same manner as in Comparative Example 1, except that an emission layer was formed by co-depositing ADN, Compound 435, and TPD at a weight ratio of 79:20:1 in forming a blue emission layer.

Example 4

An organic light-emitting device was manufactured in the same manner as in Comparative Example 1, except that an emission layer was formed by co-depositing ADN, Compound 460, and TPD at a weight ratio of 79:20:1 in forming a blue emission layer.

Example 5

An organic light-emitting device was manufactured in the same manner as in Comparative Example 1, except that an emission layer was formed by co-depositing ADN, Compound 461, and TPD at a weight ratio of 79:20:1 in forming a blue emission layer.

Example 6

An organic light-emitting device was manufactured in the same manner as in Comparative Example 1, except that an emission layer was formed by co-depositing ADN, Compound 462, and TPD at a weight ratio of 79:20:1 in forming a blue emission layer.

Example 7

An organic light-emitting device was manufactured in the same manner as in Comparative Example 1, except that an emission layer was formed by co-depositing ADN, Compound 472, and TPD at a weight ratio 79:20:1 in forming a blue emission layer.

Results of Examples and Comparative Example are shown in Table 1.

TABLE 1

| | Dopant 2 | Driving voltage (V) | Current density (mA/cm$^2$) | Luminance (cd/m$^2$) | Efficiency (cd/A) | Emission color | Half lifespan (hr @100 mA/cm$^2$) |
|---|---|---|---|---|---|---|---|
| Comparative Example 1 | — | 6.01 | 50 | 3356 | 6.53 | Blue | 320 |
| Example 1 | Compound 433 | 5.97 | 50 | 3378 | 6.72 | Blue | 316 |
| Example 2 | Compound 434 | 5.85 | 50 | 3415 | 7.05 | Blue | 355 |
| Example 3 | Compound 435 | 5.87 | 50 | 3369 | 6.85 | Blue | 340 |
| Example 4 | Compound 460 | 5.98 | 50 | 3393 | 6.75 | Blue | 310 |
| Example 5 | Compound 461 | 5.84 | 50 | 3415 | 7.06 | Blue | 360 |
| Example 6 | Compound 462 | 5.89 | 50 | 3391 | 6.87 | Blue | 345 |
| Example 7 | Compound 472 | 5.84 | 50 | 3425 | 7.10 | Blue | 355 |

When Compounds having the structure of Formula 1 according to one or more embodiments were used as Dopant 2, all Examples exhibited a low driving voltage and excellent I-V-L characteristics with improved efficiency, as compared with the Comparative Example. In particular, Examples exhibited an excellent lifespan improvement effect. From these results, it can be seen that compounds according to one or more embodiments are suitable for use as an electron transport material.

An organic light-emitting device according to an embodiment may have high efficiency, a low driving voltage, high luminance, and a long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope as defined by the following claims.

What is claimed is:

1. A compound represented by Formula 1:

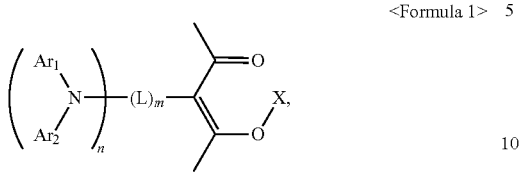

<Formula 1> wherein, in Formula 1, $Ar_1$ and $Ar_2$ are each independently selected from a substituted or unsubstituted $C_6$-$C_{60}$ aryl group, and a substituted or unsubstituted $C_1$-$C_{60}$ heteroaryl group, and a substituted or unsubstituted monovalent non-aromatic condensed polycyclic group, L is selected from a substituted or unsubstituted $C_6$-$C_{60}$ arylene group and a substituted or unsubstituted $C_1$-$C_{60}$ heteroarylene group, m is an integer from 1 to 5, when m is two or more, two or more L(s) are identical to or different from each other, n is an integer from 1 to 3, when n is two or more, two or more $Ar_1$(s) are identical to or different from each other, and two or more $Ar_2$(s) are identical to or different from each other, X is hydrogen or a boron compound, at least one substituent of the substituted $C_6$-$C_{60}$ aryl group, the substituted $C_1$-$C_{60}$ heteroaryl group, the substituted monovalent non-aromatic condensed polycyclic group, the substituted $C_6$-$C_{60}$ arylene group, and the substituted $C_1$-$C_{60}$ heteroarylene group, is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{60}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and $Q_{11}$ to $Q_{17}$ and $Q_{21}$ to $Q_{27}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The compound of claim 1, wherein
X in Formula 1 is hydrogen, $BF_2$, $BCl_2$, $BBr_2$, $B_{12}$, or $BR_{11}R_{12}$, and
$R_{11}$ and $R_{12}$ are each a substituted or unsubstituted $C_6$-$C_{60}$ aryl group.

3. The compound of claim 1, wherein
X in Formula 1 is hydrogen, $BF_2$, $BMes_2$, or $B(C_6F_5)_2$.

4. The compound of claim 1, wherein
two neighboring substituents selected from $Ar_1$, $Ar_2$, and L in Formula 1 are linked to form a ring.

5. The compound of claim 1, wherein $Ar_1$ and $Ar_2$ in Formula 1 are each independently represented by one of Formulae 2a to 2c:

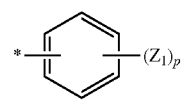

2a

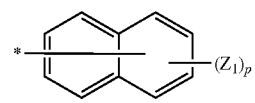

2b

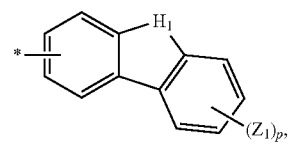

2c wherein, in Formulae 2a to 2c, $H_1$ is O, S, $NR_{21}$, or $CR_{22}R_{23}$, $R_{21}$ to $R_{23}$ and $Z_1$ are each independently selected from hydrogen, deuterium, halogen, a substituted or unsubstituted $C_1$-$C_{20}$ alkyl group, a substituted or unsubstituted $C_1$-$C_{20}$ alkenyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, p is an integer from 1 to 7, when p is two or more, two or more $Z_1$(s) are identical to or different from each other, and

*indicates a binding site.

6. The compound of claim 1, wherein L in Formula 1 is represented by one of Formulae 3a to 3g :

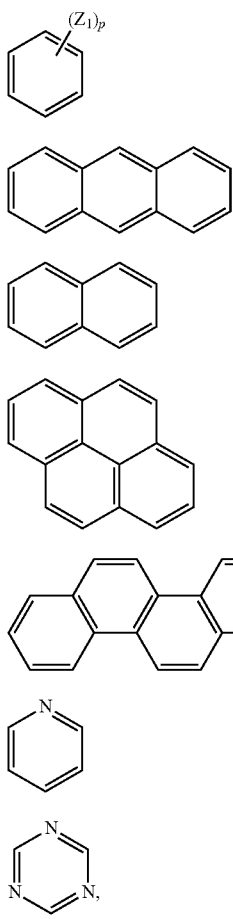

wherein, in Formulae 3a to 3g , $Z_1$ is selected from hydrogen, deuterium, halogen, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group, and when p is two or more, two or more $Z_1$(s) are identical to or different from each other.

7. The compound of claim 4, wherein the compound represented by Formula 1 is represented by Formula 2:

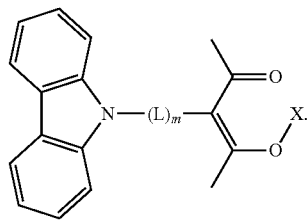

<Formula 2>

8. The compound of claim 4, wherein the compound represented by Formula 1 is represented by Formula 3:

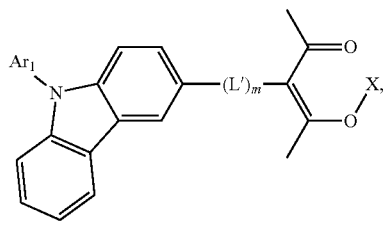

<Formula 3> wherein L' in Formula 3 is the same as described in connection with L.

9. The compound of claim 1, wherein the compound represented by Formula 1 is one selected from the following compounds:

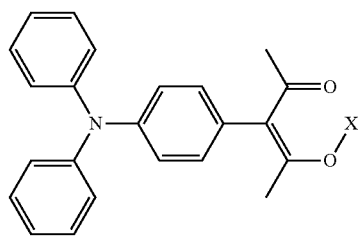

1 (X = H)
2 (X = BF$_2$)
3 (X = BMes$_2$)

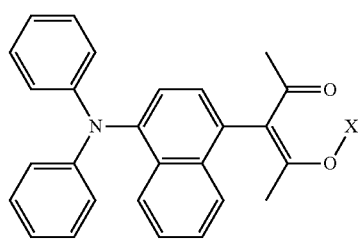

4 (X = H)
5 (X = BF$_2$)
6 (X = BMes$_2$)

-continued
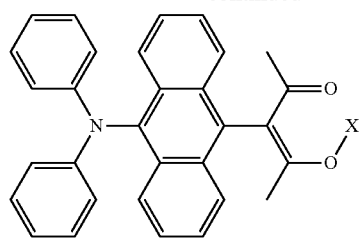
7 (X = H)
8 (X = BF$_2$)
9 (X = BMes$_2$)
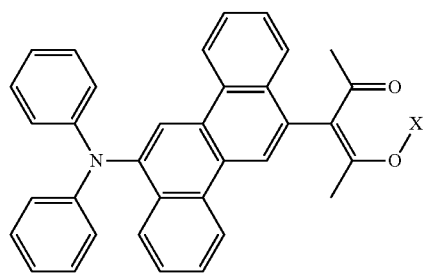
10 (X = H)
11 (X = BF$_2$)
12 (X = BMes$_2$)
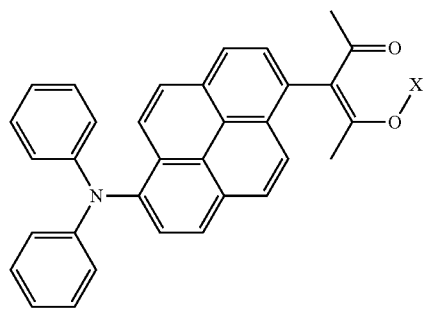
13 (X = H)
14 (X = BF$_2$)
15 (X = BMes$_2$)
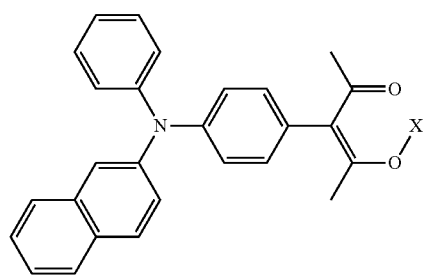
16 (X = H)
17 (X = BF$_2$)
18 (X = BMes$_2$)
-continued
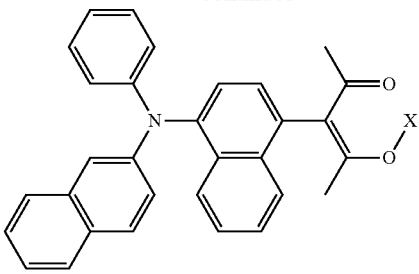
19 (X = H)
20 (X = BF$_2$)
21 (X = BMes$_2$)
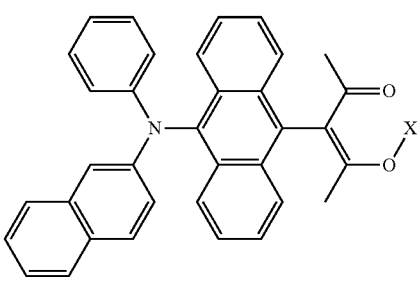
22 (X = H)
23 (X = BF$_2$)
24 (X = BMes$_2$)
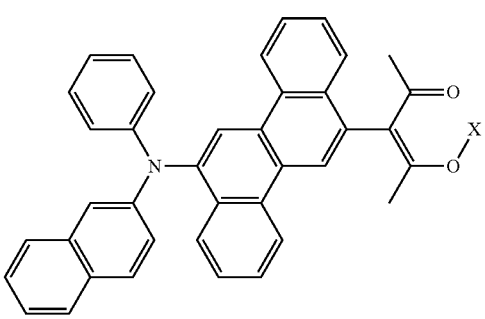
25 (X = H)
26 (X = BF$_2$)
27 (X = BMes$_2$)
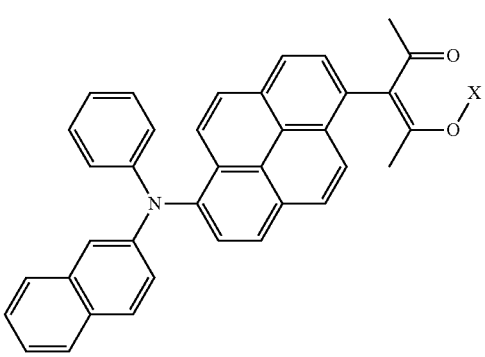
28 (X = H)
29 (X = BF$_2$)
30 (X = BMes$_2$)

-continued
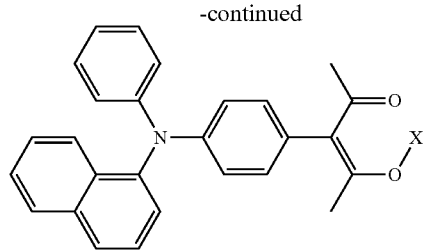
31 (X = H)
32 (X = BF₂)
33 (X = BMes₂)
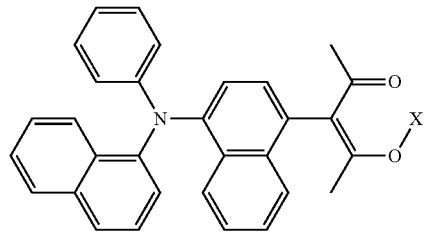
34 (X = H)
35 (X = BF₂)
36 (X = BMes₂)
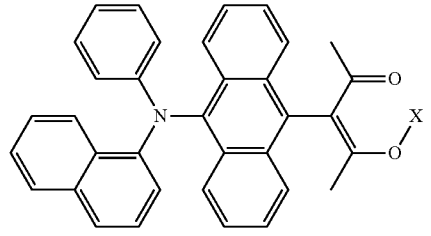
37 (X = H)
38 (X = BF₂)
39 (X = BMes₂)
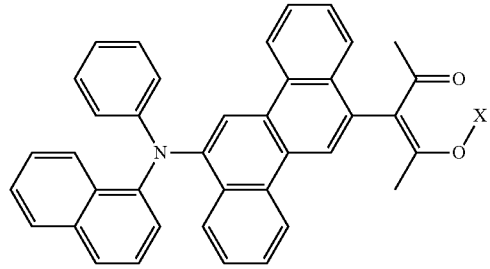
40 (X = H)
41 (X = BF₂)
42 (X = BMes₂)
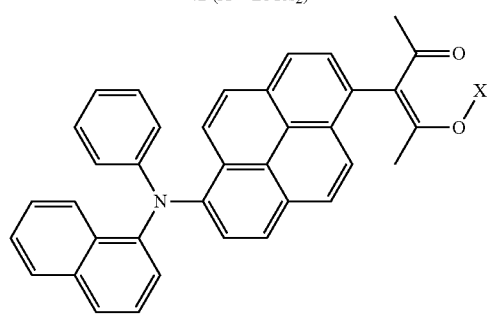
43 (X = H)
44 (X = BF₂)
45 (X = BMes₂)
-continued
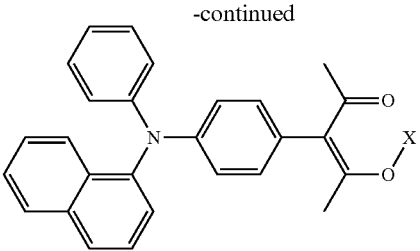
46 (X = H)
47 (X = BF₂)
48 (X = BMes₂)
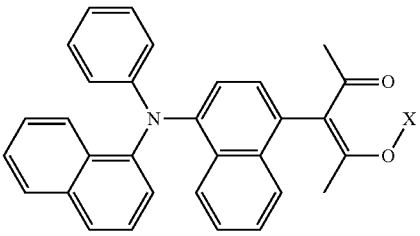
49 (X = H)
50 (X = BF₂)
51 (X = BMes₂)
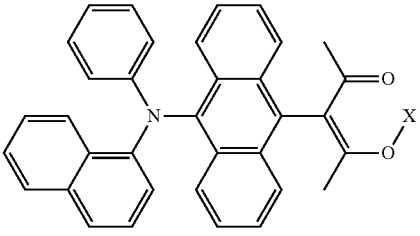
52 (X = H)
53 (X = BF₂)
54 (X = BMes₂)
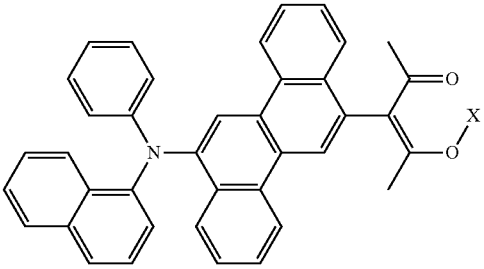
55 (X = H)
56 (X = BF₂)
57 (X = BMes₂)
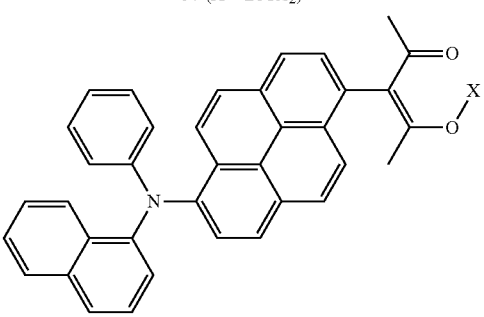
58 (X = H)
59 (X = BF₂)
60 (X = BMes₂)

-continued
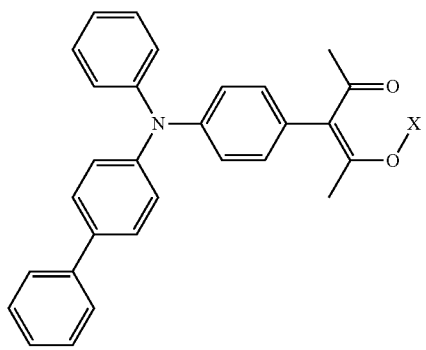
61 (X = H)
62 (X = BF$_2$)
63 (X = BMes$_2$)
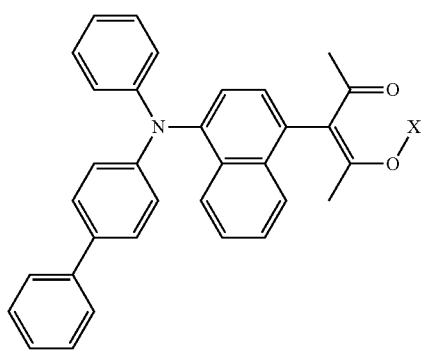
64 (X = H)
65 (X = BF$_2$)
66 (X = BMes$_2$)
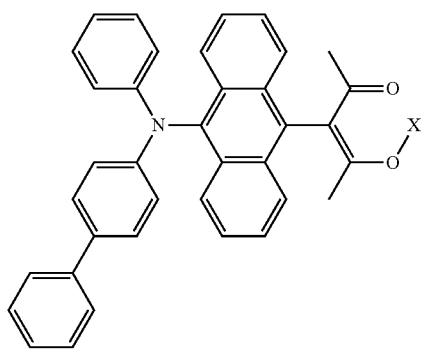
67 (X = H)
68 (X = BF$_2$)
69 (X = BMes$_2$)
-continued
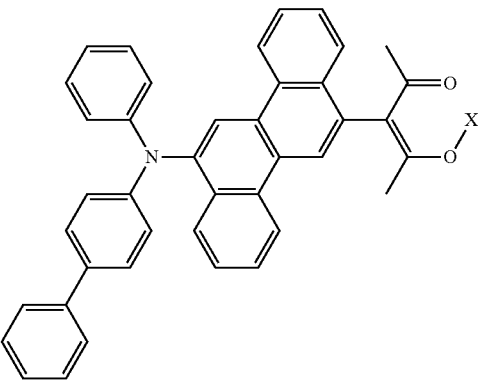
70 (X = H)
71 (X = BF$_2$)
72 (X = BMes$_2$)
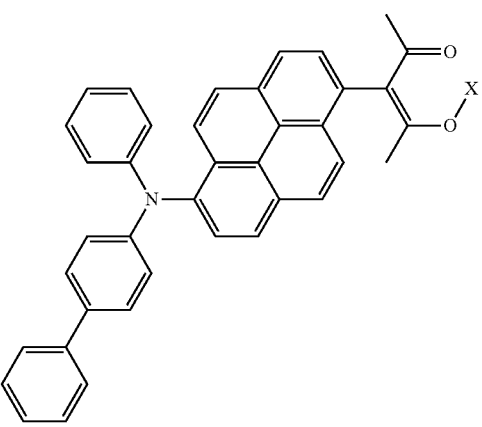
73 (X = H)
74 (X = BF$_2$)
75 (X = BMes$_2$)
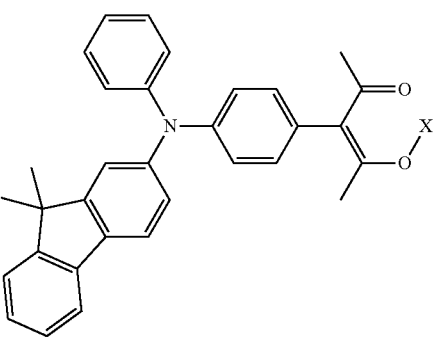
76 (X = H)
77 (X = BF$_2$)
78 (X = BMes$_2$)

145
-continued
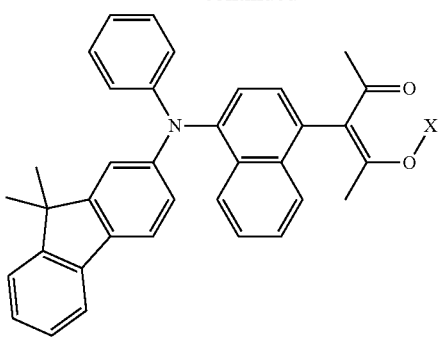
79 (X = H)
80 (X = BF$_2$)
81 (X = BMes$_2$)
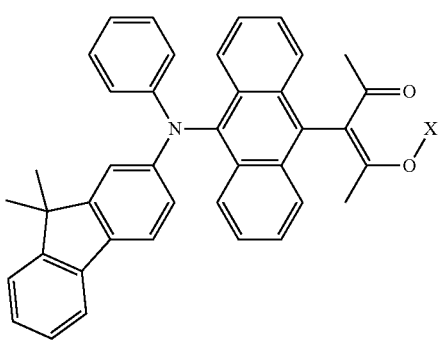
82 (X = H)
83 (X = BF$_2$)
84 (X = BMes$_2$)
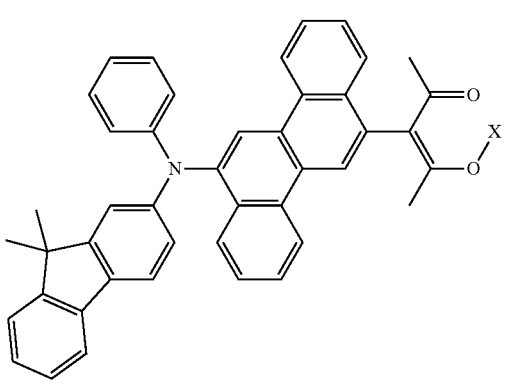
85 (X = H)
86 (X = BF$_2$)
87 (X = BMes$_2$)
146
-continued
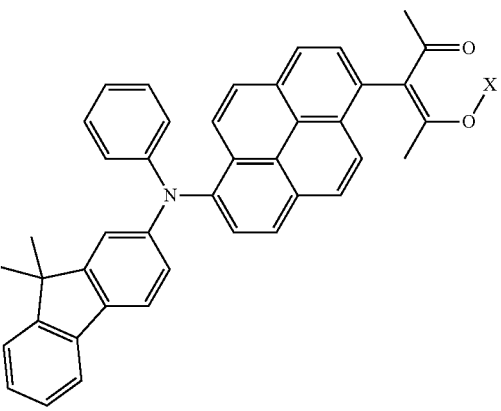
88 (X = H)
89 (X = BF$_2$)
90 (X = BMes$_2$)
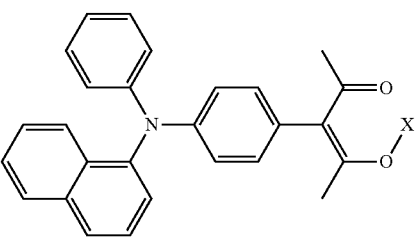
91 (X = H)
92 (X = BF$_2$)
93 (X = BMes$_2$)
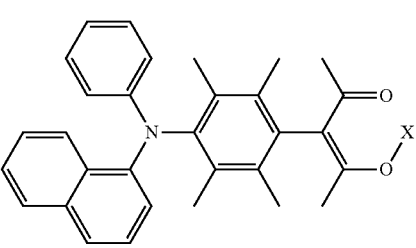
94 (X = H)
95 (X = BF$_2$)
96 (X = BMes$_2$)
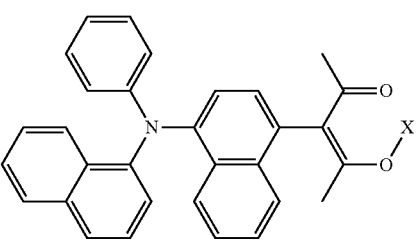
97 (X = H)
98 (X = BF$_2$)
99 (X = BMes$_2$)

147
-continued
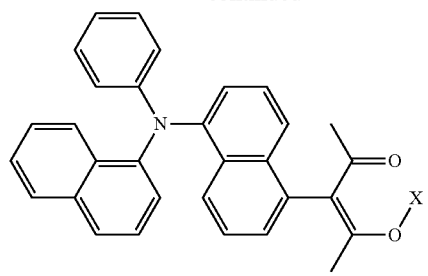
100 (X = H)
101 (X = BF$_2$)
102 (X = BMes$_2$)
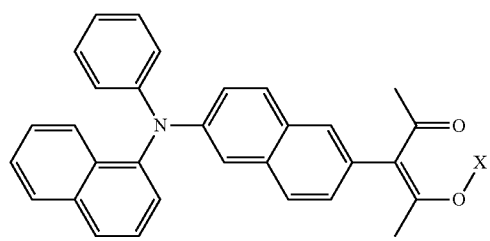
103 (X = H)
104 (X = BF$_2$)
105 (X = BMes$_2$)
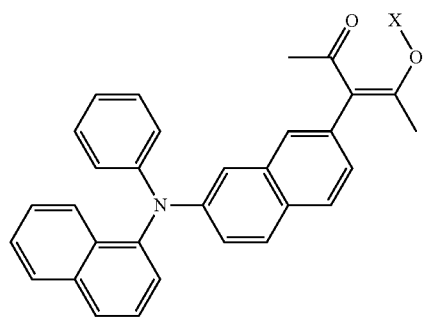
106 (X = H)
107 (X = BF$_2$)
108 (X = BMes$_2$)
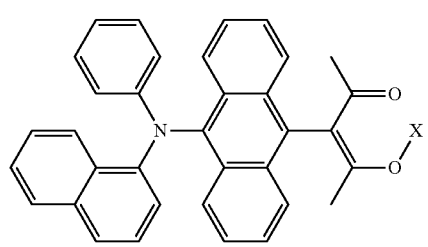
109 (X = H)
110 (X = BF$_2$)
111 (X = BMes$_2$)
148
-continued
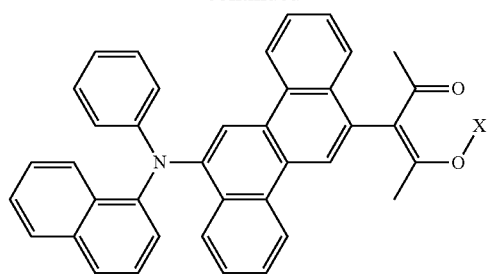
112 (X = H)
113 (X = BF$_2$)
114 (X = BMes$_2$)
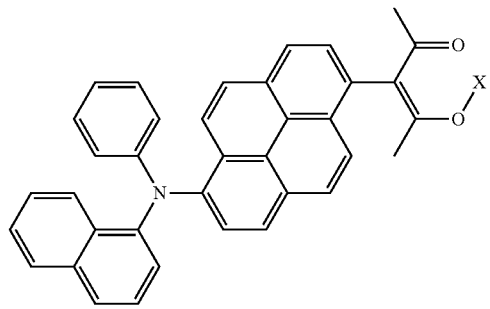
115 (X = H)
116 (X = BF$_2$)
117 (X = BMes$_2$)
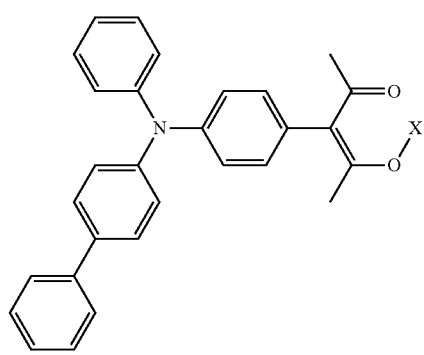
118 (X = H)
119 (X = BF$_2$)
120 (X = BMes$_2$)
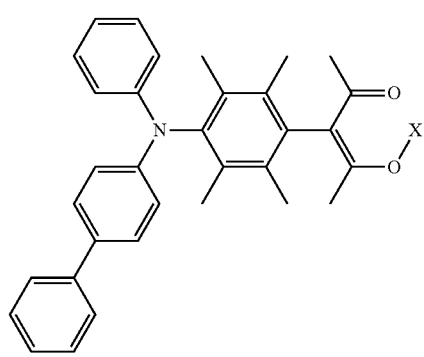
121 (X = H)
122 (X = BF$_2$)
123 (X = BMes$_2$)

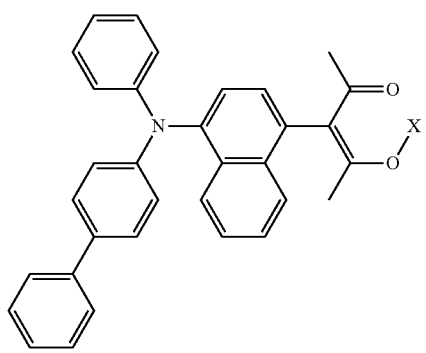
124 (X = H)
125 (X = BF$_2$)
126 (X = BMes$_2$)
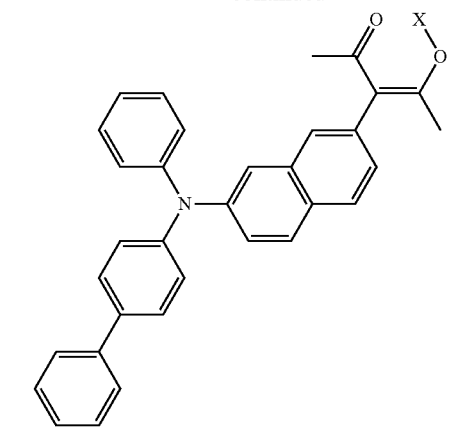
133 (X = H)
134 (X = BF$_2$)
135 (X = BMes$_2$)
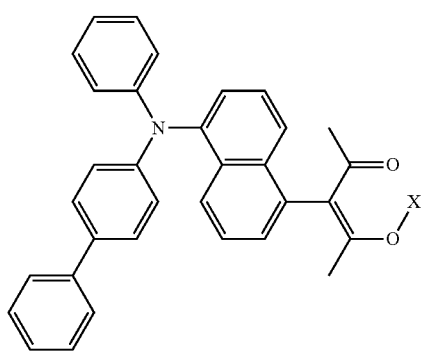
127 (X = H)
128 (X = BF$_2$)
129 (X = BMes$_2$)
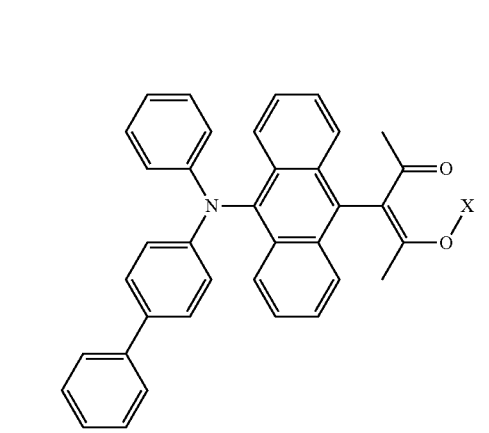
136 (X = H)
137 (X = BF$_2$)
138 (X = BMes$_2$)
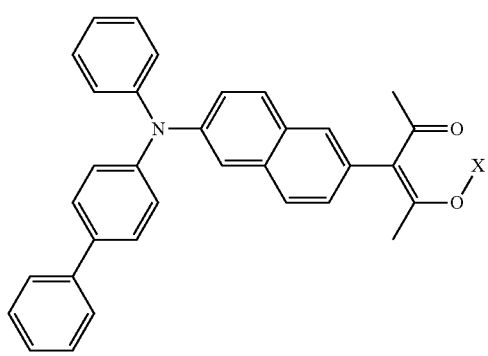
130 (X = H)
131 (X = BF$_2$)
132 (X = BMes$_2$)
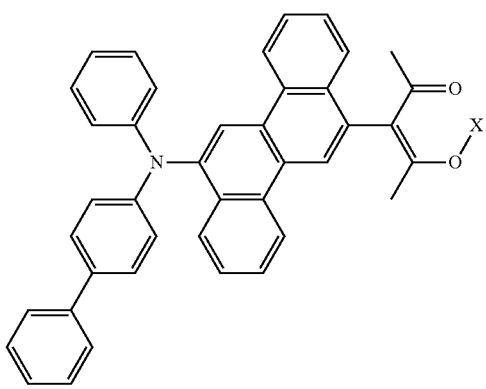
139 (X = H)
140 (X = BF$_2$)
141 (X = BMes$_2$)

151
-continued
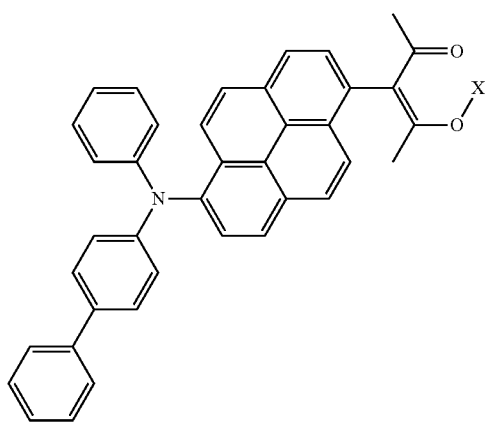
142 (X = H)
143 (X = BF₂)
144 (X = BMes₂)
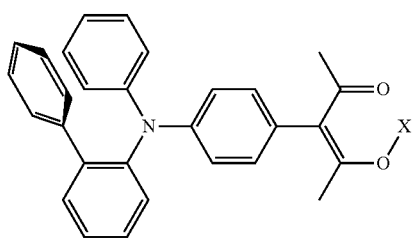
145 (X = H)
146 (X = BF₂)
147 (X = BMes₂)
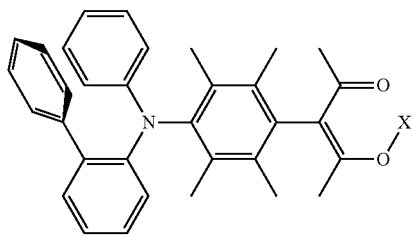
148 (X = H)
149 (X = BF₂)
150 (X = BMes₂)
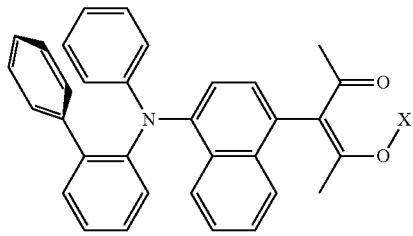
151 (X = H)
152 (X = BF₂)
153 (X = BMes₂)
152
-continued
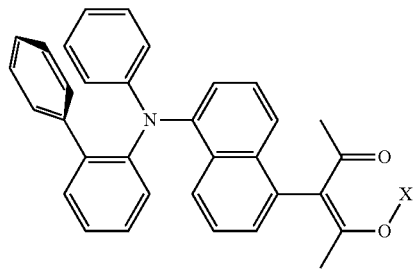
154 (X = H)
155 (X = BF₂)
156 (X = BMes₂)
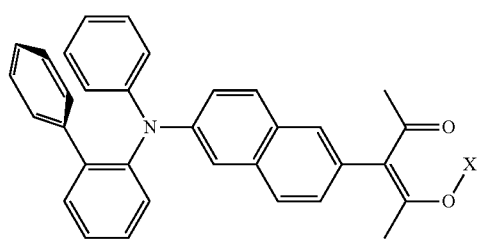
157 (X = H)
158 (X = BF₂)
159 (X = BMes₂)
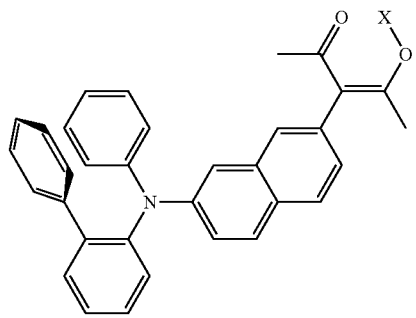
160 (X = H)
161 (X = BF₂)
162 (X = BMes₂)
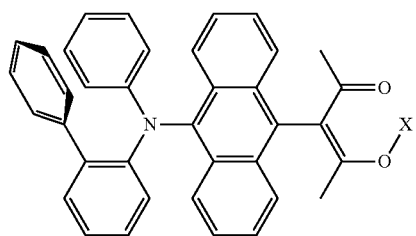
163 (X = H)
164 (X = BF₂)
165 (X = BMes₂)

-continued
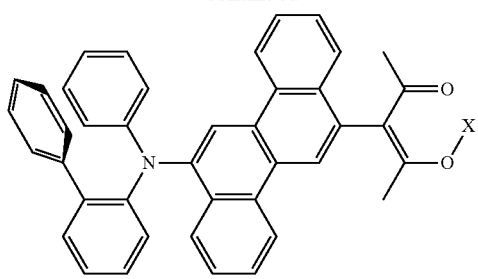
166 (X = H)
167 (X = BF$_2$)
168 (X = BMes$_2$)
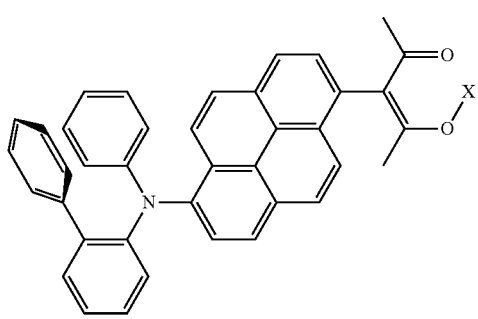
169 (X = H)
170 (X = BF$_2$)
171 (X = BMes$_2$)
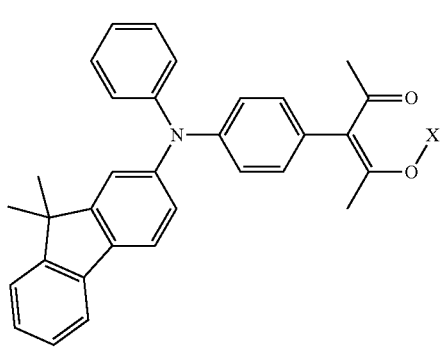
172 (X = H)
173 (X = BF$_2$)
174 (X = BMes$_2$)
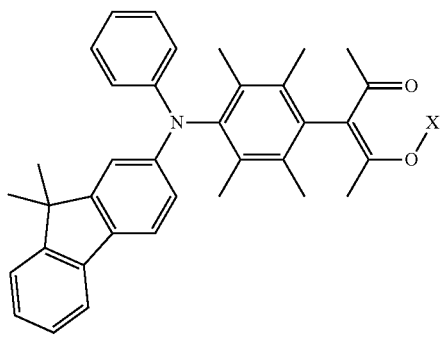
175 (X = H)
176 (X = BF$_2$)
177 (X = BMes$_2$)
-continued
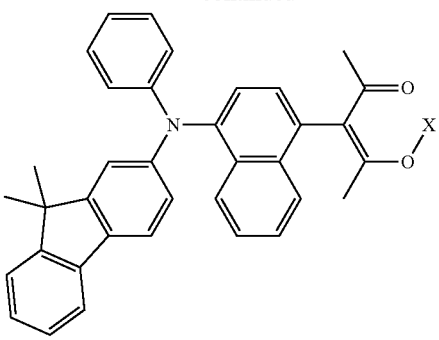
178 (X = H)
179 (X = BF$_2$)
180 (X = BMes$_2$)
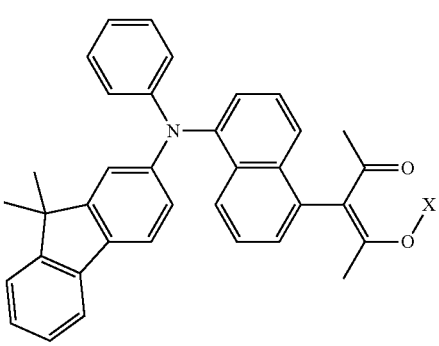
181 (X = H)
182 (X = BF$_2$)
183 (X = BMes$_2$)
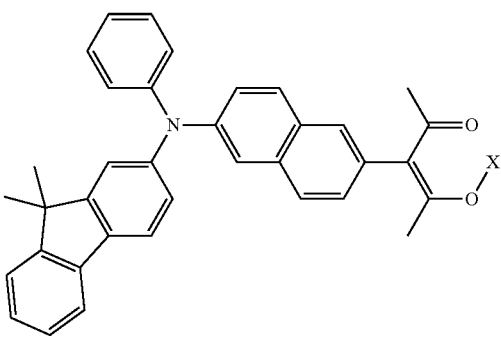
184 (X = H)
185 (X = BF$_2$)
186 (X = BMes$_2$)

-continued
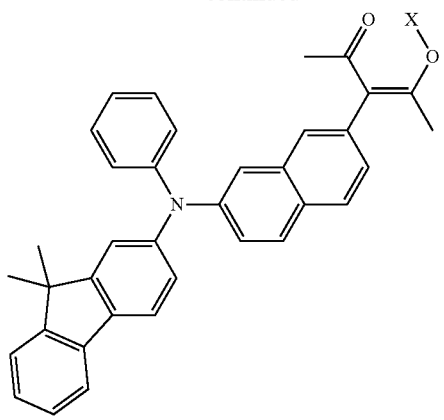
187 (X = H)
188 (X = BF₂)
189 (X = BMes₂)
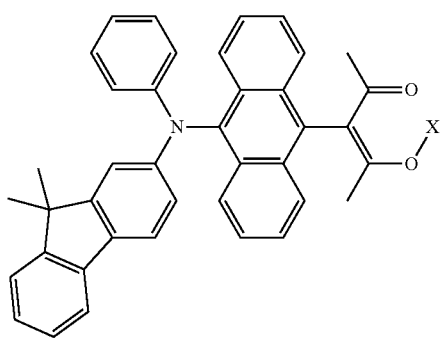
190 (X = H)
191 (X = BF₂)
192 (X = BMes₂)
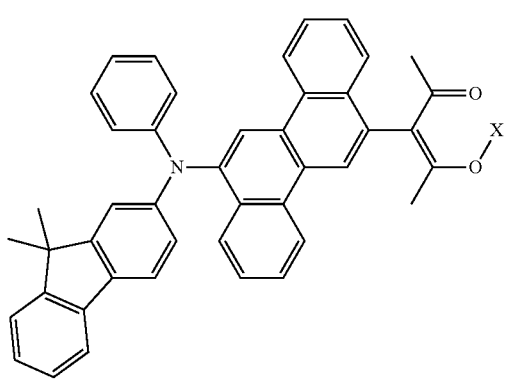
193 (X = H)
194 (X = BF₂)
195 (X = BMes₂)
-continued
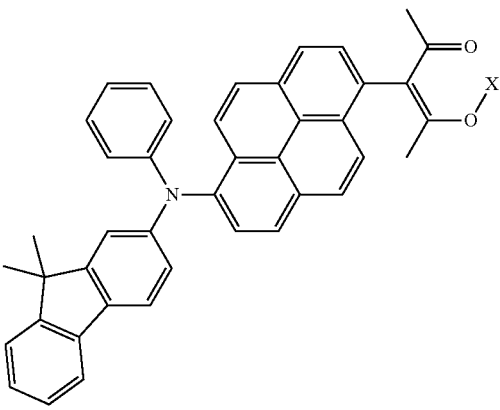
196 (X = H)
197 (X = BF₂)
198 (X = BMes₂)
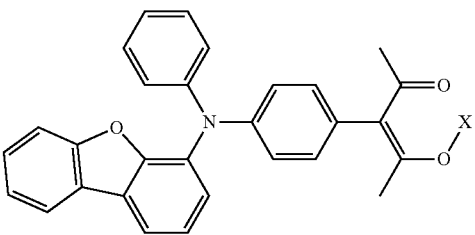
199 (X = H)
200 (X = BF₂)
201 (X = BMes₂)
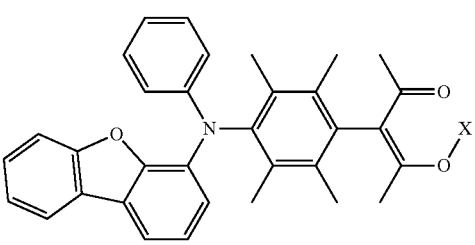
202 (X = H)
203 (X = BF₂)
204 (X = BMes₂)
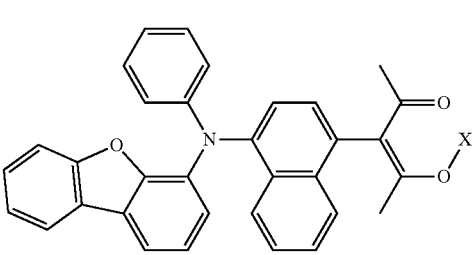
205 (X = H)
206 (X = BF₂)
207 (X = BMes₂)

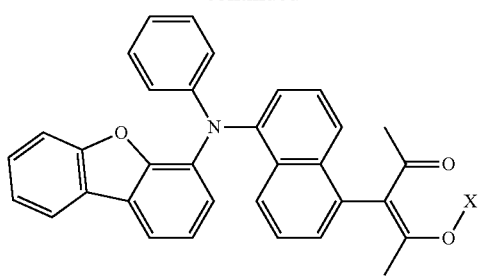
208 (X = H)
209 (X = BF₂)
210 (X = BMes₂)
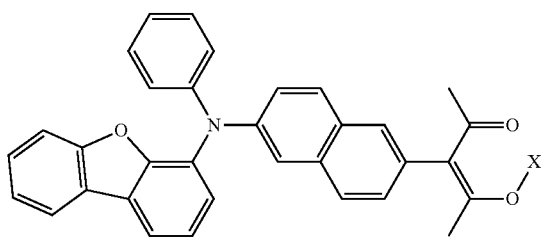
211 (X = H)
212 (X = BF₂)
213 (X = BMes₂)
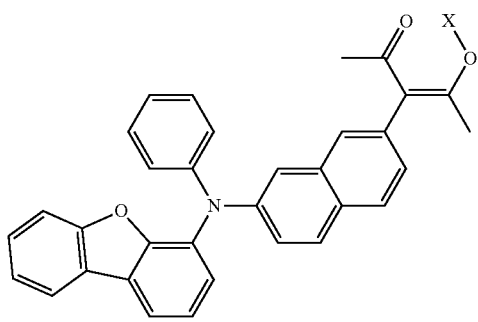
214 (X = H)
215 (X = BF₂)
216 (X = BMes₂)
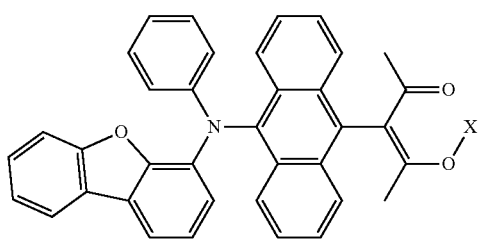
217 (X = H)
218 (X = BF₂)
219 (X = BMes₂)
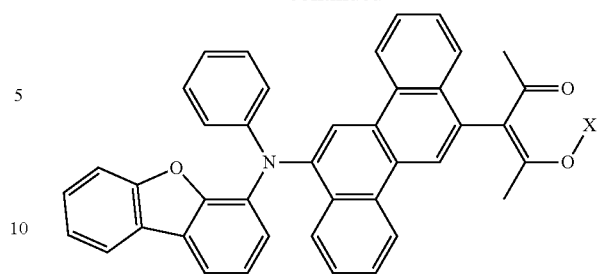
220 (X = H)
221 (X = BF₂)
222 (X = BMes₂)
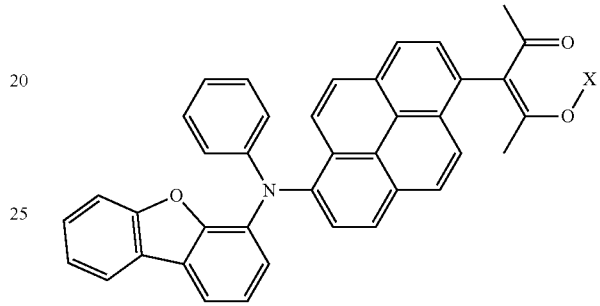
223 (X = H)
224 (X = BF₂)
225 (X = BMes₂)
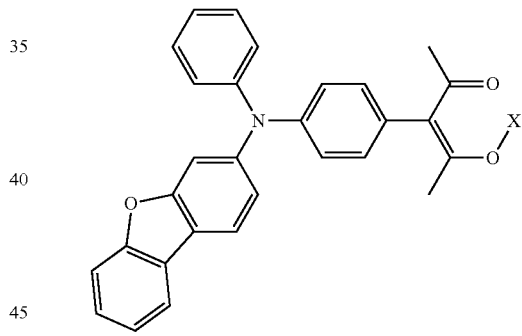
226 (X = H)
227 (X = BF₂)
228 (X = BMes₂)
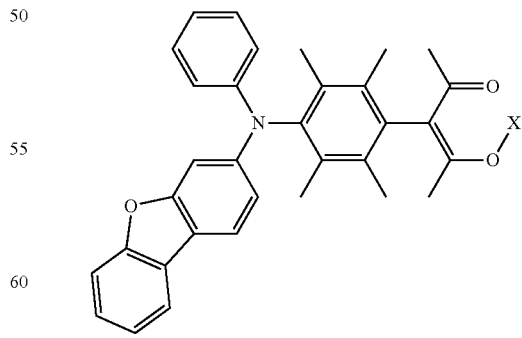
229 (X = H)
230 (X = BF₂)
231 (X = BMes₂)

159
-continued
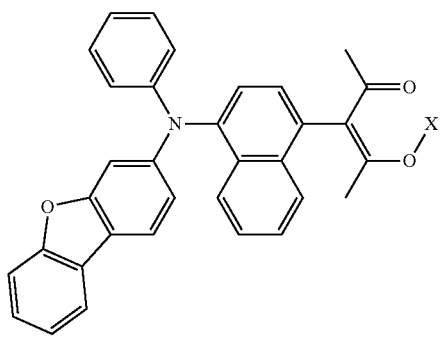
232 (X = H)
233 (X = BF$_2$)
234 (X = BMes$_2$)
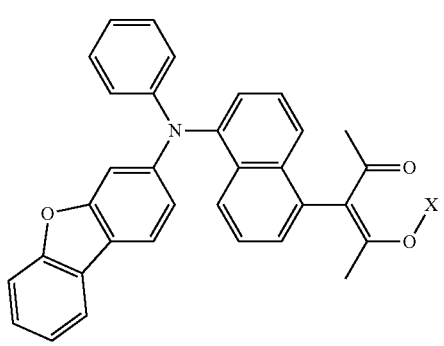
235 (X = H)
236 (X = BF$_2$)
237 (X = BMes$_2$)
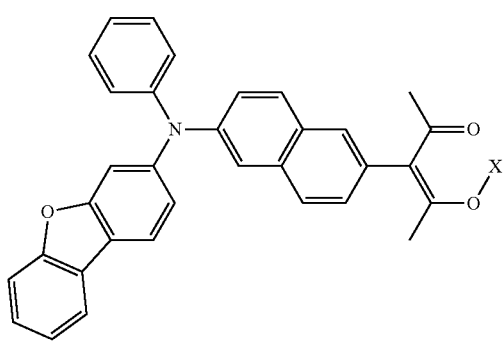
238 (X = H)
239 (X = BF$_2$)
240 (X = BMes$_2$)
160
-continued
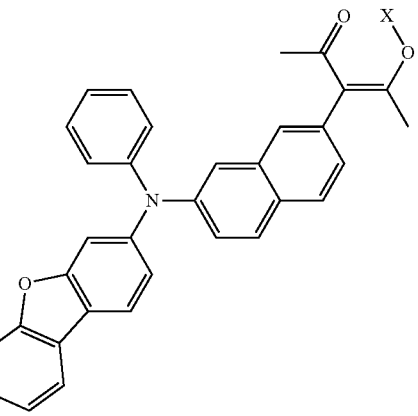
241 (X = H)
242 (X = BF$_2$)
243 (X = BMes$_2$)
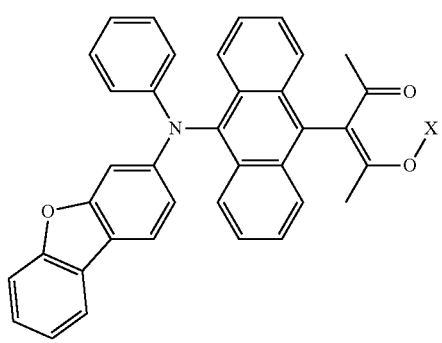
244 (X = H)
245 (X = BF$_2$)
246 (X = BMes$_2$)
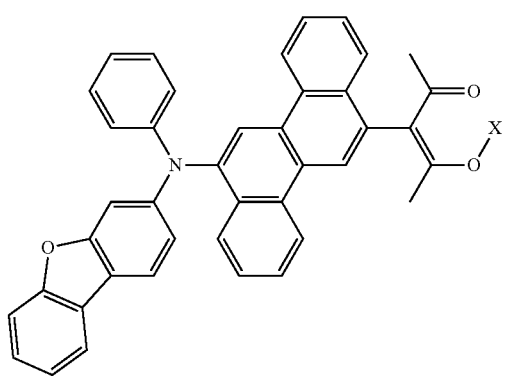
247 (X = H)
248 (X = BF$_2$)
249 (X = BMes$_2$)

-continued
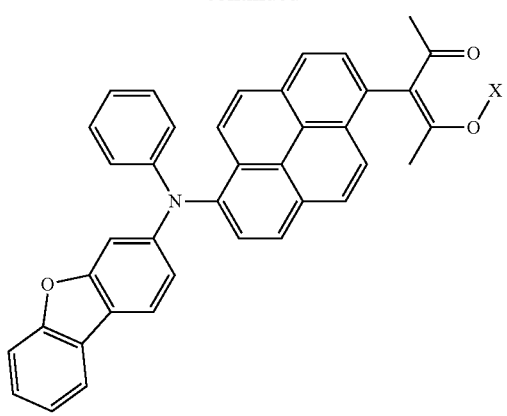
250 (X = H)
251 (X = BF$_2$)
252 (X = BMes$_2$)
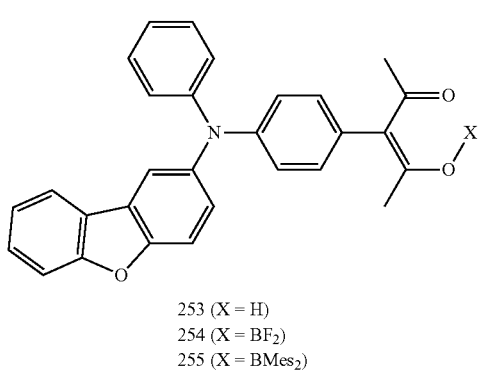
253 (X = H)
254 (X = BF$_2$)
255 (X = BMes$_2$)
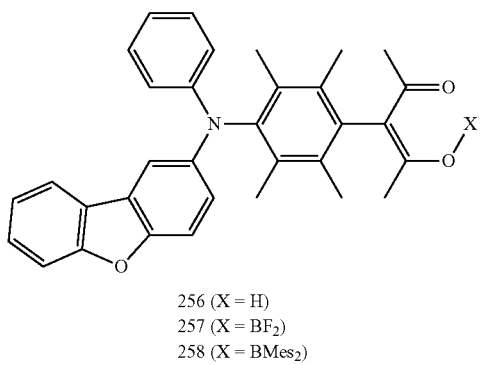
256 (X = H)
257 (X = BF$_2$)
258 (X = BMes$_2$)
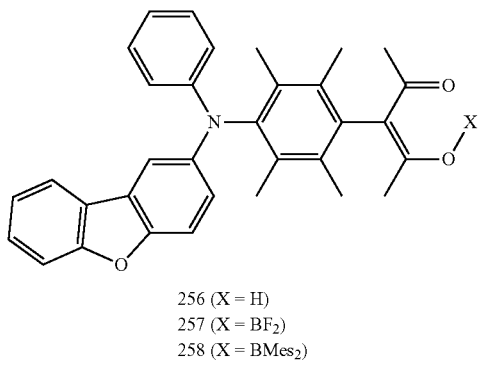
256 (X = H)
257 (X = BF$_2$)
258 (X = BMes$_2$)
-continued
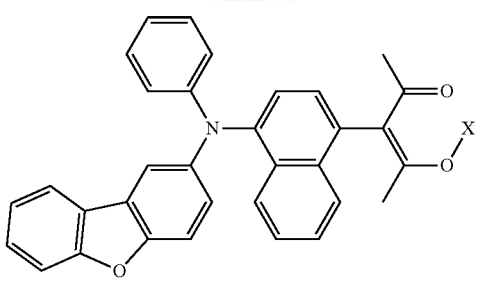
259 (X = H)
260 (X = BF$_2$)
261 (X = BMes$_2$)
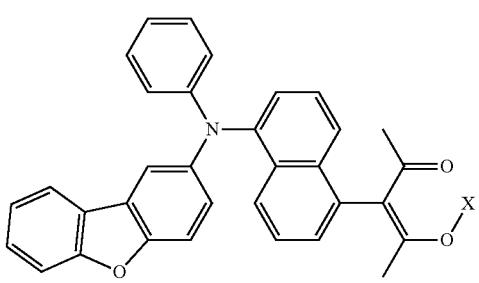
262 (X = H)
263 (X = BF$_2$)
264 (X = BMes$_2$)
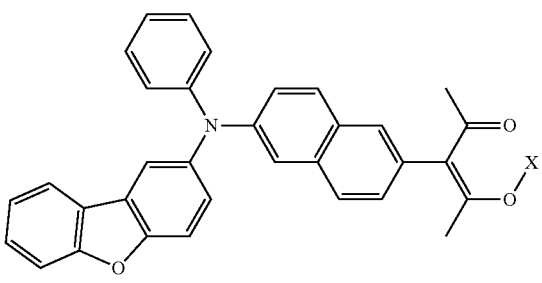
265 (X = H)
266 (X = BF$_2$)
267 (X = BMes$_2$)
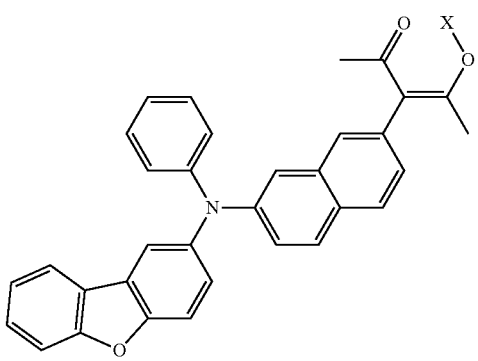
268 (X = H)
269 (X = BF$_2$)
270 (X = BMes$_2$)

-continued
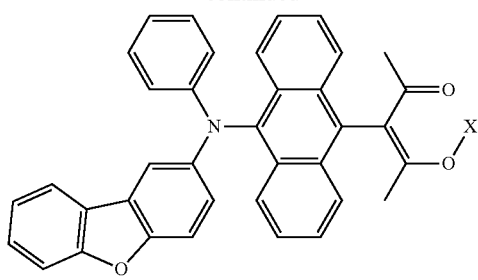
271 (X = H)
272 (X = BF₂)
273 (X = BMes₂)
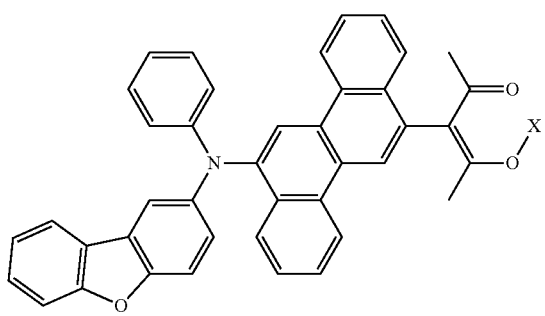
274 (X = H)
275 (X = BF₂)
276 (X = BMes₂)
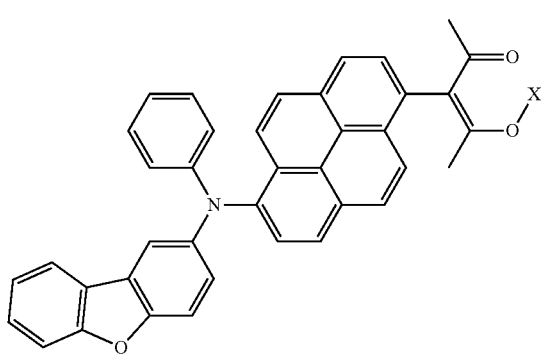
277 (X = H)
278 (X = BF₂)
279 (X = BMes₂)
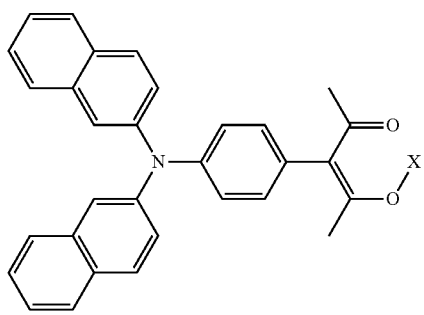
280 (X = H)
281 (X = BF₂)
282 (X = BMes₂)
-continued
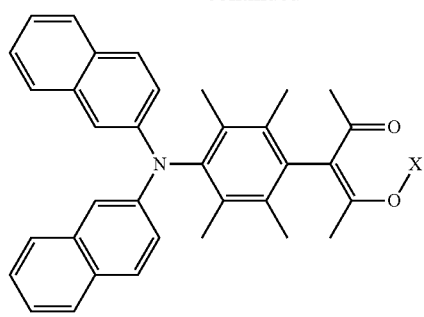
283 (X = H)
284 (X = BF₂)
285 (X = BMes₂)
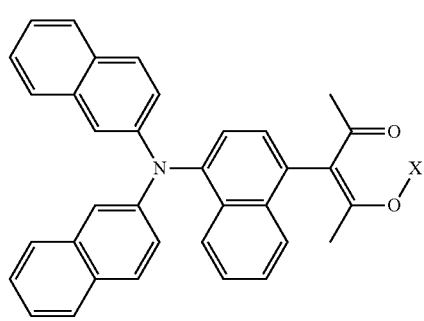
286 (X = H)
287 (X = BF₂)
288 (X = BMes₂)
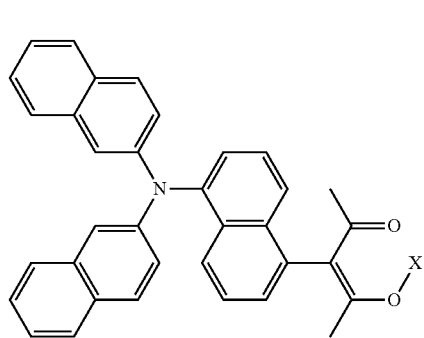
289 (X = H)
290 (X = BF₂)
291 (X = BMes₂)
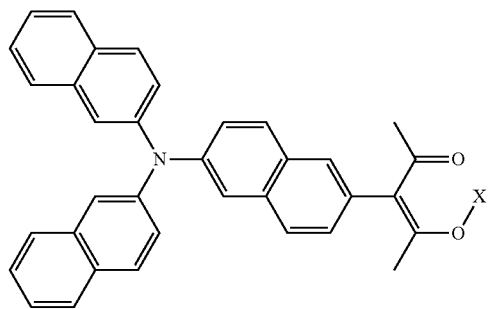
292 (X = H)
293 (X = BF₂)
294 (X = BMes₂)

-continued
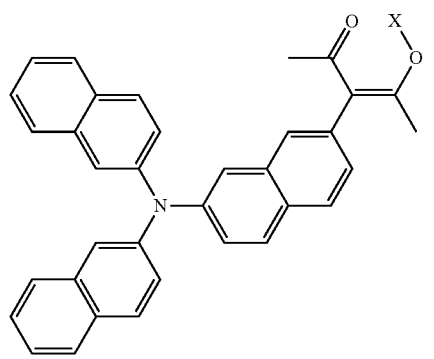
295 (X = H)
296 (X = BF$_2$)
297 (X = BMes$_2$)
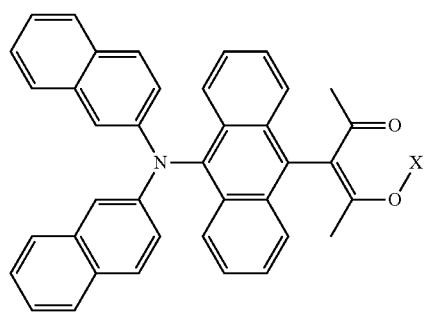
298 (X = H)
299 (X = BF$_2$)
300 (X = BMes$_2$)
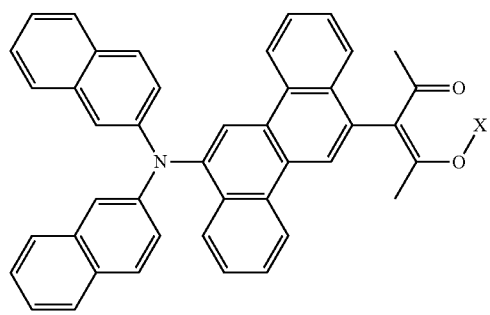
301 (X = H)
302 (X = BF$_2$)
303 (X = BMes$_2$)
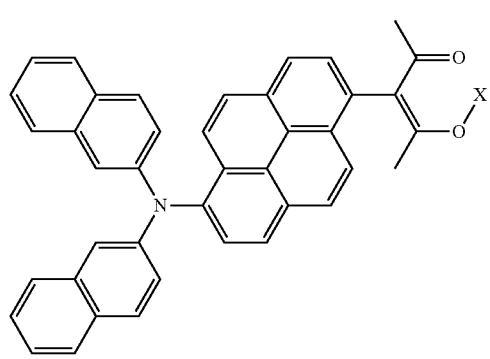
304 (X = H)
305 (X = BF$_2$)
306 (X = BMes$_2$)
-continued
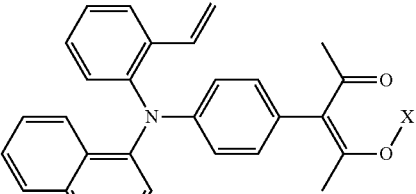
307 (X = H)
308 (X = BF$_2$)
309 (X = BMes$_2$)
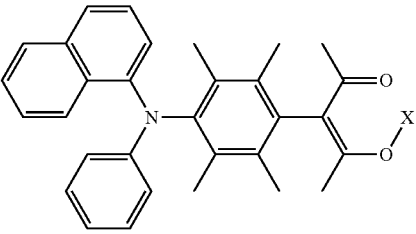
310 (X = H)
311 (X = BF$_2$)
312 (X = BMes$_2$)
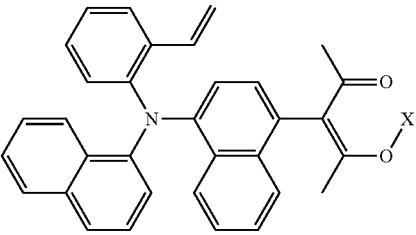
313 (X = H)
314 (X = BF$_2$)
315 (X = BMes$_2$)
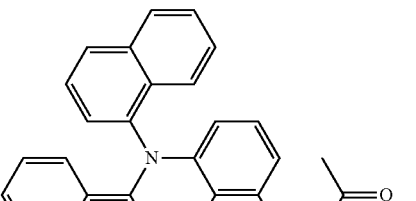
316 (X = H)
317 (X = BF$_2$)
318 (X = BMes$_2$)
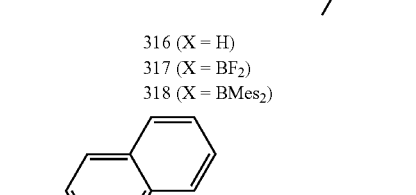
319 (X = H)
320 (X = BF$_2$)
321 (X = BMes$_2$)

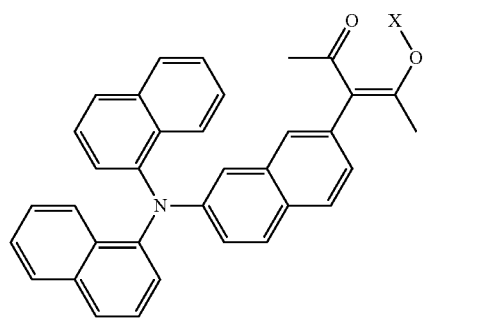
322 (X = H)
323 (X = BF$_2$)
324 (X = BMes$_2$)
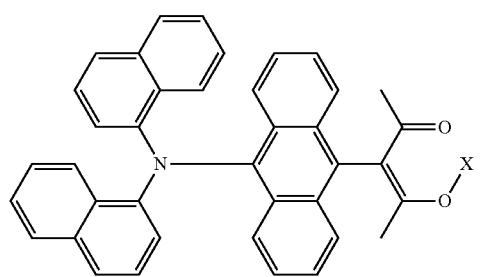
325 (X = H)
326 (X = BF$_2$)
327 (X = BMes$_2$)
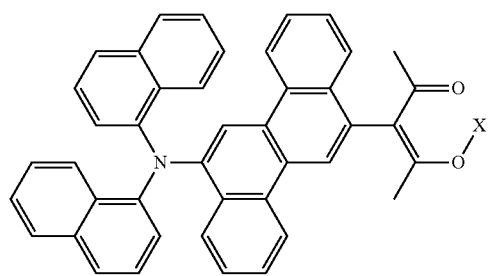
328 (X = H)
329 (X = BF$_2$)
330 (X = BMes$_2$)
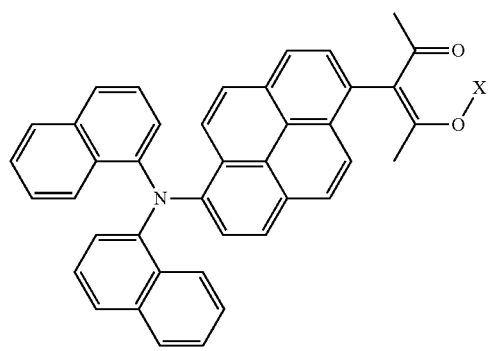
331 (X = H)
332 (X = BF$_2$)
333 (X = BMes$_2$)
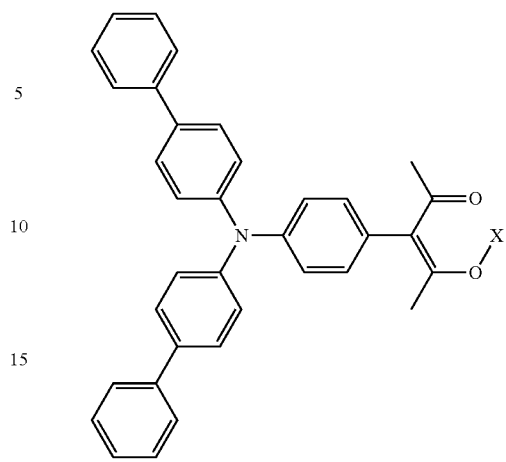
334 (X = H)
335 (X = BF$_2$)
336 (X = BMes$_2$)
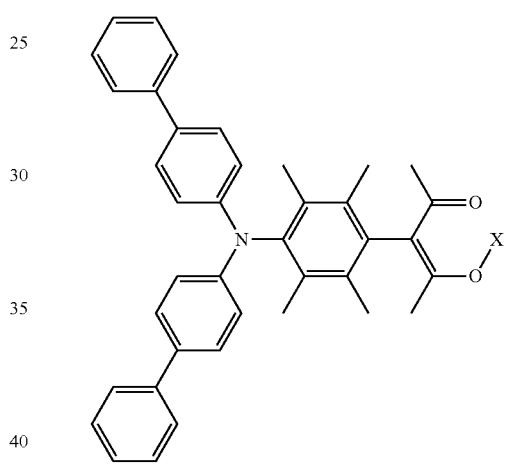
337 (X = H)
338 (X = BF$_2$)
339 (X = BMes$_2$)
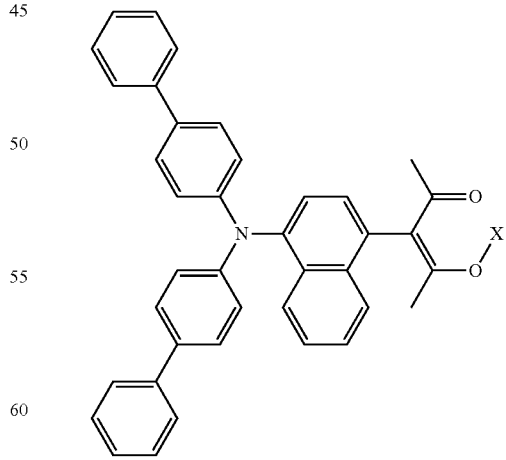
340 (X = H)
341 (X = BF$_2$)
342 (X = BMes$_2$)

169
-continued
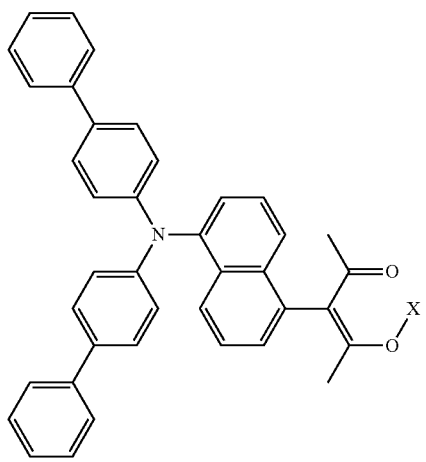
343 (X = H)
344 (X = BF$_2$)
345 (X = BMes$_2$)
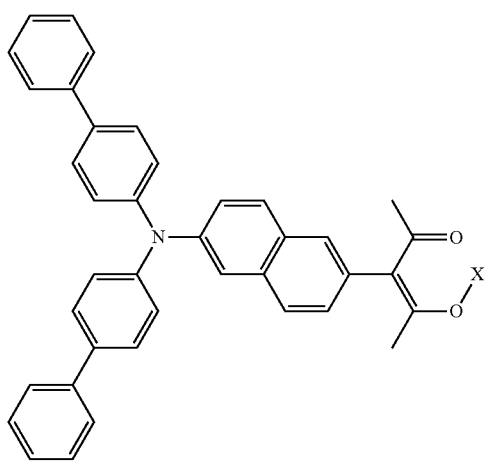
346 (X = H)
347 (X = BF$_2$)
348 (X = BMes$_2$)
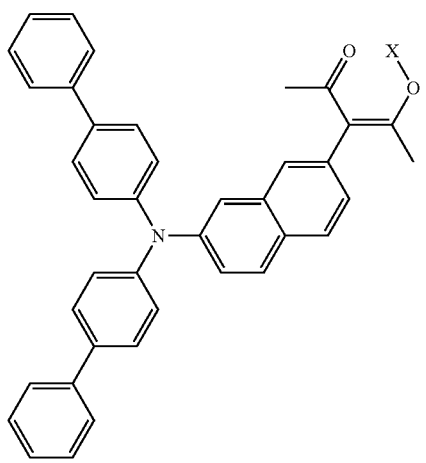
349 (X = H)
350 (X = BF$_2$)
351 (X = BMes$_2$)
170
-continued
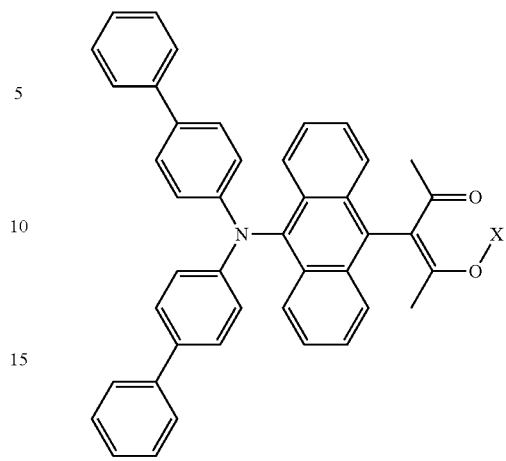
352 (X = H)
353 (X = BF$_2$)
354 (X = BMes$_2$)
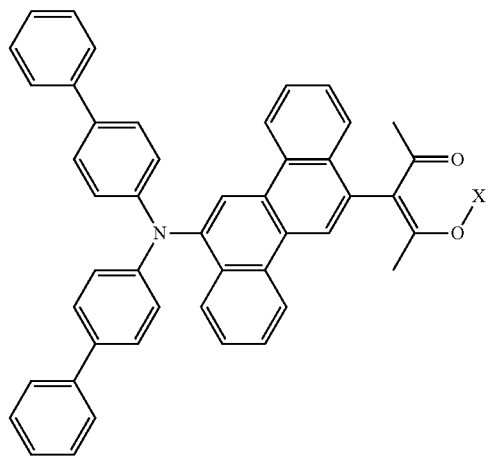
355 (X = H)
356 (X = BF$_2$)
357 (X = BMes$_2$)
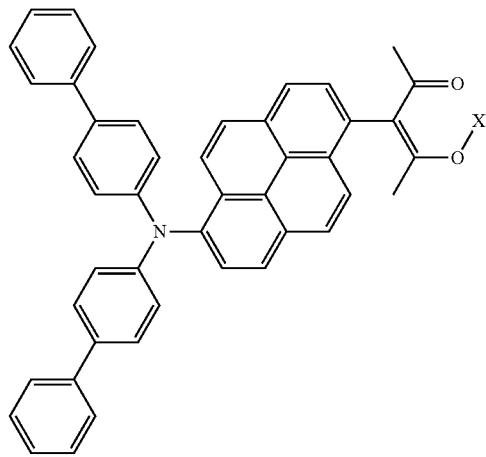
358 (X = H)
359 (X = BF$_2$)
360 (X = BMes$_2$)

-continued
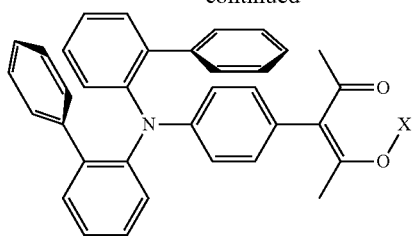
361 (X = H)
362 (X = BX₂)
363 (X = B(Ar₃)₂)
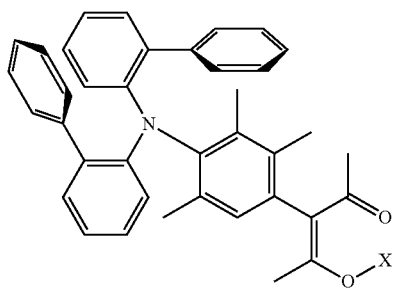
364 (X = H)
365 (X = BX₂)
366 (X = B(Ar₃)₂)
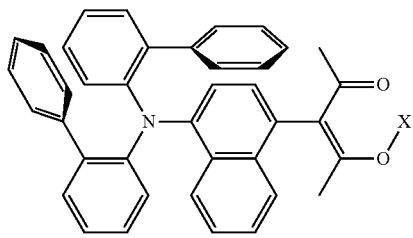
367 (X = H)
368 (X = BX₂)
369 (X = B(Ar₃)₂)
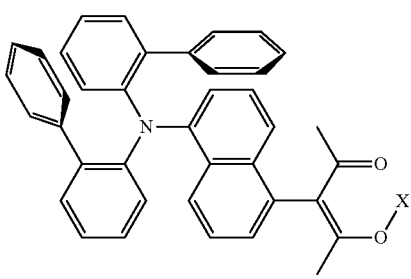
370 (X = H)
371 (X = BF₂)
372 (X = BMes₂)
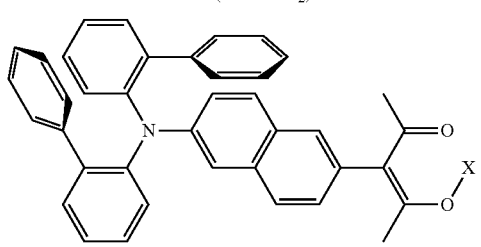
373 (X = H)
374 (X = BF₂)
375 (X = BMes₂)
-continued
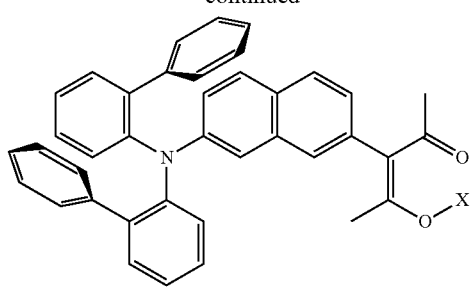
376 (X = H)
377 (X = BF₃)
378 (X = BMes₂)
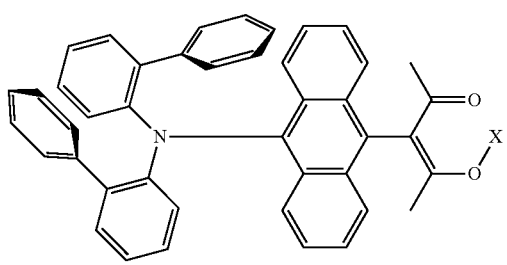
379 (X = H)
380 (X = BF₃)
381 (X = BMes₂)
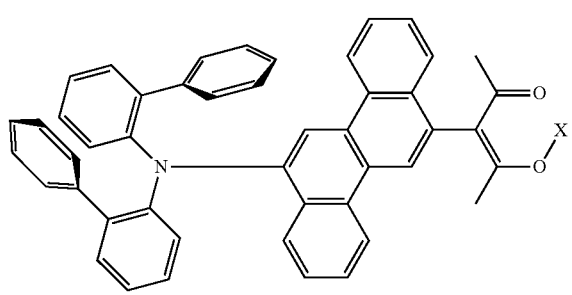
382 (X = H)
383 (X = BF₃)
384 (X = BMes₂)
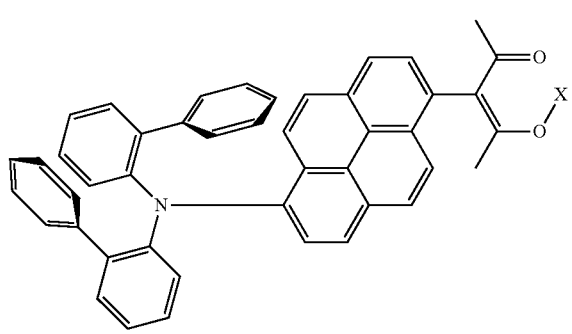
385 (X = H)
386 (X = BF₃)
387 (X = BMes₂)

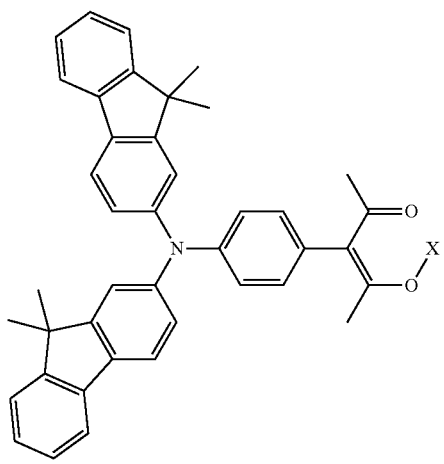
388 (X = H)
389 (X = BF$_2$)
390 (X = BMes$_2$)
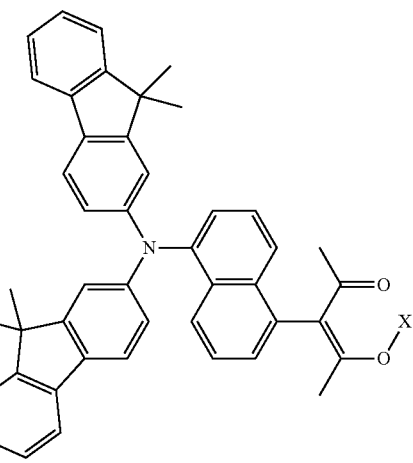
397 (X = H)
398 (X = BF$_2$)
399 (X = BMes$_2$)
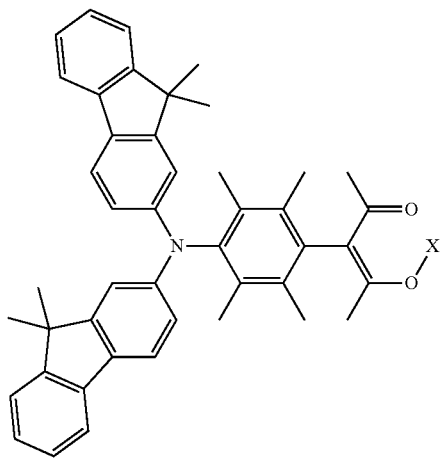
391 (X = H)
392 (X = BF$_2$)
393 (X = BMes$_2$)
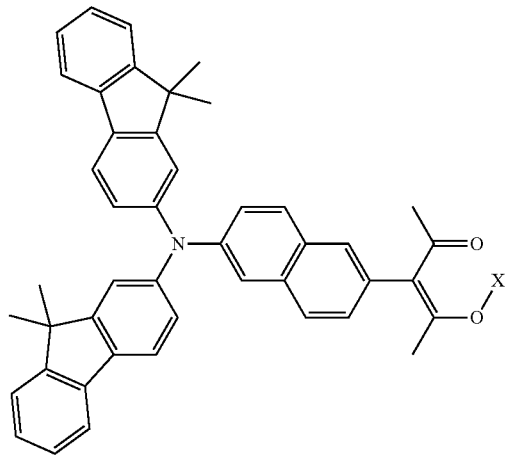
400 (X = H)
401 (X = BF$_2$)
402 (X = BMes$_2$)
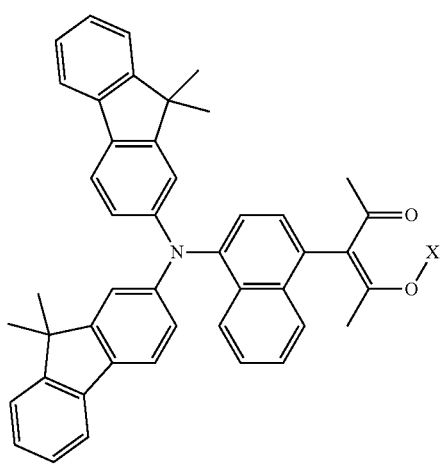
394 (X = H)
395 (X = BF$_2$)
396 (X = BMes$_2$)
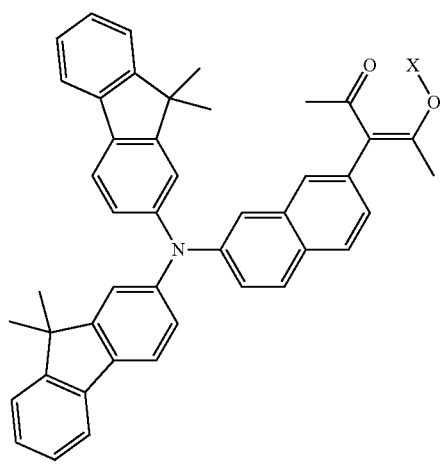
403 (X = H)
404 (X = BF$_2$)
405 (X = BMes$_2$)

175
-continued
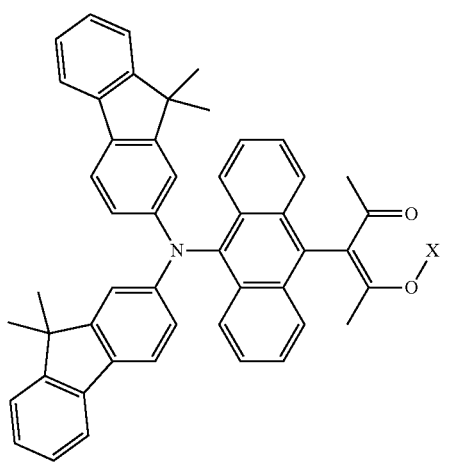
406 (X = H)
407 (X = BF₂)
408 (X = BMes₂)
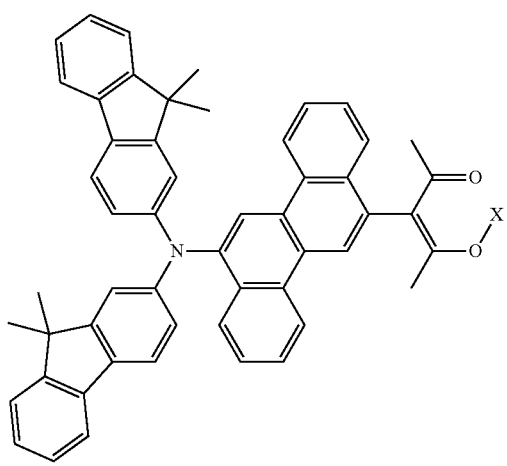
409 (X = H)
410 (X = BF₂)
411 (X = BMes₂)
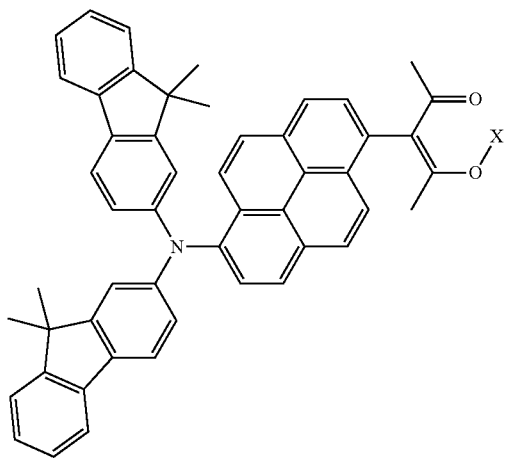
412 (X = H)
413 (X = BF₂)
414 (X = BMes₂)
176
-continued
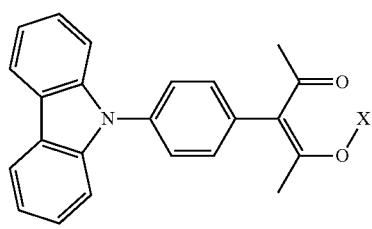
415 (X = H)
416 (X = BF₂)
417 (X = BMes₂)
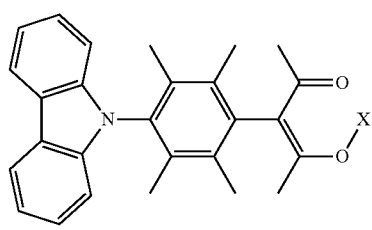
418 (X = H)
419 (X = BF₂)
420 (X = BMes₂)
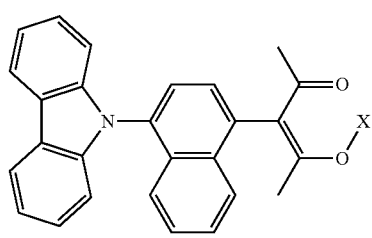
421 (X = H)
422 (X = BF₂)
423 (X = BMes₂)
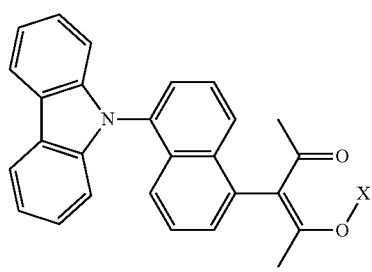
424 (X = H)
425 (X = BF₂)
426 (X = BMes₂)
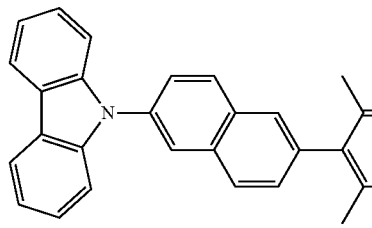
427 (X = H)
428 (X = BF₂)
429 (X = BMes₂)

-continued
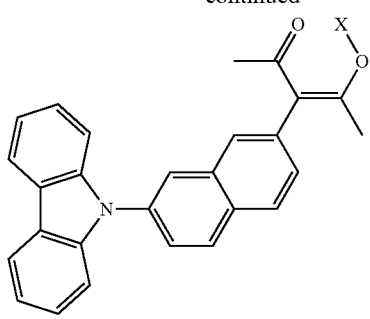
430 (X = H)
431 (X = BF₂)
432 (X = BMes₂)
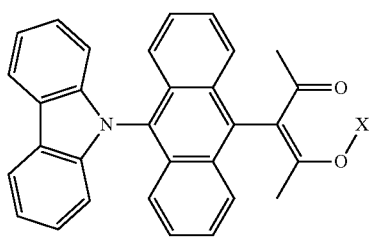
433 (X = H)
434 (X = BF₂)
435 (X = BMes₂)
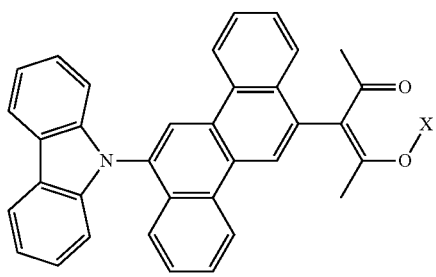
436 (X = H)
437 (X = BF₂)
438 (X = BMes₂)
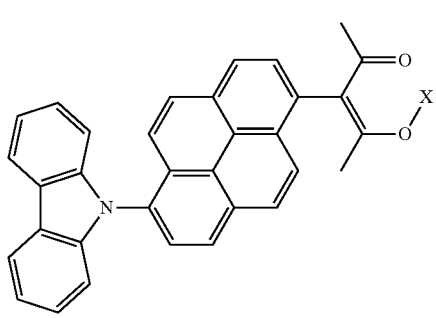
439 (X = H)
440 (X = BF₂)
441 (X = BMes₂)
-continued
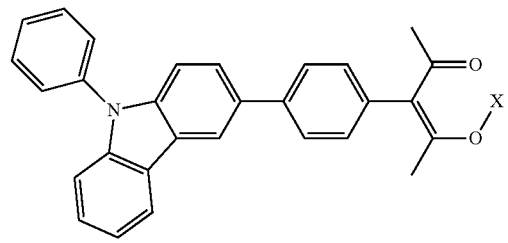
442 (X = H)
443 (X = BF₂)
444 (X = BMes₂)
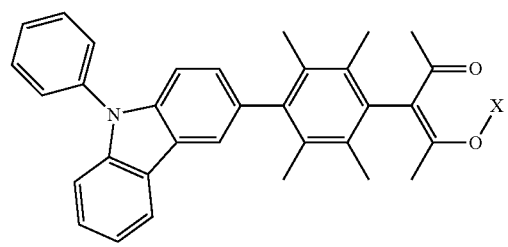
445 (X = H)
446 (X = BF₂)
447 (X = BMes₂)
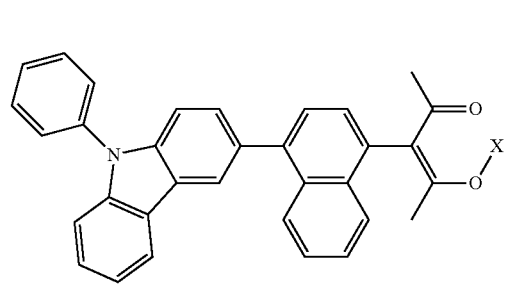
448 (X = H)
449 (X = BF₂)
450 (X = BMes₂)
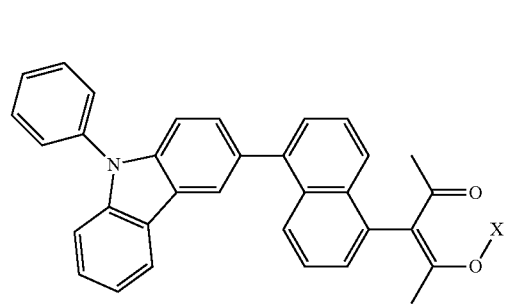
451 (X = H)
452 (X = BF₂)
453 (X = BMes₂)

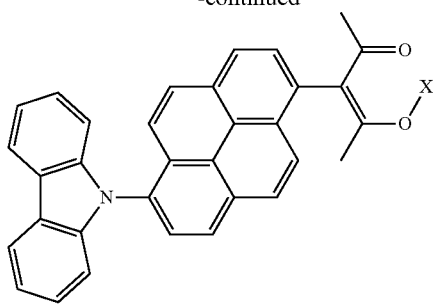
439 (X = H)
440 (X = BF₂)
441 (X = BMes₂)
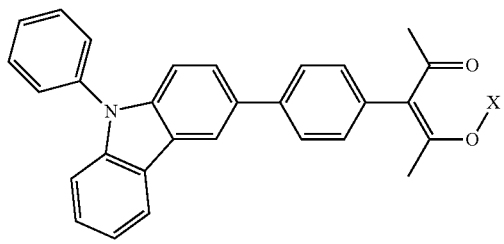
442 (X = H)
443 (X = BF₂)
444 (X = BMes₂)
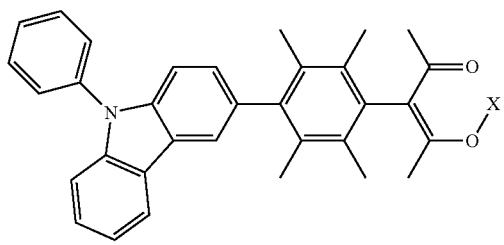
445 (X = H)
446 (X = BF₂)
447 (X = BMes₂)
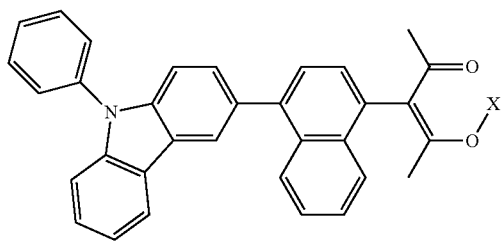
448 (X = H)
449 (X = BF₂)
450 (X = BMes₂)
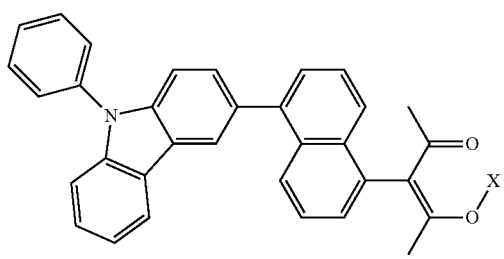
451 (X = H)
452 (X = BF₂)
453 (X = BMes₂)
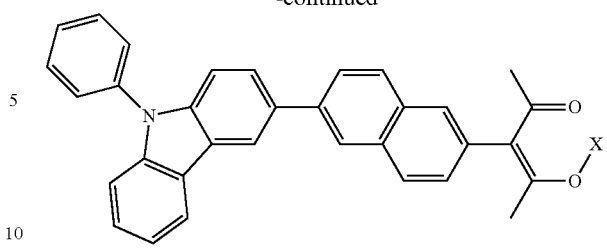
454 (X = H)
455 (X = BF₂)
456 (X = BMes₂)
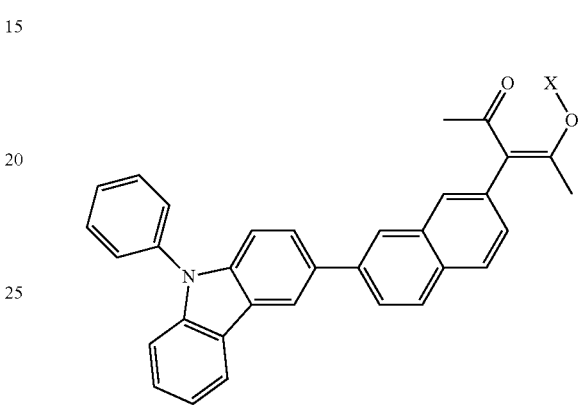
457 (X = H)
458 (X = BF₂)
459 (X = BMes₂)
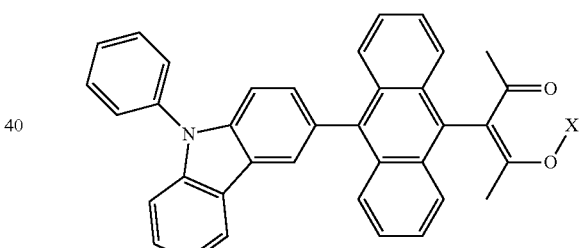
460 (X = H)
461 (X = BF₂)
462 (X = BMes₂)
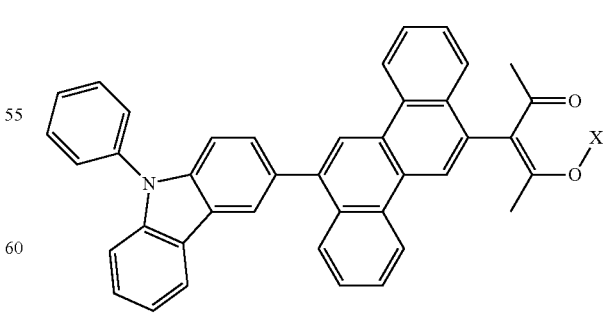
463 (X = H)
464 (X = BF₂)
465 (X = BMes₂)

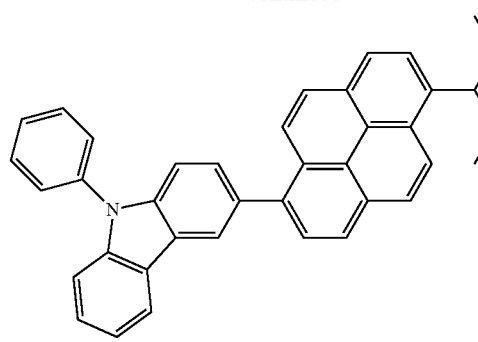
466 (X = H)
467 (X = BF$_2$)
468 (X = BMes$_2$)
469
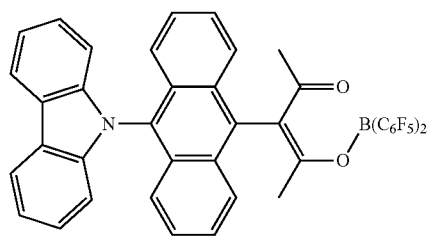
470
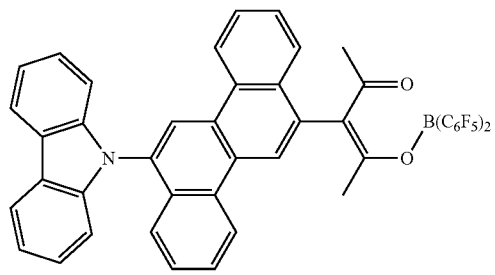
471
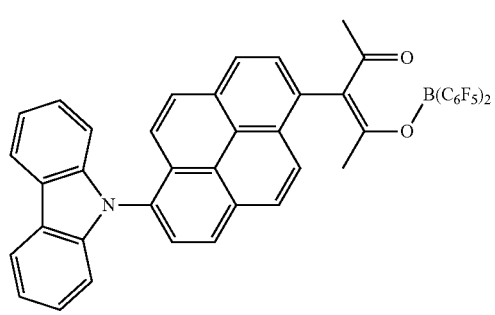
472
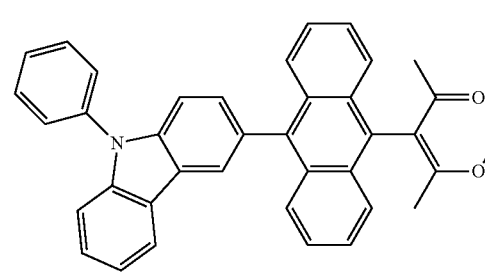
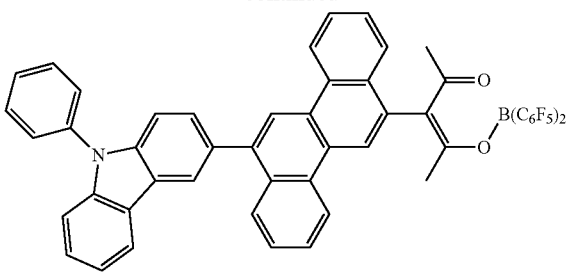
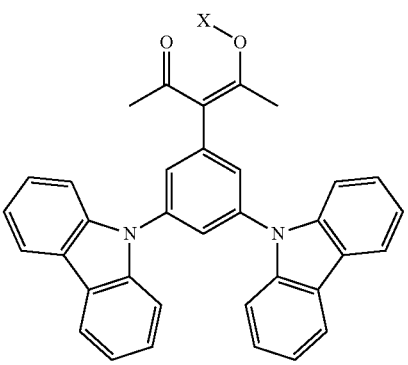
475 (X = H)
476 (X = BF$_2$)
477 (X = BMes$_2$)
478 (B(C$_6$F$_5$)$_2$)
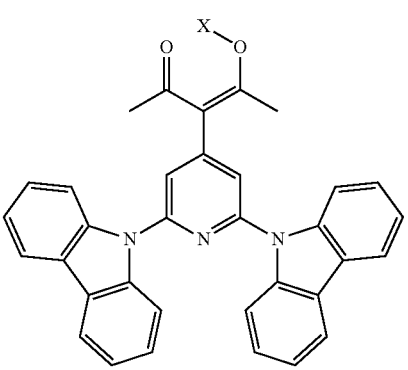
479 (X = H)
480 (X = BF$_2$)
481 (X = BMes$_2$)
482 (B(C$_6$F$_5$)$_2$)

-continued

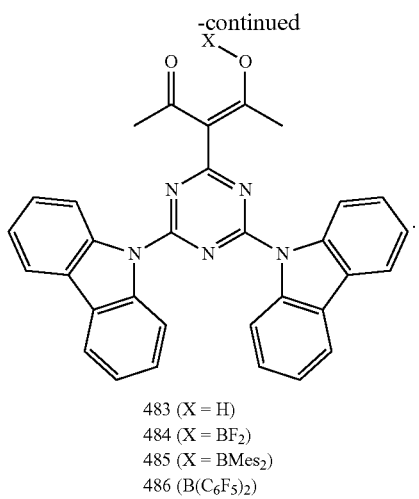

483 (X = H)
484 (X = BF$_2$)
485 (X = BMes$_2$)
486 (B(C$_6$F$_5$)$_2$)

10. An organic light-emitting device comprising:
a first electrode;
a second electrode facing the first electrode; and
an organic layer that is disposed between the first electrode and the second electrode and comprises an emission layer,
wherein the organic layer comprises the compound of claim 1.

11. The organic light-emitting device of claim 10, wherein the emission layer is a blue emission layer.

12. The organic light-emitting device of claim 10, wherein the emission layer is a blue fluorescent emission layer.

13. The organic light-emitting device of claim 10, wherein the emission layer comprises Dopant 1 and Dopant 2.

14. The organic light-emitting device of claim 10, wherein the emission layer comprises Dopant 1 and Dopant 2, and Dopant 2 is the compound of claim 1.

15. The organic light-emitting device of claim 10, wherein the emission layer comprises a host, Dopant 1, and Dopant 2,
Dopant 2 is the compound of claim 1,
weight ratios of the host, Dopant 1, and Dopant 2 are in the following ranges:
75 wt % host 23 wt %,
16 wt % Dopant 1≤24 wt %, and
0.7 wt % Dopant 2≤1.5 wt %
(the sum of the weight ratios of the host, Dopant 1, and Dopant 2 is 100 wt %).

16. The organic light-emitting device of claim 10, wherein the first electrode is an anode,
the second electrode is a cathode, and
the organic layer comprises:
   i) a hole transport region between the first electrode and the emission layer and comprising at least one of a hole transport layer, a hole injection layer, and an electron blocking layer; and
   ii) an electron transport region between the emission layer and the second electrode and comprising at least one of an electron transport layer, a hole blocking layer, and an electron injection layer.

17. The organic light-emitting device of claim 16, wherein the hole transport region comprises a charge-generation material.

18. The organic light-emitting device of claim 16, wherein the electron transport region comprises a metal-containing material.

19. The organic light-emitting device of claim 16, wherein the electron transport region comprises a Li complex.

20. A display apparatus comprising the organic light-emitting device of claim 10, wherein the first electrode of the organic light-emitting device is electrically connected to a source electrode or a drain electrode of a thin film transistor.

* * * * *